(12) United States Patent
Hecker et al.

(10) Patent No.: US 11,286,270 B2
(45) Date of Patent: Mar. 29, 2022

(54) BORONIC ACID DERIVATIVES AND SYNTHESIS THEREOF

(71) Applicant: Qpex Biopharma, Inc., San Diego, CA (US)

(72) Inventors: Scott J. Hecker, Del Mar, CA (US); Serge Henri Boyer, San Diego, CA (US); Hubertus J. A. Dielemans, Beek (NL); Angela Gonzalez de Castro, Maastricht (NL); Andreas H. M. de Vries, Maastricht (NL); Laurent Lefort, Maastricht (NL)

(73) Assignee: Qpex Biopharma, Inc., San Diego, CA (US)

( * ) Notice: Subject to any disclaimer, the term of this patent is extended or adjusted under 35 U.S.C. 154(b) by 114 days.

(21) Appl. No.: 16/755,138

(22) PCT Filed: Oct. 10, 2018

(86) PCT No.: PCT/US2018/055240
§ 371 (c)(1),
(2) Date: Apr. 9, 2020

(87) PCT Pub. No.: WO2019/075084
PCT Pub. Date: Apr. 18, 2019

(65) Prior Publication Data
US 2020/0407373 A1 Dec. 31, 2020

Related U.S. Application Data

(60) Provisional application No. 62/571,149, filed on Oct. 11, 2017.

(51) Int. Cl.
| | | |
|---|---|---|
| *C07F 5/00* | (2006.01) |
| *B01J 23/00* | (2006.01) |
| *C07F 5/02* | (2006.01) |
| *B01J 23/44* | (2006.01) |
| *B01J 23/755* | (2006.01) |

(52) U.S. Cl.
CPC .............. *C07F 5/025* (2013.01); *B01J 23/44* (2013.01); *B01J 23/755* (2013.01)

(58) Field of Classification Search
CPC ................. C07F 5/025; B01J 23/755
See application file for complete search history.

(56) References Cited

U.S. PATENT DOCUMENTS

| | | |
|---|---|---|
| 3,686,398 A | 8/1972 | Kohn et al. |
| 4,194,047 A | 3/1980 | Christensen et al. |
| 4,260,543 A | 4/1981 | Miller |
| 4,353,807 A | 10/1982 | Braid |
| 4,409,214 A | 10/1983 | Takaya et al. |
| 4,822,786 A | 4/1989 | Zama et al. |
| 5,442,100 A | 8/1995 | Bjorkquiest et al. |
| 5,888,998 A | 3/1999 | Maiti et al. |
| 6,184,363 B1 | 2/2001 | Shoichet et al. |
| 6,586,615 B1 | 7/2003 | Kettner et al. |
| 7,271,186 B1 | 9/2007 | Shoichet et al. |
| 7,439,253 B2 | 10/2008 | Lampilas et al. |
| 7,582,621 B2 | 9/2009 | Baker et al. |
| 7,612,087 B2 | 11/2009 | Aszodi et al. |
| 7,674,913 B2 | 3/2010 | Campbell et al. |
| 7,825,139 B2 | 11/2010 | Campbell et al. |
| 8,680,136 B2 | 3/2014 | Hirst et al. |
| 9,012,491 B2 | 4/2015 | Reddy et al. |
| 9,101,638 B2 | 8/2015 | Reddy et al. |
| 9,132,140 B2 | 9/2015 | Reddy et al. |
| 9,156,858 B2 | 10/2015 | Reddy et al. |
| 9,241,947 B2 | 1/2016 | Reddy et al. |
| 9,296,763 B2 | 3/2016 | Hirst et al. |
| 9,511,142 B2 | 12/2016 | Burns et al. |
| 9,642,869 B2 | 5/2017 | Reddy et al. |
| 9,687,497 B1 | 6/2017 | Bis et al. |
| 9,694,025 B2 | 7/2017 | Hirst et al. |
| 10,004,758 B2 | 6/2018 | Hirst et al. |
| 10,206,937 B2 | 2/2019 | Reddy et al. |
| 10,294,249 B2 | 5/2019 | Hecker et al. |
| 10,570,159 B2 | 2/2020 | Hecker et al. |
| 10,618,918 B2 | 4/2020 | Hecker et al. |
| 10,662,205 B2 | 5/2020 | Hecker et al. |
| 2004/0019203 A1 | 1/2004 | Micetich et al. |
| 2004/0157826 A1 | 8/2004 | Lampilas et al. |
| 2005/0020572 A1 | 1/2005 | Aszodi et al. |
| 2005/0070719 A1 | 3/2005 | Belyakov et al. |
| 2006/0019116 A1 | 1/2006 | Conley et al. |

(Continued)

FOREIGN PATENT DOCUMENTS

| | | |
|---|---|---|
| EP | 1550657 A1 | 7/2005 |
| EP | 2508506 A1 | 10/2012 |

(Continued)

OTHER PUBLICATIONS

Abdel-Magid et al., "Reductive Amination of Aldehydes and Ketones with Sodium Triacetoxyborohydride: Studies on Direct and Indirect Reductive Amination Procedures", J Org Chem. (1996) 61(11):3849-3862.

Adediran et al., "A 'cephalosporin-like' cyclic depsipeptide: Synthesis and reaction with beta-lactam-recognizing enzymes", Bioorg Med Chem Lett. (1999) 9(3):341-346.

Aizpurua et al., "Synthesis of benzyl halides from aldehydes promoted by halosilanes and 1,1,3,3-tetramethyldisiloxane (TMDS)", Tetrahedron Lett. (1984) 25(10):1103-1104.

(Continued)

*Primary Examiner* — Sikarl A Witherspoon

(74) *Attorney, Agent, or Firm* — Knobbe, Martens, Olson & Bear LLP

(57) ABSTRACT

Disclosed herein are antimicrobial compounds compositions, pharmaceutical compositions, the method of use and preparation thereof. Some embodiments relate to boronic acid derivatives and their use as therapeutic agents, for example, β-lactamase inhibitors (BLIs).

69 Claims, 1 Drawing Sheet

(56) References Cited

U.S. PATENT DOCUMENTS

| | | |
|---|---|---|
| 2006/0178357 A1 | 8/2006 | Buynak et al. |
| 2006/0210883 A1 | 9/2006 | Chen et al. |
| 2010/0056478 A1 | 3/2010 | Desarbre et al. |
| 2010/0120715 A1 | 5/2010 | Burns et al. |
| 2010/0256092 A1 | 10/2010 | Xia et al. |
| 2010/0292185 A1 | 11/2010 | Burns et al. |
| 2011/0288063 A1 | 11/2011 | Maiti et al. |
| 2012/0040932 A1 | 2/2012 | Hirst et al. |
| 2013/0316978 A1 | 11/2013 | Reddy et al. |
| 2013/0331355 A1 | 12/2013 | Griffith et al. |
| 2013/0345172 A1 | 12/2013 | Hirst et al. |
| 2014/0194381 A1 | 7/2014 | Reddy et al. |
| 2014/0194382 A1 | 7/2014 | Reddy et al. |
| 2014/0194384 A1 | 7/2014 | Reddy et al. |
| 2014/0194385 A1 | 7/2014 | Reddy et al. |
| 2014/0194386 A1 | 7/2014 | Burns et al. |
| 2014/0206648 A1 | 7/2014 | Reddy et al. |
| 2014/0274954 A1 | 9/2014 | Chellappan et al. |
| 2015/0119363 A1 | 4/2015 | Dudley et al. |
| 2016/0220591 A1 | 8/2016 | Hirst et al. |
| 2016/0339045 A1 | 11/2016 | Griffith et al. |
| 2017/0057979 A1 | 3/2017 | Hecker et al. |
| 2017/0088561 A1 | 3/2017 | Reddy et al. |
| 2017/0136047 A1 | 5/2017 | Reddy et al. |
| 2017/0173055 A1 | 6/2017 | Bis et al. |
| 2018/0002351 A1 | 1/2018 | Hecker et al. |
| 2018/0051041 A1 | 2/2018 | Hecker et al. |
| 2018/0071325 A1 | 3/2018 | Hirst et al. |
| 2018/0207183 A1 | 7/2018 | Hirst et al. |
| 2018/0214465 A1 | 8/2018 | Hirst et al. |
| 2019/0084999 A1 | 3/2019 | Hecker et al. |
| 2019/0211037 A1 | 7/2019 | Hecker et al. |
| 2019/0233443 A1 | 8/2019 | Hecker et al. |
| 2020/0181177 A1 | 6/2020 | Hecker et al. |

FOREIGN PATENT DOCUMENTS

| | | |
|---|---|---|
| EP | 2406233 B1 | 11/2013 |
| FR | 2573070 A1 | 5/1986 |
| JP | 2003-229277 | 8/2003 |
| JP | 2004-291253 | 10/2004 |
| WO | WO 1987/05297 | 9/1987 |
| WO | WO 1989/10961 | 11/1989 |
| WO | WO 1998/56392 A1 | 12/1998 |
| WO | WO 2000/035904 A1 | 6/2000 |
| WO | WO 2000/035905 A1 | 6/2000 |
| WO | WO 2001/023374 A1 | 4/2001 |
| WO | WO 2001/030149 | 5/2001 |
| WO | WO 2002/022137 A1 | 3/2002 |
| WO | WO 2002/083884 | 10/2002 |
| WO | WO 2003/070714 | 8/2003 |
| WO | WO 2004/039859 | 5/2004 |
| WO | WO 2004/058679 A2 | 7/2004 |
| WO | WO 2004/064755 A2 | 8/2004 |
| WO | WO 2005/033090 | 4/2005 |
| WO | WO 2005/035532 A1 | 4/2005 |
| WO | WO 2005/087700 | 9/2005 |
| WO | WO 2006/052733 A1 | 5/2006 |
| WO | WO 2006/091771 | 8/2006 |
| WO | WO 2007/058602 A2 | 5/2007 |
| WO | WO 2007/065288 A2 | 6/2007 |
| WO | WO 2007/095638 | 8/2007 |
| WO | WO 2008/039420 A2 | 4/2008 |
| WO | WO 2008/116813 A1 | 10/2008 |
| WO | WO 2009/046098 A1 | 4/2009 |
| WO | WO 2009/064413 A1 | 5/2009 |
| WO | WO 2009/064414 A1 | 5/2009 |
| WO | WO 2009/091856 A1 | 7/2009 |
| WO | WO 2009/117540 A1 | 9/2009 |
| WO | WO 2009/139834 A1 | 11/2009 |
| WO | WO 2009/140309 A2 | 11/2009 |
| WO | WO 2010/056827 A1 | 5/2010 |
| WO | WO 2010/075286 A1 | 7/2010 |
| WO | WO 2010/097675 A1 | 9/2010 |
| WO | WO 2010/130708 A1 | 11/2010 |
| WO | WO 2010/144338 A1 | 12/2010 |
| WO | WO 2011/017125 A1 | 2/2011 |
| WO | WO 2011/103686 A1 | 9/2011 |
| WO | WO 2011/123502 A1 | 10/2011 |
| WO | WO 2011/154953 | 12/2011 |
| WO | WO 2012/021455 A1 | 2/2012 |
| WO | WO 2012/058065 A1 | 5/2012 |
| WO | WO 2012/067664 A1 | 5/2012 |
| WO | WO 2012/106995 A1 | 8/2012 |
| WO | WO 2012/136383 A1 | 10/2012 |
| WO | WO 2013/033461 A1 | 3/2013 |
| WO | WO 2013/053372 A1 | 4/2013 |
| WO | WO 2013/056163 A1 | 4/2013 |
| WO | WO 2013/092979 A1 | 6/2013 |
| WO | WO 2013/104774 A1 | 7/2013 |
| WO | WO 2013/104897 A1 | 7/2013 |
| WO | WO 2013/122888 A2 | 8/2013 |
| WO | WO 2013/184845 A1 | 12/2013 |
| WO | WO 2014/089365 A1 | 6/2014 |
| WO | WO 2014/107535 A1 | 7/2014 |
| WO | WO 2014/107536 A1 | 7/2014 |
| WO | WO 2014/110442 A1 | 7/2014 |
| WO | WO 2014/144380 A1 | 9/2014 |
| WO | WO 2014/151958 A1 | 9/2014 |
| WO | WO 2015/171398 A1 | 11/2015 |
| WO | WO 2015/171430 A1 | 11/2015 |
| WO | WO 2015/179308 A1 | 11/2015 |
| WO | WO 2015/191907 A1 | 12/2015 |
| WO | WO 2016/003929 A1 | 1/2016 |
| WO | WO 2016/065282 A1 | 4/2016 |
| WO | WO 2016/149393 | 9/2016 |
| WO | WO 2018/005662 | 1/2018 |

OTHER PUBLICATIONS

Akiyama et al., "N-Hydroxy Amides. Part 6. Synthesis and Spectroscopic Properties of 1-Hydroxypiperazine-2,5-diones", J Chem Soc., Perkin Trans I, (1989) 2:235-239.

Allen et al., "Ansel's Pharmaceutical Dosage Forms and Drug Delivery Systems", 8th Edition (2004) TOC only.

Ambrose et al., Pharmacokinetics-pharmacodynamics of antimicrobial therapy: it's not just for mice anymore. Clin Infect Dis. (2007) 44: 79-86.

Ambrose et al., "Pharmacokinetics-pharmacodynamics of CB-618 in combination with cefepime, ceftazidime, ceftolozane and meropenem: the pharmacological basis for a stand-alone beta-lactamase inhibitor", Antimicrob Agents Chemother. (Nov. 2017) 61(12): e00630-17; 7 pages.

American Chemical Society. STN Chemical Database Registry RN: 1226917; Jun. 2010; 2 pages.

Arya et al., "Advances in asymmetric enolate methodology", Tetrahedron (2000) 56:917-947.

Austad et al. "Development of a multi kilogram-scale, tandem cyclopropanation ring-expansion reaction en route to hedgehog antagonist IPI-926", Org Process Res Dev., (2016) 20(4):786-798; Supporting Information, 70 pages.

Babic et al., "What's new in antibiotic resistance? Focus on beta-lactamases", Drug Res Updates (2006) 9:142-156.

Banker G.S. et al. [Eds.], Modern Pharmaceutics, 4th Edition; Marcel Dekker, Inc. (2002); Chapters 9 and 10, 98 pages.

Bassetti et al., "New antibiotics for bad bugs: where are we?", Ann Clin Microbiol Antimicrob. (2013) 12:22-36.

Becker, Daniel E., "Antimicrobial Drugs", Anesth Prog (2013) 60:111-123.

Beenen et al., "Asymmetric copper-catalyzed synthesis of alpha-amino boronate esters from N-tert-butanesulfinyl aldimines", J Am Chem Soc. (2008) 130(22):6910-6911.

Berkhout et al., "Pharmacodynamics of Ceftazidime and Avibactam in Neutropenic Mice with Thigh or Lung Infection", Antimicrob Agents Chemother. (2015) 60 (1): 368-375.

Bhavani et al., Pharmacokinetic-Pharmacodynamic (PK_PD) basis for CLSI carbapenem (CARB) susceptibility breakpoint changes. abstr Abstracts of Papers, 50th Interscience Conference on Antimicrobial Agents and Chemotherapy, Sep. 12-15, 2010; #A1-1382, Boston, MA; 3 pages.

(56) References Cited

OTHER PUBLICATIONS

Biedrzycki et al., "Derivatives of tetrahedral boronic acids", J. Organomet. Chem. (1992) 431:255-270.
Bilello et al., "Effect of 2',3'-8 didehydro-3'-deoxythymidine in an in vitro hollow-fiber pharmacodynamic model system correlates with results of dose-ranging clinical studies", Antimicrob Agents Chemother. (1994) 38(6): 1386-1391.
Bou et al., "Cloning, nucleotide sequencing, and analysis of the gene encoding an AmpC beta-lactamase in Acinetobacter baumannii", Antimicrob Agents Chemother (2000) 44(2):428-432.
Bou et al., "OXA-24, a novel class D beta-lactamase with carbapenemase activity in an Acinetobacter baumannii clinical strain", Antimicrob Agents Chemother (2000) 44(6):1556-1561 and Erratum: Antimicrob Agents Chemother. (2006) 50(6) 2280.
Bowker et al., Comparative pharmacodynamics of meropenem using an in-vitro model to simulate once, twice and three times daily dosing in humans. J Antimicrob Chemother (1998) 42:461-467.
Brabez et al., "Design,synthesis, and biological studies of efficient multivalent melanotropin ligands: tools toward melanoma diagnosis and treatment", J Med Chem. (2011) 54(20):7375-7384.
Braisted et al., "Discovery of a potent small molecule IL-2 inhibitor through fragment assembly", J Am Chem Soc., (2003) 125(13): 3714-3715; Supporting Information, 42 pages.
Brosz et al., "Resolution of alpha-aminoboronic esters by diastereoselective crystallization with pinanediols. Confirmation by x-ray analysis", Tetrahedron: Asymmetry (1997) 8(9):1435-1440.
Buesking et al., "Asymmetric Synthesis of Protected alpha-Amino Boronic Acid Derivatives with an Air- and Moisture-stable Cu(II) Catalyst", J Org Chem. (Mar. 2014) 79(8): 3671-3677.
Bulik et al., "Comparison of the activity of a human simulated, high-dose, prolonged infusion of meropenem against Klebsiella pneumoniae producing the KPC carbapenemase versus that against Pseudomonas aeruginosa in an in vitro pharmacodynamic model", Antimicrob Agents Chemother (2010) 54(2): 804-810.
Bundgaard H. [Ed.], "Design of Prodrugs", Elsevier (1985); TOC, 2 pages.
Bush et al., "Minireview: Updated Functional Classification of beta-Lactamases," Antimicrob Agents Chemo. (2010) 54(3):969-976.
CAS Registry No. 2005:329437 CAPLUS; "Product subclass 28: Vinylboranes", Vaultier et al., (2004); XP-002764965; 1 page.
CAS Registry Nos. 69190-59/60 (2-(bis(phenylthio)methyl)-4,4,5,5-tetramethyl-1,3,2-dioxaborolane) and 69190-60-9 (2-(bis(phenylthio)methyl)-1,3,2-dioxaborinane) Scheme 18 (2015); 2 pages.
CAS Registry No. 105892-95-3 Boronic acid [1-(phenylsulfonyl)heptyl]-, dimethyl ester (2015); 2 pages.
CAS Registry No. 831209-98-4 6H-Dibenz[c,e][1,2]oxaborin, 6a, 10a-dihydro-6-hydroxy; Entered STN: Feb. 15, 2005; 1 page.
CAS Registry No. 831210-03-8 6H-Dibenz[c,e][1,2]oxaborin, 2,4-dibromo-6a, 10a-dihydro-6-hydroxy; Feb. 15, 2005; 1 page.
Chandrasekhar et al., "The first Corey-Chaykovsky epoxidation and cyclopropanation in ionic liquids", Tetrahedron Letts. (2003) 44:3629-3630.
Charette et al., "Palladium-catalyzed Suzuki-type cross-couplings of iodocyclopropanes with boronic acids: Synthesis of trans-1,2-dicyclopropyl alkenes", J Org Chem. (1996) 61(25): 8718-8719; Supporting Information, 52 pages.
Cheng et al., "Synthesis of Aryl Thioethers through the N-Chlorosuccinimide-Promoted Cross-Coupling Reaction of Thiols with Grignard Reagents", J Org Chem. (2012) 77(22):10369-10374.
Chemicalland21.com. "Meglumine", Jun. 7, 2011. Downloaded from </www.chemicalland21.com/lifescience/phar/N-METHYL-D-GLUCAMINE.htm>; 2 pages.
Chinchilla et al., "Recent advances in Sonogashira reactions", Chem Soc Rev., (2011) 40: 5084-5121.
Clark et al., "Concise synthesis of the C-1-C-12 fragment of amphidinolides T1-T5", Org Biomol Chem. (2011) 9(13): 4823-4830.

Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2006) M7-A7 26(2), 64 pages.
Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2009) M07-A8 29(2), 88 pages.
Clinical and Laboratory Standards Institute (formerly NCCLS, National Committee for Clinical Laboratory Standards). "Methods for Dilution of Antimicrobial Susceptibility Tests for Bacteria That Grow Aerobically; Approved Standard—9th Edition", CLSI (Jan. 2012) M07-A9 32(2): 88 pages.
Clinical Trial NCT02168946, "A Phase 3, Multi-Center, Randomized, Open-Label Study of Carbavance (Meropenem/RPX7009) Versus Best Available Therapy in Subjects with Selected Serious Infecations Due to Carbapenem-Resistant Enterobacteriaceae", Oct. 6, 2014; retrieved online from URL:https://clinicaltrials.gov/archive/NCT02168946/20140_10_06.
Conte et al., "Intrapulmonary pharmacokinetics and pharmacodynamics of meropenem", Int J Antimicrob Agents (Dec. 2005) 26(6):449-456.
Coppa et al., "A Facile, Convenient and Selective Homolytic Carbamoylation of Heteroaromatic Bases", Heterocycles (1993) 36(12):2687-2696.
Cornella et al., "Ni-catalyzed stereoselective arylation of inert C—O bonds at low temperatures". Org Lett. (2013) 15(24):6298-6301 with Supporting Information in 50 pages.
Coutts et al., "Two Efficient Methods For The Cleavage of Pinanediol Boronate Esters Yielding The Free Boronic Acids", Tetrahedron Lett. (1994) 35(29):5109-5112.
Craig WA., "Pharmacokinetic/pharmacodynamic parameters: rationale for antibacterial dosing of mice and men", Clin Infect Dis. (1998) 26(1): 1-10.
Cunha, "Meropenem in elderly and renally impaired patients", Int'l J Antimicro Agents (1998) 10: 107-117.
Danziger et al., "Automated Site-directed Drug Design: A General Algorithm for Knowledge Acquisition about Hydrogen-bonding Regions at Protein Surfaces", Proc. Royal Soc London, Series B, Biol. Sciences (1989) 236(1283):101-113.
Darses et al., "Potassium Organotrifluoroborates: New Perspectives in organic Synthesis", Chem Rev. (2008) 108:288-325.
Davoli et al., "Enantioselective total synthesis of (-)-microcarpalide", Tetrahedron (2005) 61:4427-4436.
De Meijere A. [Ed], Science of Synthesis—vol. 24; "Three Carbon-Heteroatom Bonds: Ketene Acetals and Yne-X Compounds", TOC 46 pages.
Di Gioia et al., "Optically Pure N-Hydroxy-O-triisopropylsilyl-alpha-L-amino Acid Methyl Esters from AlCl3-Assisted Ring Opening of Chiral Oxaziridines by Nitrogen Containing Nucleophiles", J Org Chem. (2005) 70(25):10494-10501.
Dörwald F.Z., Side Reactions in Organic Synthesis—A guide to Successful Synthesis Design, Wiley-VCH Verlag GmbH & Co. KGaA, Weinheim, Germany (2005); Preface in 4 pages.
Drawz et al., "Three Decades of beta-Lactamase Inhibitors", Clin Microbiol Reviews (Jan. 2010) 23(1):160-201.
Drusano et al., Meropenem: clinical response in relation to in vitro susceptibility. Clin Microbiol Infect. (2000) 6: 185-194.
Dunetz et al., "Large-scale applications of amide coupling reagents for the synthesis of pharmaceuticals", Org Process Res Develop. (2016) 20(2): 140-177.
Eggen et al., "Total synthesis of cryptophycin-24 (Arenastatin A) amenable to structural modifications in the C16 side chain", J Org Chem. (2000) 65(23): 7792-7799; and Supporting documents, 22 pages.
Eidam et al., "Design, synthesis, crystal structures and antimicrobial activity of sulfonamide boronic acids as beta-lactamase inhibitors", J Med Chem. (2010) 53(21):7852-7863.
Eissenstat et al., "Aminoalkylindoles: Structure-Activity Relationships of Novel Cannabinoid Mimetics", J Med Chem. (1995) 38(16):3094-3105.

(56) References Cited

OTHER PUBLICATIONS

El Nezhawy et al., "Synthesis and antioxidant activity of some thiazolidin-4-one derivatives", Springer; Chemical Monthly/Monatshefte für Chemie (2009) 140(5):531-539.
Endo et al., "Chemoselective Suzuki coupling of diborylmethane for facile synthesis of benzylboronates", Org Lett. (2011) 13(13):3368-3371.
Fan, et al. (2009): STN International HCAPLUS database, Columbus (OH), accession No. 2009: 425839; 6 pages.
Farquhar et al., "Intensely potent doxorubicin analogues: structure-activity relationship", J. Med. Chem. (1998) 41(6):965-972.
Ghosh et al., "Enantioselective total synthesis of (+)-largazole, a potent inhibitor of histone deacetylase", Org Lett. (2008) 10(17):3907-3909.
Giroux, A., "Synthesis of benzylic boronates via palladium-catalyzed cross-coupling reaction of bis(pinacolato)diboron with benzylic halides", Tetrahedron Lett. (2003) 44:233-235.
Goodman et al., [Eds.], "The Pharmacological Basis of Therapeutics", 8th. Edition, Pergamon Press (1990); TOC, 8 pages.
Gorovoy et al., "Boron-Containing Peptidomimetics—A Novel Class of Selective Anti-tubercular Drugs", Chem Biol Drug Des. (Jan. 2013) 81(3):408-413.
Gossinger et al., "Towards EPC-syntheses of the structural class of cochleamycins and macquarimicins. Part 3: EPC-syntheses of the beta-keto lactone subunits and first attempts towards the syntheses of the pentacyclic antibiotics of this group", Tetrahedron (2007) 63:8336-8350.
Graham et al., "D is for Drugs", Chemistry & Industry, Mar. 19, 2013, pp. 28-30, Downloaded from http://www.concertpharma.com/wp-content/uploads/2014/12/ChemistryIndustry-0313.pdf; 3 pages.
Greene, et al., "Greene's Protective Groups in Organic Synthesis", 4th Edition, (2007); pp. 774, 785 & 787.
Gunanathan et al., "Ruthenium catalyzed hydroboration of terminal alkynes to Z vinylboronates", J Am Chem Soc. (2012) 134(35): 14349-14352; Supporting Information, 32 pages.
Hall D.G., [Ed], Boronic Acids [vol. 2]: Preparations and applications in Organic Synthesis, Medicine and Materials, Wiley-VCH, Weinheim, 2nd Edition (2011); TOC.
Hama et al., "Palladium-Catalyzed alpha-Arylation of Zinc Enolates of Esters: Reaction Conditions and Substrate Scope", J Org Chem. (2013) 78(17):8250-8266.
Hartung et al., "Highly Z-selective and Enantioselective Ring Opening/Cross Metathesis Catalyzed by Resolved Stereogenic-At-Ru Complex", J Am Chem Soc. (Jul. 2013) 135(28): 10183-10185.
He et al., "Ligand-promoted borylation of C(sp3)—H bonds with palladium(II) catalysts", Angew Chem Int Ed., (2016) 55(2): 785-789.
Hecker et al., "Discovery of a Cyclic Boronic Acid beta-Lactamase Inhibitor (RPX7009) with Utility vs Class A Serine Carbapenemases", J Med Chem. (Mar. 2015) 58:3682-3692.
Higuchi et al., [Eds.] "Pro-drugs as Novel Drug Delivery Systems", ACS Sumposium Series 14 (1975); TOC, 3 pages.
Höpfl et al., "Dynamic NMR and X-ray diffraction study of (N—B)-diphenyl(2-aminoethoxy) borane derivatives of ephedrines and pseudoephedrines". J Organomet Chem. (1997) 544(2):175-188.
Hoveyda A., "Evolution of catalytic stereoselective olefin metathesis: From ancillary transformation to purveyor of stereochemical identity", J Org Chem. (Jun. 2014) 79(11): 4763-4792.
Hu et al., "Ag(I)-catalyzed C—H borylation of terminal alkynes", Tetrahedron (2014) 70: 5815-5819.
Imanishi et al., "Discovery of a Novel Series of Biphenyl Benzoic Acid Derivatives as Potent and Selective Human beta3-Adrenergic Receptor Agonists with Good Oral Bioavailability. Part I", J Med Chem. (2008) 51(6):1925-1944.
Inglis et al., "Observations on the Deprotection of Pinanediol and Pinacol Boronate Esters via Fluorinated Intermediates", J Org Chem. (2010) 75(2):468-471; Supporting Information, S1-S76.
Ishii et al., "In vitro potentiation of carbapenems with ME1071, a Novel metallo-β-lactamase inhibitor, against metallo-β-lactamase producing pseudomonas aeruginosa clinical isolates." Antimicrob. Agents Chemother. doi:10.1128/AAC.01397-09 (2010) 54(9):3625-3629.
Ishiyama et al., "Palladium(0)-catalyzed cross-coupling reaction of alkoxydiboron with haloarenes: A direct procedure for arylboronic esters", J Org Chem. (1995) 60(23): 7508-7510; Supporting Information, 35 pages.
Ito et al., "An efficient constructive method for a tricyclic system: an important intermediate for the synthesis of tricycloclavulone", Tetrahedron Lett. (2003) 44:1259-1261.
Jadhav et al., "Direct synthesis of [alpha-[(tert-Butoxycarbonyl)amino]alkyl]-boronates from (alpha-Haloalkyl)boronates", Org Chem. (1996) 61(22):7951-7954.
Jagannathan et al., "Synthesis of Boronic Acid Analogues of alpha-Amino Acids by Introducing Side Chains as Electrophiles", J Org Chem. (2001) 66(19):6375-6380.
Jang et al., Copper-catalyzed trans-hydroboration of terminal aryl alkynes: Stereodivergent synthesis of alkenylboron compounds. Org Letts. (2016) 18(6): 1390-1393; Supporting Information in 37 pages.
Jarrett et al., "Nickel(II) bis(phosphine) complexes". Inorg Chem. (1991) 30(9):2098-2104 with Supporting Information in 7 pages.
Jiang et al., "A Practical Synthesis of Cefcapene Pivoxil", Synthesis (2012) 44:207-214.
Johnson et al., "A drug targeting motif for glycosidase inhibitors: An iminosugar-boronate shows unexpectedly selective beta-galactosidase inhibition", Tetrahed Lttrs. (2002) 43(49):8905-8908.
Jordan V.C., "Tamoxifen: A most unlikely pioneering medicine", Drug Discovery (2003) 2:205-213.
Kabalka et al., "Synthesis of a series of bornonated unnatural cyclic amino acids as potential boron neutron capture therapy agents", Appl Organomet Chem. (2008) 22(9):516-522.
Kanai et al., "Synthesis of ortho-Acylbenzylboronates via Cross-Coupling Reaction of (Dialkoxyboryl)methylzinc Reagents with Haloarenes. A Stable ortho-Quinodimethane Precursor", Chem Letts. (1993) 22(5):845-848.
Kawamorita et al., "Synthesis of Primary and Secondary Alkylboronates through Site-Selective C(sp3)-H Activation with Silica-supported Monophosphine-Ir Catalysts", J Am Chem Soc. (2013) 135(8):2947-2950.
Kikuchi et al., "Comparison of the Pharmacodynamics of Biapenem in Bronchial Epithelial Lining Fluid in Healthy Volunteers Given Half-Hour and Three-Hour Intravenous Infusions", Antimicrob Agents Chemother. (Jul. 2009) 53(7):2799-2803.
Kint et al., "New-found fundamentals of bacterial persistence", Trends Microbiol. (2012) 20(12):577-585.
Kinuta et al., "Rhodium-catalyzed borylation of aryl 2-pyridyl ethers through cleavage of the carbon-oxygen bond: borylative removal of the directing group". J Am Chem Soc. (2015) 137(4):1593-1600 with Supporting Information in 198 pages.
Kondo et al., Ruthenium-Catalyzed Monoalkenylation of Aromatic Ketones by Cleavage of Carbon-Heteroatom Bonds with Unconventional Chemoselectivity. Angew Chem Int Ed Engl. (2015) 54(32):9293-9297 with Supporting Information in 95 pages.
Kose et al., "Synthesis of photochromic 2,3-bis(5-methyl-2-phenyl-4-thiazolyl)-1,4-naphthoquinone derivatives", J Photochem Photobiol. A: Chemistry. (2011) 219(1):58-61.
Kotha et al., "Recent applications of the suzuki-miyaura cross-coupling reaction in organic synthesis", Tetrahedron (2002) 58:9633-9695.
Kuang et al., "Convenient and stereoselctive synthesis of (Z)-1-bromo-1-alkenes by microwave-induced reaction", Tetrahedron Letts. (2001) 42(23): 3893-3896.
Kumar et al., "Synthesis of intermediates for the lactone moiety of mevinic acids via tellurium chemistry", J. Org. Chem., (1994) 59(17):4760-4764.
Kumar et al., "Development of Practical Methodologies for the Synthesis of Functionalized Benzoboroxoles", Tetrahedron Lett. (Aug. 25, 2010) 51(34):4482-4485.
Kusakabe et al., "Preparation of Optically Acitve 2-Furylcarbinols by Kinetic Resolution Using the Sharpless Reagent and Their Application in Organic Synthesis", J org Chem (1989) 54(9):2085-2091.

(56) References Cited

OTHER PUBLICATIONS

Kuti et al., "Use of Monte Carlo simulation to design an optimized pharmacodynamic dosing strategy for meropenem", J Clin Pharmacol. (Oct. 2003) 43(10): 1116-1123 with Erratum (2005); 1 page.
Laitar et al., "Catalytic diboration of aldehydes via insertion into the copper-boron bond", J Am Chem Soc. (2006) 128(34):11036-11037.
Lapuebla et al., "Activity of Meropenem Combined with RPX7009, a Novel beta-Lactamase Inhibitor, against Gram-Negative Clinical Isolates in New York City", Antimicrob Agents Chemother. (Aug. 2015) 59(8):4856-4860.
Larock R. [Ed.] Comprehensive Organic Transformations, VCH Publishers 1989; TOC, 11 pages.
Lebel et al., "Boc-protected amines via a mild and efficient one-pot Curtius rearrangement", Org Letts. (2005) 7(19): 4107-4110.
Lee et al., "Vicinal Diboronates in High Enantiomeric Purity through Tandem Site-Selective NHC-Cu-Catalyzed Boron-Copper Additions to Terminal Alkynes", J Am Chem Soc. (Dec. 2009) 131 (51):18234-18235.
Lee et al., "Comparison of 30-min and 3-h infusion regimens for imipenem/cilastatin and for meropenem evaluated by Monte Carlo simulation", Diagn Microbiol Infect Dis. (2010) 68: 251-258.
Li et al., "Population Pharmacokinetic Analysis and Dosing Regimen Optimization of Meropenem in Adult Patients", J Clin Pharmacol. (2006) 46(10): 1171 -1178.
Li et al, "Novel macrocyclic HCV NS3 protease inhibitors derived from α-amino cyclic boronates", Bioorganic Med Chem Lett. (2010) 20:5695-5700.
Li et al., "Synthesis and evaluation of novel alpha-amino cyclic boronates as inhibitors of HCV NS3 protease", Bioorg Med Chem Lett. (2010) 20:3550-3556.
Li et al., "Stereoselective total synthesis of etnangien and etnangien methyl ester", J Org Chem. (2010) 75(8):2429-2444.
Liang et al., "The Efficient Copper(I) (Hexabenzyl)tren Catalyst and Dendritic Analogues for Green "Click" Reactions between Azides and Alkynes in Organic Solvent and in Water: Positive Dendritic Effects and Monometallic Mechanism", Advance Syn Catal. (2011) 353(18): 3434-3450.
Lieberman H.A. [Ed] Pharmaceutical Dosage Forms—Tablets; Marcel Dekker, Inc. (1989) 2nd Ed; TOC; 7 pages.
Lima et al., "Bioisosterism: A Useful Strategy for Molecular Modification and Drug Design", Curr Med Chem. (2005) 12:23-49.
Lin et al., "Enantioselective syn and anti homocrotylation of aldehydes: Application to the formal synthesis of spongidepsin", J Am Chem Soc. (2015) 137(40): 13176-13182; Supporting Information, 177 pages.
Liu et al., "Selective Protein tyrosine phosphatase 1B inhibitors: Targeting the second phosphotyrosine binding site with non-carboxylic acid-containing ligands", J Med Chem. (2003) 46(16):3437-3440; Supporting Information, 38 pages.
Liu et al., "Application of Stereoselective Ether Transfer to the Synthesis of Isotactic Polyethers", J Org Chem. (2010) 75(12):3953-3957.
Livermore et al., "Activities of NXL104 combinations with Ceftazidime and Aztreonam against Carbapenemase-producing Enterobacteriaceae", Antimicr Agents Chemother. (2011) 55(1):390-394.
Livermore et al., "Activity of biapenem (RPX2003) combined with the boronate beta-lactamase inhibitor RPX7009 against carbapenem-resistant Enterobacteriaceae", J Antimicrob Chemother. (Aug. 2013) 68(8):1825-1831.
Lodise et al., "Penetration of meropenem into epithelial lining fluid of patients with ventilator-associated pneumonia", Antimicrob Agents Chemother. (Apr. 2011) 55(4):1606-1610.
Louie et al., Impact of meropenem in combination with tobramycin in a murine model of Pseudomonas aeruginosa pneumonia. Antimicrob Agents Chemother (2013) 57: 2788-2792.
Luithle et al., "Synthesis of enantiomerically pure cis-cyclopropylboronic esters", Eur J Org Chem. (2000) 14: 2557-2562.
MacVane et al., Characterizing in vivo pharmacodynamics of carbapenems against Acinetobacter baumannii in a Murine thigh infection model to support breakpoint determinations. Antimicrob Agents Chemother. (2014) 58: 599-601.
Maguire B. A., Inhibition of Bacterial Ribosome Assembly: a Suitable Drug Target? Microbiol Mol Biol Rev. (2009) 73(1):22-35.
Malfertheiner et al., "Current concepts in the management of Helicobacter pylori infection: the Maastricht III Consensus Report", Gut (2007) 56(6):772-781.
Matteson et al., "Iodomethaneboronic Esters and Aminomethaneboronic Esters", J Organomet. Chem. (1979) 170:259-264.
Matteson et al., "A Directed Chiral Synthesis of Amino Acids from Boronic Esters", Tetrahedron Lett. (1987) 28(39):4499-4502.
Matteson, D.S., "Asymmetric Synthesis with Boronic Esters", Acc Chem Res. (1988) 21(8):294-300.
Matteson, "Boronic esters in stereodirected synthesis", Tetrahedron (1989) 45(7):1859-1885.
Matteson et al., "A stereospecific convergent coupling of nucleophilic and electrophilic chiral carbons", J. Am. Chem. Soc. (1989) 111:4399-4402.
Matteson et al., "Synthesis of asymmetrically deuterated glycerol and dibenzylglyceraldehyde via boronic esters", J. Am. Chem. Soc. (1990) 112:3964-3969.
Matteson et al., "(Alkoxyalkyl)boronic Ester Intermediates for Asymmetric Synthesis", Organometallics (1996) 15:152-163.
Matteson, "Alpha-Halo Baronic Esters in Asymmetric Synthesis", Tetrahedron (1998) 54(36):10555-10607.
Matteson et al., "Glass-Catalyzed Conversion of Boronic Esters of Asymmetric Diols to Diol Sulfites and Amine Complexes of Boron Halides", Oranometallics (2001) 20(13):2920-2923 & supporting Information (9 pages).
Matteson et al., "Cesium Alkyltrifluoroborates from Asymmetric Boronic Esters", Synlett (Jul. 2006) 20:3501-3503.
Matteson et al., "Synthesis of a (Beta-acetamido-alpha-acetoxyethyl) boronic ester via azido boronic esters", J Organomet Chem. (2008) 693:2258-2262.
Matteson, "Boronic Esters in Asymmetric Synthesis", J Org Chem. (Oct. 2013) 78(20): 10009-10023.
McOmie J.R.W. [Ed], Protective Groups in Organic Chemistry, Plenum Press, London & New York (1973); TOC, 3 pages.
Meanwell, "Synopsis of some recent tactical application of bioisosteres in drug design", J. Med. Chem. (2011) 54:2529-2591.
McSharry et al., "Prediction of the pharmacodynamically linked variable of oseltamivir carboxylate for influenza A virus using an in vitro hollow-fiber infection model system", Antimicrob Agents Chemother (2009) 53(6): 2375-2381.
Mendoza et al., "Bis(phenylthio)methaneboronic Esters as Sources of Carbanions and Ketene Thioacetals", J Org Chem. (1979) 44(8):1352-1354.
Micalizio et al., "A Boronic Ester Annulation Strategy for Diversity-Oriented Organic Synthesis", Angew Chem Int Ed Engl. (2002) 41(1):152-154.
Miriagou et al., "Acquired carbapenemases in Gram-negative bacterial pathogens: detection and surveillance issues", Clin Microbiol Infect. (Feb. 2010) 16(2):112-122.
Mkhalid et al., "C—H activation for the construction of C—B bonds", Chem Rev. (2010) 110(2): 890-931.
Molander et al., "Highly stereoselective synthesis of cis-alkenyl pinacolboronates and potassium cis-alkenyltrifluoroborates via a hydroboration/protodeboronation approach", J Org Chem. (2008) 73(17): 6841-6844.
Montalbetti et al., "Amide bond formation and peptide coupling", Tetrahedron (2005) 61:10827-10852.
Montefour et al., "Acinetobacter baumannii: an emerging multidrug-resistant pathogen in critical care", Crit Care Nurse (2008) 28(1):15-25.
Morandi et al., "Structure-based optimization of cephalothin-analogue boronic acids as beta-lactamase inhibitors", Bioorg Med Chem. (2008) 16(3):1195-205. Epub Nov. 7, 2007.
Mori et al., "Synthesis of 1,3-dienes from alkynes and ethylene: Acetic acid 2-methylene-3-phenethylbut-3-enyl ester", Org Synth. (2005) 81: 1-13.
Morrill et al., "Treatment Options for Carbapenem-Resistant Enterobacteriaceae Infections", Open Forum Infectious Diseases [OFID] Apr. 2015; 15 pages.

(56) References Cited

OTHER PUBLICATIONS

Munar et al., "Drug Dosing Adjustments in Patients with Chronic Kidney Disease", Am Fam Physician (May 2007) 75(1): 1487-1496.
Nema et al., "Excipients and Their Role in Approved Injectable Products: Current Usage and Future Directions", PDA J Pharm Sci Technol. (2011) 65(3):287-332.
Ness et al., "Structure-based design guides the improved efficacy of deacylation transition state analogue inhibitors of TEM-1 beta-Lactamase", Biochemistry (2000) 39(18):5312-5321.
Nicasio et al., "Pharmacokinetics-Pharmacodynamics of Tazobactam in Combination with Piperacillin in an In Vitro Infection Model", Antimicrob Agents Chemother. (2016) 60: 2075-2080. doi: 10.1128/AAC.02747-15.
Nicolau DP., "Pharmacokinetic and pharmacodynamic properties of meropenem", Clin Infect Dis. (2008) 47 Suppl 1: S32-S40.
Noguchi et al., "Boron-masking strategy for the selective synthesis of oligoarenes via iterative Suzuki-Miyaura coupling", J Am Chem Soc. (2007) 129(4): 758-759; Supporting Information, 46 pages.
Nordmann et al., How To Detect NDM-1 Producers, J. Clin. Micro. (2011) 49:718-721.
Overman et al., "Organic Synthesis—Working with Hazardous Chemicals", Org Synth. (1990) 68: 182; 5 pages.
Panek et al., "Diastereoselectivity in the borane methyl sulfide promoted hydroboration of .alpha.-alkoxy-.beta, gamma.-unsaturated esters. Documentation of an alkoxy-directed hydroboration reaction", J. Org. Chem. (1992) 57(20):5288-5290.
Paquette L.A. [Ed.] Encyclopedia of Reagents for Organic Synthesis, vol. 1; J. Wiley & Sons (1995); Cover Only.
Patani et al., "Bioisosterism: A Rational Approach in Drug Design", Chem Rev. (1996) 96:3147-3176.
Paterson et al., "Extended-Spectrum beta-Lactamases: a Clinical Update", Clin Microbiol Rev. (2005) 18(4):657-686.
Pellissier, H., "Recent developments in asymmetric cyclopropanation", Tetrahedron (2008) 64(30-31): 7041-7095.
Perez et al., "Why are we afraid of Acinetobacter baumannii?", Expert Rev Anti Infect Ther. (2008) 6(3): 269-71.
Pietruszka et al., "Enantiomerically pure cyclopropylamines from cyclopropylboronic esters", Eur J Org Chem. (2009) 34: 5998-6008.
Pine et al., "Resonance vs. Tautomerism" in Organic Chemistry; McGraw-Hill, New York 4th Ed. (1980), pp. 218-219.
Pintaric et al., "An Opportunity for Mg-Catalyzed Grignard-Type Reactions: Direct Coupling of Benzylic Halides with Pinacolborane with 10 mol % of Magnesium", J Am Chem Soc. (2010) 132(34): 11825-11827.
Powell et al., "Compendium of excipients for parenteral formulations", PDA J Pharm Sci Technol.(1998) 52(5):238-311.
Queenan et al., "Carbapenemases: the Versatile β-Lactamases", Clin Microbiol Rev. (Jun. 2007) 20(3): 440-458.
Rehm et al., *Staphylococcus aureus*: Methicillin-susceptible *S. aureus* to Methicillin-resistant *S. aureus* and Vancomycin-resistant *S. aureus*", Clin Inf Diseases. (2010) 51(S2):S176-S182.
Reissig et al.,"High diastereoselection in the alkylation of siloxy-substituted methyl cyclopropanecarboxylates: consequence of a pyramidal ester enolate anion?", J. Am. Chem. Soc. (1982) 104:1735-1737.
Robak et al., "Synthesis and applications of tert-butanesulfinamide", Chem Rev. (2010) 110(6):3600-3740.
Roche, E.B. (Ed.)., Bioreversible Carriers in Drug Design: Theory and Application. New York: Pergamon Press (1987); pp. 14-21.
Rodriguez-Martinez et al., "VIM-19, a Metallo-beta-lactamase with increased Carbapenemase Activity from *Escherichia coli* and Klebsiella pneumoniae", Antimicro Agents Chemother. (2010) 54(1):471-476.
Rosen et al., "Nickel-catalyzed cross-couplings involving carbon-oxygen bonds". Chem Rev. (2011) 111(3):1346-1416.
Rubino et al., "Phase 1 Study of the Safety, Tolerability, and Pharmacokinetics of Vaborbactam and Meropenem Alone and in Combination following Single and Multiple Doses in Healthy Adult Subjects", Antimicrob Agents Chemother. (Apr. 2018) 62(4): E02228-17; 12 pages.

Sabet et al., "In Vivo Efficacy of Carbavance (Meropenem/RPX7009) Against KPC-producing Enterobacteriaceae", Abstracts of the 54th Interscience Conference on Antimicrobial Agents and Chemotherapy (Sep. 5-9, 2014) F-958; 3 pages.
Sabet et al., "Activity of Simulated Human Dosage Regimens of Meropenem and Vaborbactam against Carbapenem-Resistant Enterobacteriaceae in an In Vitro Hollow-Fiber Model", Antimicrob Agents Chemother (2017) 62. pii: e01969-17. doi: 10.1128/AAC.01969-17.
Sabet et al., "Activity of Meropenem-Vaborbactam in Mouse Models of Infection Due to KPC-Producing Carbapenem-Resistant Enterobacteriaceae", Antimicrob Agents Chemother. (2017) 62:1 10 e01446-379 17.
Saito et al., "Nickel-catalyzed boron insertion into the C2—O bond of benzofurans". J Am Chem Soc. (2016)., 138(47), 15315-15318 with Supporting Information in 103 pages.
Sawant et al., "Synthesis of the C1-C13 Fragment of Biselyngbyaside", Synlett (2011) 20: 3002-3004.
Sawyer et al., "Physical properties and synthetic utility of a-alkoxyorganolithium species as studied through ligand selectivity in tin-lithium exchange", J. Am. Chem. Soc. (1988) 110:842-853.
Schwarzer et al., "Combined theoretical and experimental studies of nickel-catalyzed cross-coupling of methoxyarenes with arylboronic esters via C—O bond cleavage". J Am Chem Soc. (2017) 139(30):10347-10358 with Suppl. Information in 255 pages.
Scriven et al., "Azides: Their preparation and synthetic uses", Chem Rev. (1988) 88(2): 297-368.
Selander et al., "Palladium-catalyzed allylic C—OH functionalization for efficient synthesis of functionalized allylsilanes", J Am Chem Soc. (2011) 133(3):409-411.
Shaffer, Robyn Kroop, "The Challenge of Antibiotic-Resistant *Staphylococcus*: Lessons from Hospital Nurseries in the mid-20th Century", Yale J Biol Med. (2013) 86:261-270.
Shao et al., "Asymmetric hydrogenation of 3,5-Dioxoesters catalyzed by Ru-binap complex: A short step asymmetric synthesis of 6-substituted 5,6-dehydro-2-pyrones", Tetrahedron (1993) 49(10):1997-2010.
Singer et al., "Catalytic, enantioselective acetate aldol additions to alpha-, beta-ynals: Preparation of optically active propargylic alcohols", Tetrahedron (1998) 54(25): 7025-7032.
Singh et al., "Asymmetric Homologation of Boronic Esters Bearing Azido and Silyloxy Substituents", J Org Chem. (2000) 65(20):6650-6653 and Erratum: J Org Chem. (2001) 66(22):7560.
Singh et al., "Confronting the challenges of discovery of novel antibacterial agents", Bioorg Med Chem Lett. (2014) 24(16):3683-3689.
Sliwka et al., "Synthetic Sulfur Carotenoids II: Optically Active Carotenoid Thiols", Tetrahedron: Asymmetry (1993) 4(3):361-368.
Solladié et al., "First Stereocontrolled Synthesis of the (3S,5R,7R,10R,11R)-C1-C13 Fragment of Nystatin A(1)", J Org Chem. (1999) 64(15):5447-5452.
Souto et al., "Synthesis and biological characterization of the histone deacetylase inhibitor largazole and c7-modified analogues", J. Med. Chem. (2010) 53(12):4654-4667.
Spiegel et al., "CP-263,114 synthetic studies. Construction of an isotwistane ring system via rhodium carbenoid C—H insertion", Tetrahedron (2002) 58:6545-6554.
Sumida et al., "Boron-selective biaryl coupling approach to versatile dibenzoxaborins and application to concise synthesis of defucogilvocarcin M", Org Ltt. (Dec. 2014) 16(23):6240-6243.
Sun et al., "A method for the deprotection of alkylpinacolyl boronate esters", J Org Chem. (2011) 76(9): 3571-3575; Supporting Information, 8 pages.
Sun et al., "Programmed Synthesis of a Contiguous Stereotriad Motif by Triple Stereospecific Reagent-controlled Homologation", Org Lttr. (Jul. 2013) 15(17):4500-4503.
Tam et al., "Optimization of meropenem minimum concentration/MIC ratio to suppress in vitro resistance of Pseudomonas aeruginosa", Antimicrob Agents Chemother. (2005) 49(12):4920-4927.
Teo et al., "Efficient and highly aldehyde selective Wacker oxidation", Org Lett. (2012) 14(13):3237-3239.

(56) References Cited

OTHER PUBLICATIONS

Theuretzbacher et al., "Update on antibacterial and antifungal drugs—can we master the resistance crisis?", Curr Opin Pharmacol. (2011) 11:429-432.
Tobisu et al., "Nickel-catalyzed alkylative cross-coupling of anisoles with Grignard reagents via C—O bond activation". J Am Chem Soc. (2016) 138(47):6711 and Suppl. Information in 105 pages.
Ty et al., "Synthesis and biological evaluation of enantiomerically pure cyclopropyl analogues of combretastatin A4". Bioorg Med Chem (2013) 21:1357-1366.
U.S. Department of Health and Human Resources, "Antibiotic Resistance Threats in the United States, 2013"; 114 pages.
Valters et al., "Ring-Chain Tautomerism", Plenum Press, New York and London, Softcover reprint of the hardcover 1st Ed. 1985, Chapter 1, 23 pages.
VanScoy et al., "Pharmacokinetics-pharmacodynamics of tazobactam in 386 combination with ceftolozane in an in vitro infection model", Antimicrob Agents Chemother. (2013) 57: 2809-2814. doi: 10.1128/AAC.02513-12.
Vasil'Ev et al., (1977): STN International HCAPLUS database, Columbus (OH), accession No. 1977: 72730; 1 page.
Vitor et al., "Rhenium(I)- and technetium(I) tricarbonyl complexes anchored by bifunctional pyrazole-diamine and pyrazole-dithioether chelators", J Organometal Chem (2004) 689(25):4764-4774.
Voituriez et al., "Preparation of a storable zinc carbenoid species and its application in cyclopropanation, chain extension, and [2,3]-sigmatropic rearrangement reactions", J Org Chem. (2010) 75(4): 1244-1250; Supporting Information, 20 pages.
Waley, Stephen G., "A quick method for the determination of inhibition constants", Biochem J. (1982) 205(3):631-633.
Walker et al., "Pharmacodynamic activities of meropenem in an animal infection model", (1994), Abstracts of Papers #A91, 34th Interscience Conference on Antimicrobial Agents and Chemotherapy, Orlando, FL., 5 pages.
Walsh et al., "Metallo-beta-Lactamases: the Quiet before the Storm?", Clin Microbiol Rev. (2005) 18(2):306-325.
Wang et al., "Recognition and resistance in TEM beta-lactamase", Biochemistry (2003) 42(28):8434-8444.
Webb et al., "Metal catalysed hydroboration of vinyl sulfides, sulfoxides, sulfones, and sulfonates", J Mol Cat A: Chem. (2007) 275:91-100.
Wenkert et al., "Nickel-induced conversion of carbon-oxygen into carbon-carbon bonds. One-step transformations of enol ethers into olefins and aryl ethers into biaryls".(1979) 101(8):2246-2247.
Wilson D.N., "The A-Z of bacterial translation inhibitors", Crit Rev Biochem Mol Biolog. (2009) 44(6):393-433.
Wohlrab et al., "Total synthesis of plusbacin A3: a depsipeptide antibiotic active against vancomycin-resistant bacteria", J. Am. Chem. Soc. (2007) 129:4175-4177.
Wong et al., "A chemoselective Reformatsky-Negishi approach to α-haloaryl esters", Tetrahedron (2014) 70(7): 1508-1515.
Xia et al., "Synthesis and SAR of novel benzoxaboroles as a new class of beta-lactamase inhibitors", Bioorg Med Chem Lett. (2011) 21:2533-2536.
Xie et al., "Group-assisted purification (GAP) chemistry for the synthesis of Velcade via asymmetric borylation of N-phosphinylimines", Beilstein J Org Chem (Mar. 2014) 10:746-751.
Yamamoto et al., "Iridium-catalyzed hydroboration of alkenes with pinacolborane", Tetrahedron (2004) 60:10695-10700.
Yanagisawa et al., "Nonpeptide angiotensin II receptor antagonists: synthesis, biological activities, and structure-activity relationships of imidazole-5-carboxylic acids bearing alkyl, alkenyl, and hydroxyalkyl substituents at the 4-position and their related compounds", J Med Chem. (1996) 39(1):323-338.
Yuen et al., "Deprotection of pinacolyl boronate esters via hydrolysis of intermediate potassium trifluoroborates", Tetrahed Lttr. (2005) 46(46):7899-7903.
Zhu et al., "Design, preparation, x-ray crystal structure, and reactivity of o-alkoxyphenyliodonium bis(methoxycarbonyl)methanide, a highly soluble carbene precursor", Org Lett. (2012) 14(12): 3170-3173; Supporting Information, 76 pages.
CAS Registry No. 2114651-20-4; "7-Benzofurancarboxylic acid", Aurora Fine Chemicals; Aug. 16, 2017; 1 page.
CAS Registry No. 1780853-40-8; "7-Benzofurancarboxylic acid", Aurora Fine Chemicals; Jun. 15, 2015; 1 page.
CAS Registry No. 1427326-65-5; "7-Benzofurancarboxylic acid", Ellanova Laboratories; Apr. 5, 2013; 1 page.
CAS Registry No. 1344904-36-4; "7-Benzofurancarboxylic acid", Asiba Pharmatech, Inc.; Nov. 13, 2011; 1 page.
CAS Registry No. 1890373-92-8; "Benzoic acid", Aurora Fine Chemicals; Apr. 15, 2016; 1 page.
Cheng et al., "Inhibitors of hepatitis C virus polymerase: Synthesis and characterization of novel 2-oxy-6-fluoro-N-((S)-1-hydroxy-3-phenylpropan-2-yl)-benzamides", Bioorg Med Chem Ltts. (2010) 20:2119-2124.
International Search Report and Written Opinion dated Jan. 16, 2019 for International Application No. PCT/US2018/055240, filed Oct. 10, 2018.

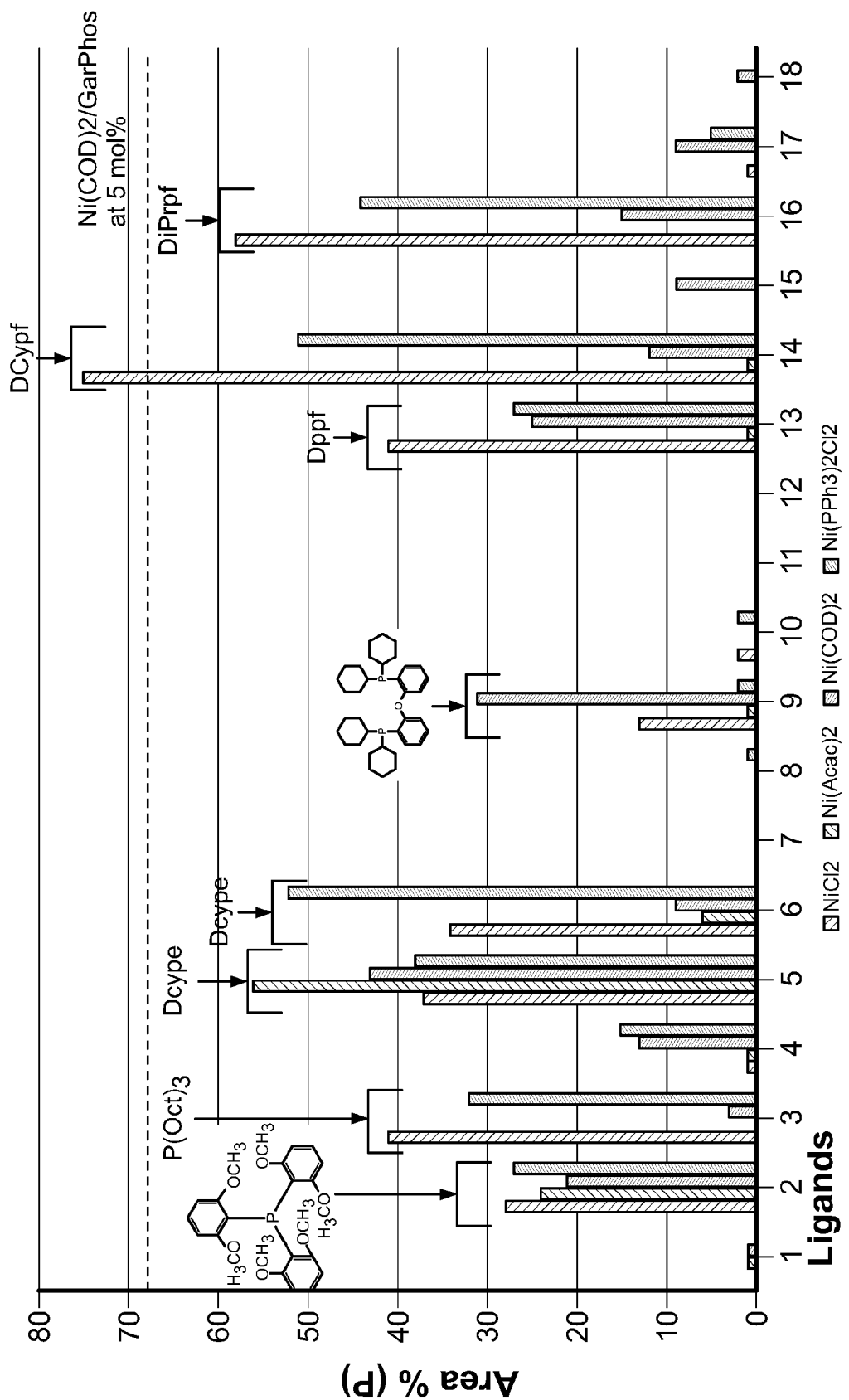

BORONIC ACID DERIVATIVES AND SYNTHESIS THEREOF

INCORPORATION BY REFERENCE TO ANY PRIORITY APPLICATIONS

This application claims the benefit of U.S. Provisional Application No. 62/571,149, entitled Boronic Acid Derivatives and Synthesis Thereof, filed Oct. 11, 2017, the disclosure of which is incorporated herein by reference in its entirety.

STATEMENT REGARDING FEDERALLY SPONSORED R&D

This invention was made with government support under Grant Number HHS0100201600026C, awarded by Department of Health and Human Services. The government has certain rights in the invention.

BACKGROUND

Field

The present application relates to the fields of chemistry and medicine. More particularly, the present application relates to boronic acid antimicrobial compounds, compositions, their preparation, and their use as therapeutic agents.

Description of the Related Art

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of anti-bacterial therapy. The increase in antibiotic resistant strains has been particularly common in major hospitals and care centers. The consequences of the increase in resistant strains include higher morbidity and mortality, longer patient hospitalization, and an increase in treatment costs.

Various bacteria have evolved β-lactam deactivating enzymes, namely, β-lactamases, that counter the efficacy of the various β-lactam antibiotics. β-lactamases can be grouped into 4 classes based on their amino acid sequences, namely, Ambler classes A, B, C, and D. Enzymes in classes A, C, and D include active-site serine β-lactamases, and class B enzymes, which are encountered less frequently, are Zn-dependent. These enzymes catalyze the chemical degradation of β-lactam antibiotics, rendering them inactive. Some β-lactamases can be transferred within and between various bacterial strains and species. The rapid spread of bacterial resistance and the evolution of multi-resistant strains severely limits β-lactam treatment options available.

The increase of class D β-lactamase-expressing bacterium strains such as *Acinetobacter baumannii* has become an emerging multidrug-resistant threat. *A. baumannii* strains express A, C, and D class β-lactamases. The class D β-lactamases such as the OXA families are particularly effective at destroying carbapenem type β-lactam antibiotics, e.g., imipenem, the active carbapenems component of Merck's Primaxin® (Montefour, K. et al., Crit. Care Nurse 2008, 28, 15; Perez, F. et al., Expert Rev. Anti Infect. Ther. 2008, 6, 269; Bou, G.; Martinez-Beltran, J., Antimicrob. Agents Chemother. 2000, 40, 428. 2006, 50, 2280; Bou, G. et al., J. Antimicrob. Agents Chemother. 2000, 44, 1556). This has imposed a pressing threat to the effective use of drugs in that category to treat and prevent bacterial infections. Indeed the number of catalogued serine-based β-lactamases has exploded from less than ten in the 1970s to over 300 variants. These issues fostered the development of five "generations" of cephalosporins. When initially released into clinical practice, extended-spectrum cephalosporins resisted hydrolysis by the prevalent class A β-lactamases, TEM-1 and SHV-1. However, the development of resistant strains by the evolution of single amino acid substitutions in TEM-1 and SHV-1 resulted in the emergence of the extended-spectrum β-lactamase (ESBL) phenotype.

New β-lactamases have recently evolved that hydrolyze the carbapenem class of antimicrobials, including imipenem, biapenem, doripenem, meropenem, and ertapenem, as well as other β-lactam antibiotics. These carbapenemases belong to molecular classes A, B, and D. Class A carbapenemases of the KPC-type predominantly in *Klebsiella pneumoniae* but now also reported in other Enterobacteriaceae, *Pseudomonas aeruginosa* and *Acinetobacter baumannii*. The KPC carbapenemase was first described in 1996 in North Carolina, but since then has disseminated widely in the US. It has been particularly problematic in the New York City area, where several reports of spread within major hospitals and patient morbidity have been reported. These enzymes have also been recently reported in France, Greece, Sweden, United Kingdom, and an outbreak in Germany has recently been reported. Treatment of resistant strains with carbapenems can be associated with poor outcomes.

The zinc-dependent class B metallo-β-lactamases are represented mainly by the VIM, IMP, and NDM types. IMP and VIM-producing *K. pneumonia* were first observed in 1990s in Japan and 2001 in Southern Europe, respectively. IMP-positive strains remain frequent in Japan and have also caused hospital outbreaks in China and Australia. However, dissemination of IMP-producing Enterobacteriaceae in the rest of the word appears to be somewhat limited. VIM-producing enterobacteria can be frequently isolated in Mediterranean countries, reaching epidemic proportions in Greece. Isolation of VIM-producing strains remains low in Northern Europe and in the United States. In stark contrast, a characteristic of NDM-producing *K. pneumonia* isolates has been their rapid dissemination from their epicenter, the Indian subcontinent, to Western Europe, North America, Australia and Far East. Moreover, NDM genes have spread rapidly to various species other than *K. pneumonia*.

The plasmid-expressed class D carbapenemases belong to OXA-48 type. OXA-48 producing *K. pneumonia* was first detected in Turkey, in 2001. The Middle East and North Africa remain the main centers of infection. However, recent isolation of OXA-48-type producing organisms in India, Senegal and Argentina suggest the possibility of a global expansion. Isolation of OXA-48 in bacteria other than *K. pneumonia* underlines the spreading potential of OXA-48.

Treatment of strains producing any of these carbapenemases with carbapenems can be associated with poor outcomes.

Another mechanism of β-lactamase mediated resistance to carbapenems involves combination of permeability or efflux mechanisms combined with hyper production of beta-lactamases. One example is the loss of a porin combined in hyperproduction of ampC beta-lactamase results in resistance to imipenem in *Pseudomonas aeruginosa*. Efflux pump over expression combined with hyperproduction of the ampC β-lactamase can also result in resistance to a carbapenem such as meropenem.

Thus, there is a need for efficient method of synthesizing β-lactamase inhibitors (BLIs).

SUMMARY OF THE INVENTION

One embodiment relates to a method of making a compound of formula (I) or pharmaceutically acceptable salt thereof Formula (I)

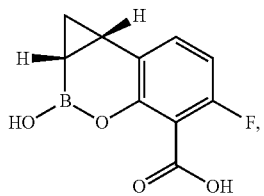

the method comprising the steps of: reacting a compound of formula (A-I)

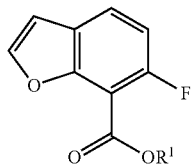

with a borylating agent to form an organoboron intermediate; converting the organoboron intermediate to a compound of Formula (A-III)

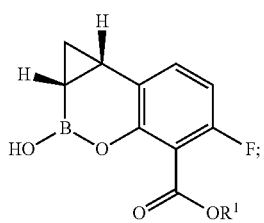

and hydrolyzing the compound of Formula (A-III) to form the compound of Formula (I), wherein $R^1$ is a carboxylic acid protecting group. In some embodiments, $R^1$ is $C_{1-6}$ alkyl.

Some embodiments relate to a method of making a compound of Formula (A-III) or pharmaceutically acceptable salt thereof, Formula (A-III)

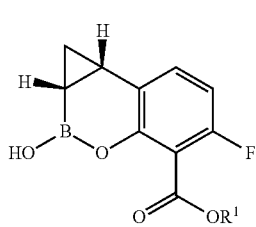 [SMILES: O=C(O)c1c(F)ccc2c1OB(O)[C@@H]1C[C@H]21]

comprising the steps of:
reacting a compound of formula (A-I)

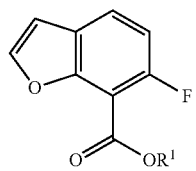

with a borylating agent to form an organoboron intermediate;
converting the organoboron intermediate to a compound of Formula (A-III);
wherein:
$R^1$ is a carboxylic acid protecting group.

Some embodiments relate to a method of making a compound of formula (I)

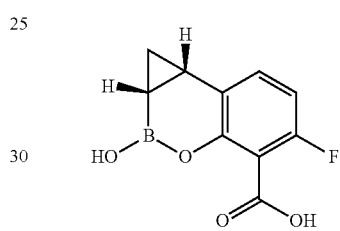

or pharmaceutically acceptable salt thereof, comprising the steps of: converting a compound of formula (A-II)

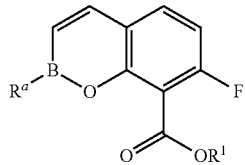

to a compound of Formula (A-III)

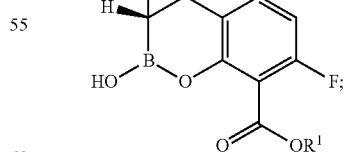

and hydrolyzing the compound of Formula (A-III) to form the compound of Formula (I).

Some embodiments relate to a method of making a compound of formula (I) or pharmaceutically acceptable salt thereof,

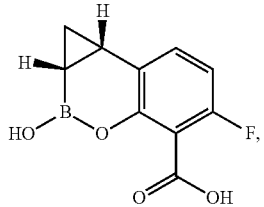

Formula (I)

comprising the steps of: combining a compound of formula (A-II)

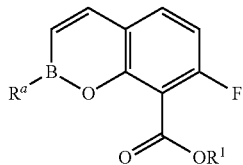

and one or more chiral auxiliaries to form a chiral complex, reacting the chiral complex with a cyclopropylating agent to form a compound of formula (III)

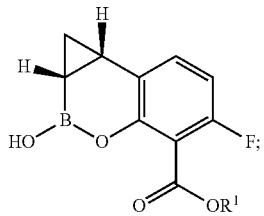

and hydrolyzing the compound of Formula (A-III) to form the compound of Formula (I).

In some embodiments, the converting of the organoboron intermediate comprises reacting the organoboron intermediate with a cyclopropylating agent.

In some embodiments, the converting of the organoboron intermediate comprises combining the organoboron intermediate and one or more chiral auxiliaries to form a chiral complex and reacting the chiral complex with a cyclopropylating agent.

Some embodiments relate to a method of making a compound of formula (A-II), comprising the steps of reacting a compound of formula (A-I) with a borylating agent to form the compound of formula (A-II).

Some embodiments relate to a method of preparing a compound of Formula (A-I)

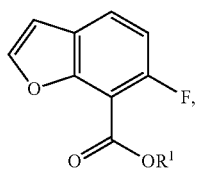

the method comprising the steps of: reacting a compound of formula (A-V)

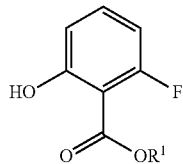

with an alkylating agent to form a compound of formula (A-VI)

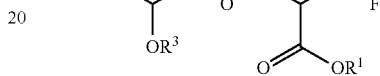

(A-VI); and converting the compound of formula (A-VI) to the compound of formula (A-I). Some embodiments relate to a method of preparing a compound of Formula (A-I), comprising the steps of: reacting a compound of formula (A-V)

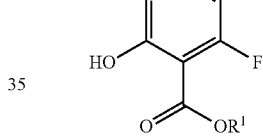

with an alkylating agent to form a compound of formula (A-VI')

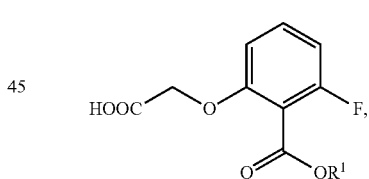

and converting the compound of formula (A-VI') to a compound of formula (A-I), wherein $R^1$ is a carboxylic acid protecting group.

Some embodiments relate to a method of preparing a compound of Formula (A-I'), comprising the steps of:

Formula (A-I')

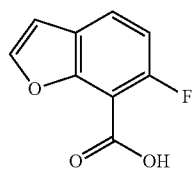

reacting a compound of formula (A-V)

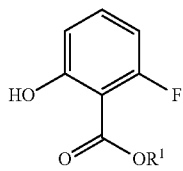

with an alkylating agent to form a compound of formula (A-VI')

(A-VI')

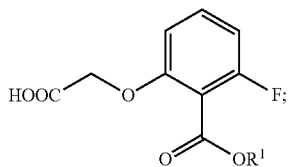

converting the compound of formula (A-VI') to a compound of formula (A-I), and
hydrolyzing the compound of Formula (A-I) to form the compound of Formula (A-I'),
wherein:
$R^1$ is a carboxylic acid protecting group. In some embodiments, $R^1$ is $C_{1-6}$ alkyl.

In some embodiments, the hydrolyzing of the compound of formula (A-III) is performed using a base. In some embodiments, the base is NaOH.

Some embodiments relate to a method of preparing a compound of formula (A-IV)

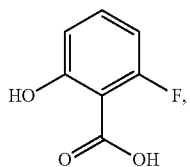

comprising hydrolyzing

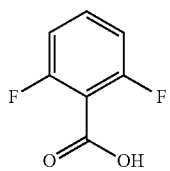

with a base to form the compound of formula (A-IV).
In some embodiments, the hydrolyzing of

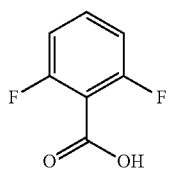

is performed at a high temperature. In some embodiments, the hydrolyzing step is performed at about 145° C. In some embodiments, the base is NaOH.

Some embodiments relate to a compound having the structure of

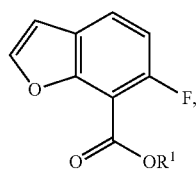

wherein $R^1$ is a carboxylic acid protecting group. Some embodiments relate to a compound having the structure of

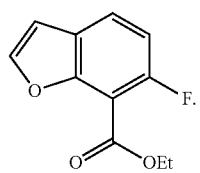

Some embodiments relate to a compound having the structure of

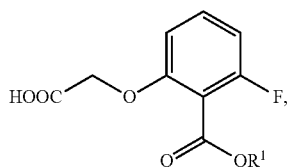

wherein $R^1$ is a carboxylic acid protecting group. Some embodiments relate to a compound having the structure of

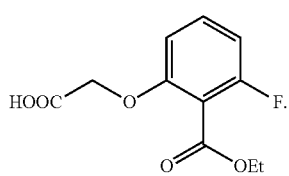

Some embodiments relate to a compound having the structure of

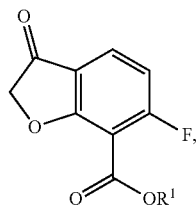

wherein R¹ is a carboxylic acid protecting group. Some embodiments relate to a compound having the structure of

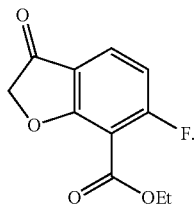 [SMILES: CCOC(=O)c1c(F)ccc2c1OCC2=O]

Some embodiments relate to a compound having the structure of

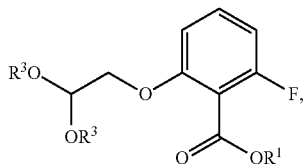

wherein R¹ is a carboxylic acid protecting group, and each R³ is optionally substituted $C_{1-6}$alkyl, or two R³ together are an optionally substituted $C_{2-4}$ alkylene chain and together with the intervening atoms form an optionally substituted 5-7 membered heterocyclyl ring.

Some embodiments relate to a compound having the structure of

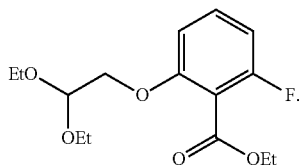 [SMILES: CCOC(=O)c1c(F)cccc1OCC(OCC)OCC]

Some embodiments relate to a compound having the structure of

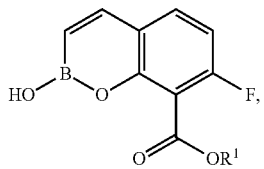

wherein R¹ is a carboxylic acid protecting group.

Some embodiments relate to a compound having the structure of

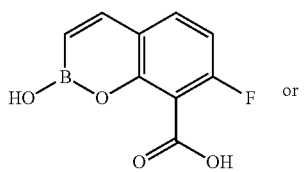

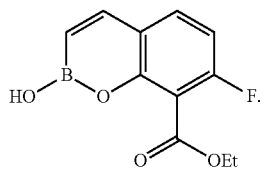

Some embodiments relate to a compound having the structure of

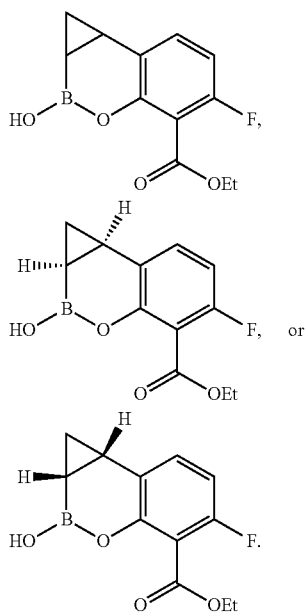

Some embodiments relate to a compound having the structure of

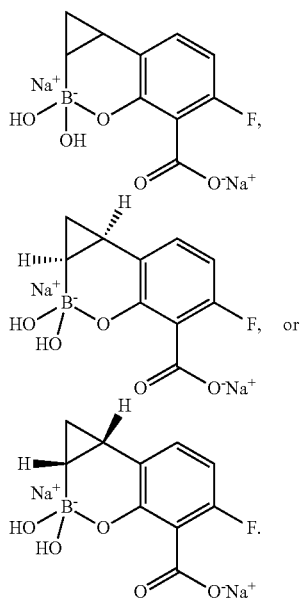

Some embodiments relate to a compound having the structure of

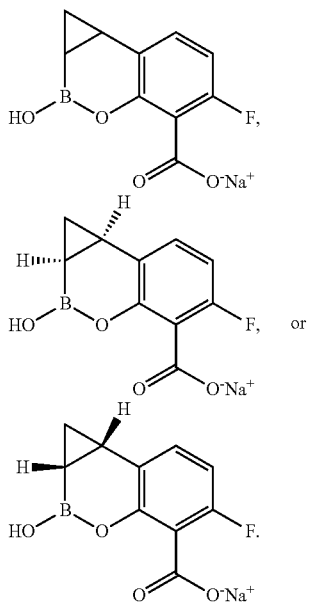

BRIEF DESCRIPTION OF THE DRAWINGS

FIG. 1 is a graph showing the reaction yield of the borylating step using various catalyst combinations.

DETAILED DESCRIPTION OF EMBODIMENTS

Compound A and pharmaceutically acceptable salts thereof are described in International Application PCT/US2017/039787, which is incorporated herein by reference in its entirety. Compound A is a β-lactamase inhibitor effective in treating bacterial infections when used in combination with β-lactam antibiotics.

Compound A

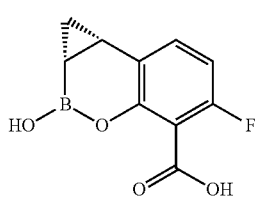

The synthesis of a compound of formula (I), including compound A and pharmaceutically acceptable salts thereof (e.g., sodium salts), and the reaction intermediates involved in the preparation are described in some embodiments. The synthesis methods described herein can achieve high yield and high enantioselectivity, which leads to easy isolation and high purity of the target enantiomeric isomer (e.g., compound A and pharmaceutically acceptable salts thereof). The preparation method described herein can achieve high yield and high enantiomeric excess (e.e.) for the compound of formula (I) (e.g., compound A). The reaction agents used in the preparation method can produce the compound of formula (I) in a cost-efficient manner and is advantages for application in large scale synthesis.

Some embodiments relate to a method of making a compound of formula (I) (Compound A), or pharmaceutically acceptable salt thereof, comprising the steps of:

Formula (I)

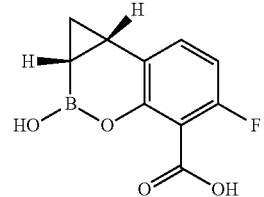

reacting a compound of formula (A-I)

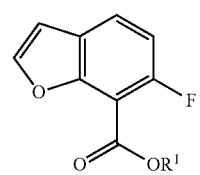

with a borylating agent to form an organoboron intermediate;

converting the organoboron intermediate to a compound of Formula (A-III)

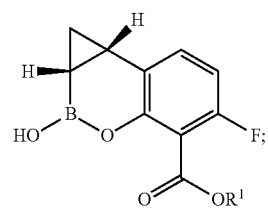

and hydrolyzing the compound of Formula (A-III) to form the compound of Formula (I), wherein:

$R^1$ is a carboxylic acid protecting group.

Some embodiments relate to a method of making a compound of formula (I) or pharmaceutically acceptable salt thereof, comprising the steps of:

converting a compound of formula (A-II)

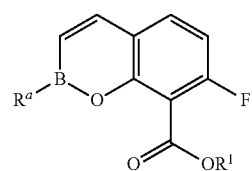

to a compound of Formula (A-III)

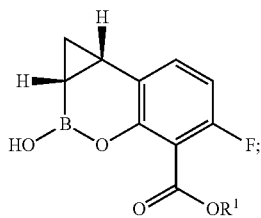

and
hydrolyzing the compound of Formula (A-III) to form the compound of Formula (I),
wherein:
$R^1$ is a carboxylic acid protecting group; and
$R^a$ is OH or optionally substituted —O—$C_{1-6}$ alkyl.

In some embodiments, the method of making a compound of formula (I) or pharmaceutically acceptable salt thereof further comprising the steps of:
combining a compound of formula (A-II)

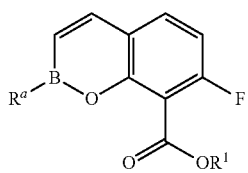

and one or more chiral auxiliaries to form a chiral complex having a formula of (A-II')

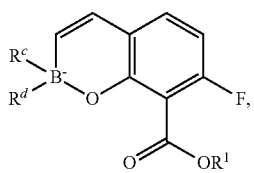

reacting the chiral complex with a cyclopropylating agent to form a compound of formula (III)

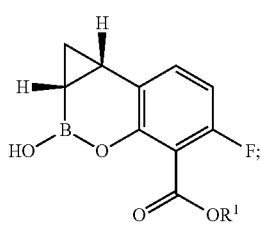

and
hydrolyzing the compound of Formula (A-III) to form the compound of Formula (I),
wherein:
$R^1$ is a carboxylic acid protecting group,
$R^a$ is OH or optionally substituted —O—$C_{1-6}$ alkyl, and
$R^c$ and $R^d$ with any intervening atoms form an optionally substituted 4-7 membered heterocyclyl ring.

Some embodiments relate to a method of making a compound of formula (A-II), comprising the steps of: reacting a compound of formula (A-I) with a borylating agent to form the compound of formula (A-II).

Some embodiments relate to a method of preparing a compound of Formula (A-M), comprising the steps of:
combining a compound of formula (A-II)

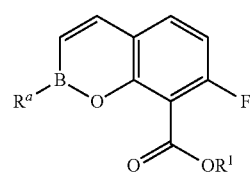

and one or more chiral auxiliaries to form a chiral complex, and
reacting the chiral complex with a cyclopropylating agent to form a compound of formula (III)

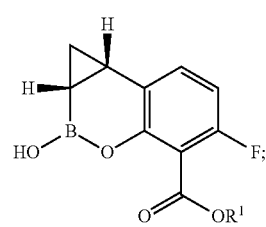

wherein:
$R^1$ is a carboxylic acid protecting group, and
$R^a$ is OH or optionally substituted —O—$C_{1-6}$ alkyl.

Some embodiments relate to a method of preparing a compound of Formula (A-I'),
comprising the steps of:

Formula (A-I')

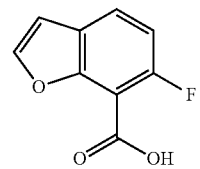

reacting a compound of formula (A-V)

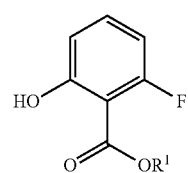

with an alkylating agent to form a compound of formula (A-VI')

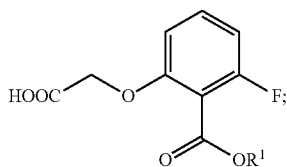
(A-VI')

converting the compound of formula (A-VI') to a compound of formula (A-I), and reducing and hydrolyzing the compound of Formula (A-I) to form the compound of Formula (A-I'), wherein $R^1$ is a carboxylic acid protecting group.

For the compound of Formula (I), (A-I), (A-II), (A-II'), (A-III), (A-IV), (A-V), (A-VI) and (A-VII'), $R^1$ is a carboxylic acid protecting group. In some embodiments, $R^1$ is optionally substituted $C_{1-6}$ alkyl, optionally substituted $C_{3-7}$ carbocyclyl, optionally substituted 3-10 membered heterocyclyl, optionally substituted $C_{6-10}$ aryl, or optionally substituted 5-10 membered heteroaryl. In some embodiments, $R^1$ is $C_{1-6}$ alkyl. In some embodiments, $R^1$ is ethyl. In some embodiments, $R^1$ is methyl. In some embodiments, $R^1$ is optionally substituted $C_{1-6}$ alkyl.

The borylating agent can be any borylating agent suitable for introducing the boron atom into a furan ring. In some embodiments, the borylating agent is $(R^2O)_2B$—$B(OR^2)_2$, wherein each $R^2$ is independently H, optionally substituted $C_{1-6}$alkyl, or two $R^2$ together are an optionally substituted $C_{2-4}$ alkylene chain and form an optionally substituted 5-7 membered heterocyclyl ring with the intervening atoms. In some embodiments, the borylating agent is $(HO)_2B$—$B(OH)_2$. In some embodiments, the borylating agent is selected from the group consisting of $B_2(Pin)_2$ (Bis(pinacolato)diboron), $B_2(Cat)_2$ (Bis(catecholato)diboron), and $B_2neop_2$ (Bis(neopentyl glycolato)diboron). In some embodiments, the borylating agent is $B_2(Pin)_2$.

In some embodiments, $R^3$ is optionally substituted $C_{1-6}$alkyl, or two $R^3$ together are an optionally substituted $C_{2-4}$ alkylene chain and together with the intervening atoms form an optionally substituted 5-7 membered heterocyclyl ring. In some embodiments, each $R^3$ is independently an optionally substituted $C_{1-6}$ alkyl, or two $R^3$ together are optionally-substituted $C_{2-3}$ alkylene and form an optionally substituted 5-6 membered heterocyclyl ring with intervening atoms. In some embodiments, $R^3$ is a $C_{1-6}$ alkyl. In some embodiments, $R^3$ is ethyl. In some embodiments, $R^3$ is methyl. In some embodiments, $R^3$ is a $C_{1-6}$ alkyl optionally substituted with one or more $C_{1-4}$ alkyl. In some embodiments, two $R^3$ together with the intervening atoms can form an optionally substituted 5-6 membered heterocyclyl ring. In some embodiments, two $R^3$ together with the intervening atoms can form an optionally substituted 5-6 membered heterocyclyl ring and two $R^3$ form a $C_{2-3}$ alkylene chain. In some embodiments, the optionally substituted 5-6 membered heterocyclyl ring contains one or more oxygen atoms.

In some embodiments, $R^a$ is OH. In some embodiments, $R^a$ is optionally substituted —O—$C_{1-6}$ alkyl. In some embodiments, $R^a$ is O-methyl. In some embodiments, $R^a$ is O-ethyl.

In some embodiments, $R^c$ and $R^d$ with any intervening atoms form an optionally substituted 4-7 membered heterocyclyl ring. In some embodiments, $R^c$ and $R^d$ with any intervening atoms form an optionally substituted oxazaborolidine. In some embodiments, $R^c$ and $R^d$ with any intervening atoms form an optionally substituted 4-7 membered heterocyclyl ring containing one or more O, S, N, or B atoms. In some embodiments, $R^c$ and $R^d$ with any intervening atoms form an optionally substituted 4-7 membered heterocyclyl ring containing B, N, and O atoms. In some embodiments, the heterocyclyl ring is optionally substituted with one or more substituents selected from $C_{1-4}$ alkyl, $C_{6-10}$ aryl, OH, and —$OC_{1-4}$ alkyl. In some embodiments, the heterocyclyl ring is optionally substituted with one or more substituents selected from $C_{1-4}$ alkyl, $C_{6-10}$ aryl, OH, oxo, COOH, and —$OC_{1-4}$ alkyl. In some embodiments, the heterocyclyl ring is optionally substituted with one or more substituents selected from $C_{1-4}$ alkyl and $C_{6-10}$ aryl.

In some embodiments, the compound of formula (A-I) is

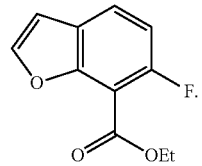

In some embodiments, the compound of formula (A-II) is

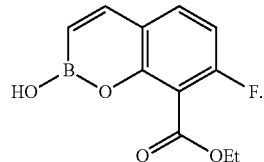

In some embodiments, the compound of formula (A-III) is

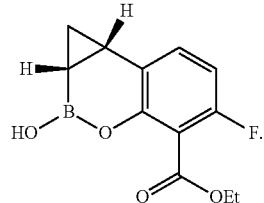 [SMILES: CCOC(=O)c1c(F)ccc2c1OB(O)[C@@H]1C[C@H]21]

In some embodiments, the compound of formula (I) is

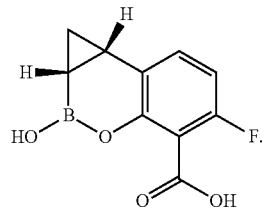 [SMILES: O=C(O)c1c(F)ccc2c1OB(O)[C@@H]1C[C@H]21]

In some embodiments, the alkylating agent is $CH(OR^3)_2CH_2X$ and X is a halogen. In some embodiments, the alkylating agent is $CH(OEt)_2CH_2Br$. In some embodiments, X is Cl. In some embodiments, X is Br.

In some embodiments, for the preparation of the compound of formula (A-I) and (A-I'), the alkylating agent is R⁴OOCCH₂X wherein $R^4$ is an optionally substituted $C_{1-6}$ alkyl and X is a halogen. In some embodiments, the alkylating agent is MeOOCCH₂Cl. In some embodiments, $R^4$ is a $C_{1-6}$ alkyl. In some embodiments, $R^4$ is methyl. In some embodiments, X is Cl. In some embodiments, X is Br.

In some embodiments, the method of preparing a compound of formula (A-I) or (A-I') further comprises protecting the carboxylic acid in a compound of formula (A-IV)

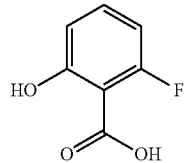

to form the compound of formula (A-V).

In some embodiments, the compound of formula (A-IV) is

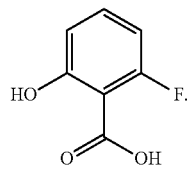

In some embodiments, the compound of formula (A-V) is

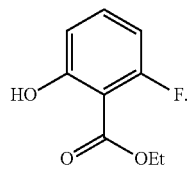

In some embodiments, the compound of formula (A-VI) is

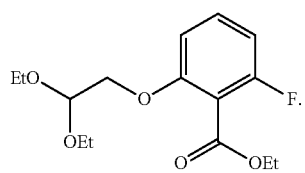

In some embodiments, the method of preparing the compound of formula (A-I') further comprises converting

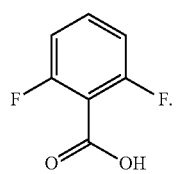

to a compound of formula (A-IV)

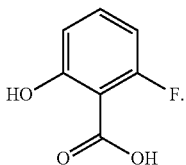

In some embodiments, the compound of formula (A-VI') is

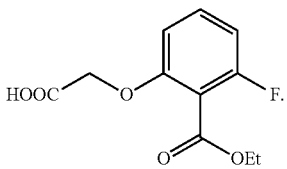

In some embodiments, the conversion of the compound of formula (A-VI') to the compound of formula (A-I) further comprises converting the compound of formula (A-VI') to a compound of formula (A-VII')

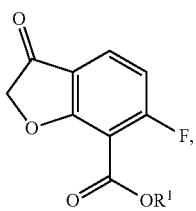

and then reducing and dehydrating the compound of formula (A-VII') to form the compound of formula (A-I).

In some embodiments, the compound of formula (A-VII') is

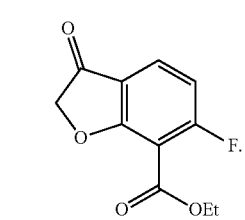 [SMILES: CCOC(=O)c1c(F)ccc2c1OCC2=O]

In some embodiments, the reaction of the compound of formula (A-I) and the borylating agent is performed in the presence of a first catalyst. In some embodiments, the first catalyst comprises one or more Ni catalyst precursors and one or more ligands. In some embodiments, the first catalyst is formed by combining a nickel catalyst precursor and one or more ligands. In some embodiments, the first catalyst is formed by combining a nickel catalyst precursor and one or more ligands in an organic solvent (e.g., toluene, xylene, or THF).

In some embodiments, Ni catalyst precursor is selected from the group consisting of NiCl₂, Ni(Acac)₂, Ni(COD)₂, NiCl₂(PPh₃)₂, NiCl₂(PCy₂Ph)₂, NiC₂(PPh₂CH₂CH₂PPh₂), NiC₂(1,3-Bis(diphenylphosphino)propane), and NiCl₂(1,3-

Bis(diphenylphosphino)ethane). In some embodiments, the Ni catalyst precursor is $NiCl_2$ or $Ni(Acac)_2$. In some embodiments, the Ni catalyst precursor is $NiCl_2$.

In some embodiments, the ligand is monodentate or bidentate. In some embodiments, the ligand is selected from the group consisting of aliphatic, aromatic, NHC ligands, phosphites, phosphoramidites, and amines. In some embodiments, the ligand is selected from the group consisting of NHC ligands, phosphines, phosphites, phosphoramidites, amines, alcohol, aminoalcohol, and a combination thereof. In some embodiments, the ligand is an amine optionally substituted with aryl, alkyl, and/or heteroaryl groups. In some embodiments, the ligand is NHC ligand. In some embodiments, the ligand is phosphines. In some embodiments, the ligand is phosphites. In some embodiments, the ligand is phosphoramidites. In some embodiments, the ligand is amine. In some embodiments, the ligand is alcohol. In some embodiments, the ligand is aminoalcohol. In some embodiments, the ligand or catalyst is selected from the group consisting of Bis(di-cyclopentylphosphnium)ethyl tetrafluoroborate, 4,5-Bis(di-tert-butylphosphino)-9,9-dimethylxanthene, 2,2'-bis(dicyclohexylphosphaneyl)-1,1'-biphenyl, 1,2-bis((di-tert-butylphosphaneyl)methyl)benzene, 1,3-Bis(1-adamanthyl)imidazolium, 1,3-Di-tert-butylimidazolium, 1,3-Bis(2,6-diisopropyl-phenyl)-4,5-dihydroimidazol-2-ylidene, 1,3-bis(2,6-diisopropylphenyl)-1H-imidazol-3-ium-2-ide, $P(Octyl)_3$, Dppf, DiPrf, dcype, JosiPhos 9-1, (S,S,R,R)-TangPhos,(S,S,R,R)-DuanPhos, DavePhos, $P(tBu)_3$, XantPhos, (tBu)XantPhos, (R)-SegPhos, (R)-DM-SegPhos, (R)-MeOBIPHEP, (R,S)-BinaPhos, Binaphane, Phosphoramidite, $(S)-SegphosRu(Oac)_2$, $trans-PdCl_2(Pcy_3)_2$, [Rh(S,S)EtDuPhos(COD)]Otf, (S)-XylylPhanePhos, (R)—C3-TunePhos, (R)-DTBM-Garphos, (R)-DMM-Garphos, (R,R,R)-Xyl-SKP, Thio-XantPhos, TaniaPhos, SPANPhos, tris(4-methoxyphenyl)phosphine, Tris(2,6-dimethoxyphenyl) phosphine, Trioctylphosphine, Bis(dicyclohexylphosphino) methane), DCYPE, 1,3-Bis(dicyclohexyl phosphino)propane, 1,2-Bis(diphenylphosphino)ethane, (R,R)-Dipamp, Bis(dicyclohexyl phosphinophenyl) ether, DPEPhos, Bis(2-diphenylphosphinoethyl) Phenylphosphine, 1,1,1-Tris(diphenyl phosphinomethyl)ethane, DPPF, 1,1'-Ferrocenediyl-bis(dicyclohexylphosphine), DTBPF, DiPrF, 1-Diphenylphosphino-1'-(di-butylphosphino)ferrocene, HiersoPhos, iPr(NHC), SIMes, IMes, and (1,3-bis[bis(o-methoxyphenyl)phosphino]propane. In some embodiments, the ligand is $P(Octyl)_3$, diPrf, or dcype.

In some embodiments, the ligand is selected from the group consisting of Bis(di-cyclopentylphosphnium)ethyl tetrafluoroborate, 4,5-Bis(di-tert-butylphosphino)-9,9-dimethylxanthene, 2,2'-bis(dicyclohexylphosphaneyl)-1,1'-biphenyl, 1,2-bis((di-tert-butylphosphaneyl)methyl)benzene, 1,3-Bis(1-adamanthyl)imidazolium, 1,3-Di-tert-butylimidazolium, 1,3-Bis(2,6-diisopropyl-phenyl)-4,5-dihydroimidazol-2-ylidene, 1,3-bis(2,6-diisopropylphenyl)-1H-imidazol-3-ium-2-ide, $P(Octyl)_3$, Dppf, DiPrf, dcype, JosiPhos 9-1, (S,S,R,R)-TangPhos,(S,S,R,R)-DuanPhos, DavePhos, $P(tBu)_3$, XantPhos, (tBu)XantPhos, (R)-SegPhos, (R)-DM-SegPhos, (R)-MeOBIPHEP, (R,S)-BinaPhos, Binaphane, Phosphoramidite, (S)-XylylPhanePhos, (R)-C3-TunePhos, (R)-DTBM-Garphos, (R)-DMM-Garphos, (R,R,R)-Xyl-SKP, Thio-XantPhos, TaniaPhos, SPANPhos, tris(4-methoxyphenyl)phosphine, Tris(2,6-dimethoxyphenyl) phosphine, Trioctylphosphine, Bis(dicyclohexylphosphino) methane), DCYPE, 1,3-Bis(dicyclohexyl phosphino)propane, 1,2-Bis(diphenylphosphino)ethane, (R,R)-Dipamp, Bis(dicyclohexyl phosphinophenyl) ether, DPEPhos, Bis(2-diphenylphosphinoethyl) Phenylphosphine, 1,1,1-Tris(diphenyl phosphinomethyl)ethane, DPPF, 1,1'-Ferrocenediyl-bis(dicyclohexylphosphine),DTBPF,DiPrF,1-Diphenylphosphino-1'-(di-butylphosphino)ferrocene, HiersoPhos, iPr(NHC), SIMes, IMes, and (1,3-bis[bis(o-methoxyphenyl)phosphino]propane. In some embodiments, the ligand is $P(Octyl)_3$, diPrf, or dcype.

In some embodiments, the amount of Ni catalyst precursor is in the range of about 5 mol % to about 25 mol % of the compound of formula (A-I). In some embodiments, the amount of Ni catalyst precursor is about 5 mol %, 10 mol %, 15 mol %, 20 mol %, 25 mol %, 30 mol %, 40 mol %, 50 mol % of the compound of formula (A-I). In some embodiments, the amount of Ni catalyst precursor is greater than about 1 mol %, 5 mol %, 10 mol %, 15 mol %, 20 mol %, 25 mol %, 30 mol %, 40 mol %, 50 mol % of the compound of formula (A-I). In some embodiments, the amount of Ni catalyst precursor is less than about 5 mol %, 10 mol %, 15 mol %, 20 mol %, 25 mol %, 30 mol %, 40 mol %, 50 mol % of the compound of formula (A-I). In some embodiments, the amount of Ni catalyst precursor is in the range of about 1 mol % to about 20 mol %, about 1 mol % to about 30 mol %, about 5 mol % to about 20 mol %, about 5 mol % to 30 mol %, about 5 mol % to about 40 mol %, about 5 mol % to about 50 mol % of the compound of formula (A-I).

The ratio of the ligand to the Ni catalyst precursor can depend on the types of precursor and ligand used. In some embodiments, the ratio of the ligand to the Ni catalyst precursor can be in the range of about 0.5 to about 5. In some embodiments, the ratio of the ligand to the Ni catalyst precursor can be about 0.5, 1, 1.5, 2, 2.5, or 5. In some embodiments, the ratio of the ligand to the Ni catalyst precursor can be in the range of about 0.1-10, 0.5-5, 0.5-3, 0.5-2.5, 1-2, 1-3, 1-4, 1-5, or 1-2.5. In some embodiments, the ratio of the ligand to the Ni catalyst precursor can be greater than about 0.1, 0.5, 1, 1.25, 1.5, 1.75, 2, 3, 4, 5, 6, or 10. In some embodiments, the ratio of the ligand to the Ni catalyst precursor can be less than 0.5, 1, 1.25, 1.5, 1.75, 2, 3, 4, 5, 6, 10, or 20.

In some embodiments, the reaction of the compound of formula (A-I) and the borylating agent is performed in the presence of a base system. In some embodiments, the base system comprises one or more inorganic bases. In some embodiments, the base system comprises $K_2CO_3$, $Cs_2CO_3$, $Li_2CO_3$, or any combination thereof.

In some embodiments, the base system comprises a mixture of $K_2CO_3$ and $Cs_2CO_3$, wherein the molar ratio of $K_2CO_3$ and $Cs_2CO_3$ is in the range of about 5:1 to 15:1. In some embodiments, the base system comprises a mixture of $K_2CO_3$ and $Cs_2CO_3$, wherein the molar ratio of $K_2CO_3$ and $Cs_2CO_3$ is about 9:1.

In some embodiments, the reaction of the compound of formula (A-I) and a borylating agent is performed using a catalyst system comprising $NiCl_2$ and $P(Octyl)_3$ in the presence of $K_2CO_3$ and $Cs_2CO_3$ wherein the molar ratio of $K_2CO_3$ and $Cs_2CO_3$ is 9:1.

In some embodiments, the method further comprises combining the nickel precursor and the ligand to prepare the first catalyst. In some embodiments, the first catalyst is prepared using one or more organic solvents. In some embodiments, the reaction of the compound of formula (A-I) and the borylating agent is performed in an organic solvent. In some embodiments, the organic solvent is selected from THF, $CH_2Cl_2$, chlorobenzene, AcOEt, and toluene. In some embodiments, the organic solvent is toluene or THF.

In some embodiments, the reaction of the compound of formula (A-I) and the borylating agent is performed at a temperature in the range of about 70° C. to 100° C. In some embodiments, the reaction of the compound of formula (A-I) and the borylating agent is performed at a temperature of about 90° C.

In some embodiments, the cyclopropyl group is introduced by reacting the organoboron intermediate (e.g., compound of formula (A-II)) with a carbenoid or with diazomethane in the presence of a second catalyst. In some embodiments, the cyclopropyl group is introduced by reacting the organoboron intermediate (e.g., compound of formula (A-II)) with diazomethane. In some embodiments, the introduction of the cyclopropyl group in the organoboron intermediate (e.g., compound of formula (A-II)) is performed in the presence of a second catalyst. In some embodiments, the cyclopropyl group is introduced by reacting the organoboron intermediate (e.g., compound of formula (A-II)) with a Simmons Smith reagent. In some embodiments, the cyclopropyl group is introduced using diazomethane.

In some embodiments, the second catalyst is a metal catalyst. In some embodiments, the second catalyst comprises a Pd catalyst, Cu catalyst, Zn catalyst, Fe catalyst, Mn catalyst, Rh catalyst, or combination thereof. In some embodiments, the second catalyst is a Pd catalyst. In some embodiments, the Pd catalyst is a Pd(II) catalyst. In some embodiments, the Pd catalyst is Pd(OAc)$_2$. In some embodiments, the Cu catalyst is a Cu(I) catalyst. In some embodiments, the Cu catalyst is Cu(OTf), Cu(OtBu), or CuCl/NaBArF.

In some embodiments, the reaction of the organoboron intermediate (e.g., the compound of formula (A-II)) with a borylating agent is performed in the presence of one or more chiral auxiliaries. In some embodiments, the chiral auxiliaries is combined with the organoboron intermediate to form a chiral complex. In some embodiments, the chiral complex has a structure of formula (A-II'). In some embodiments, the chiral complex can react with the cyclopropylating agent to form a compound of Formula (A-III).

In some embodiments, the chiral auxiliary is selected from the group consisting of mono alcohol, diol, amino alcohol, diamine, and hydroxyl acid and ester. In some embodiments, the chiral auxiliary is selected from the group consisting of (R)-(+)-1-phenylethanol, L-menthol, (−)-borneol, (4S,5S)-2,2-dimethyl-α,α, α',α'-tetraphenyldioxolane-4,5-dimethanol, (R)-(+)-1,1'-bis(2-naphthol), (R)-(−)-2-phenylglycinol, (R)-(−)-2-amino-1-phenylethanol, (S,S)-(−)-2-amino-1,2-diphenylethanol, (R)-(−)-2-pyrrolidinenethanol, (R)-(+)-α,α,-diphenyl-2-pyrrolidinemethanol, ((1R,2S)-(−)-ephedrine, (1R,2R)-(+)-1,2-diphenylethylenediamine, (1R,2R)-(−)-N-p-tosyl-1,2,-diphenylethylenediamine, L-(+)-lactic acid, (R)-(−)-mandelic acid, (−)-methyl L-lactate, L-(+)-tartaric acid, L-(+)-tartaric acid dimethyl ester, ((1S,2S)-(+)-pseudoephedrine, (1R,2S)-(−)-norephedrine, (1R,2S)-(−)-N-methylephedrine, (S)-2-(pyrrolidin-2-yl)propan-2-ol, N-methyl-D-glucamine, (1R,2R)-(−)-2-amino-1-(4-nitrophenyl)-1,3-propanediol, quinine, and hydroquinine. In some embodiments, the chiral auxiliary is ephedrine or an ephedrine derivative. In some embodiments, the chiral auxiliary is selected from ((1S,2S)-(+)-pseudoephedrine, (1R,2S)-(−)-norephedrine, (1R,2S)-(−)-N-methylephedrine, and any combination thereof. In some embodiments, the chiral auxiliary is (1S,2S)-(+)-pseudoephedrine.

In some embodiments, the compound of formula (A-III) can be made with an enantiomeric excess of greater than about 50%, about 60%, about 70%, about 80%, about 90%, about 95%, about 98%, about 99%. In some embodiments, the compound of formula (A-III) can be made with an enantiomeric excess of less than about 50%, about 60%, about 70%, about 80%, about 90%, about 95%, about 98%, about 99%. In some embodiments, the compound of formula (A-III) can be made with an enantiomeric excess in the range of about 30%-60%, about 30%-80%, about 30%-90%, 40%-60%, about 40%-80%, about 340%-90%, about 50%-90%, about 30%-99%, about 40%-99%, or about 50%-99%. In some embodiments, the synthesis of the compound of formula (A-III) (e.g., compound 3) can be achieved with an enantiomeric excess of greater than about 50%, about 60%, about 70%, about 80%, about 90%, or about 95%.

Scheme A below summarizes the synthetic route for the compound of formula (I) described herein. $R^1$ is a carboxylic acid protecting group. The reaction product of step 2 can undergo a step of enantiomer purification to produce the compound of formula (A-III) with high purity. The purification can be performed using chromatography or crystallization

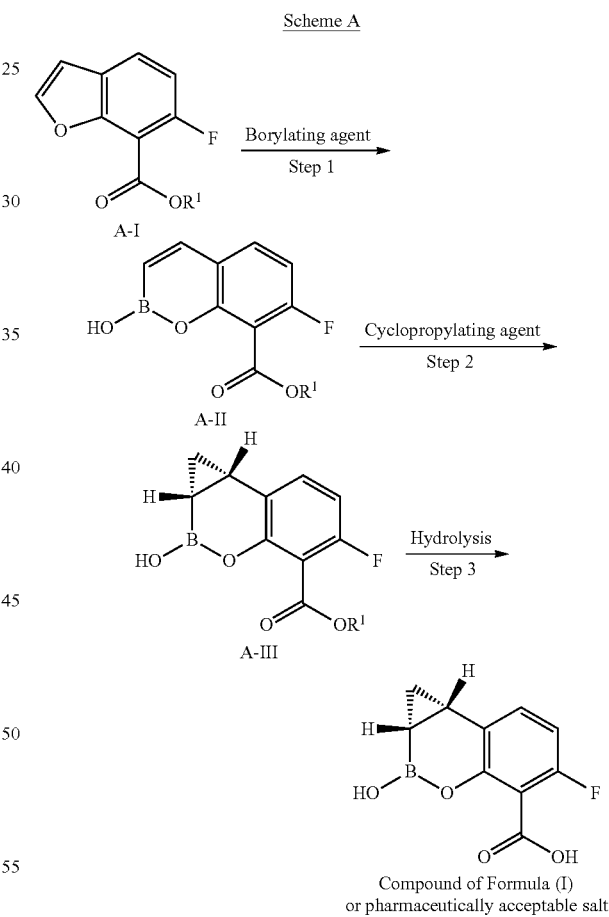

Scheme A

In Scheme A, the step 1 reaction can be performed in the presence of a first catalyst. The first catalyst can be prepared by combining a metal catalyst precursor and one or more ligands. In some embodiments, the first catalyst can be prepared by combining a Ni catalyst precursor and one or more ligands. In some embodiments, the first catalyst can be a Ru or Ni catalyst. The ligands used in the reaction of step 1 can be a phosphine ligand such as P(Octyl)$_3$, diPrf, or dcype. The step 2 reaction can be performed in the presence of a second catalyst. In some embodiments, the second catalyst comprises a metal catalyst and one or more chiral auxiliaries. In some embodiments, the second catalyst comprises a Pd catalyst and one or more chiral auxiliaries such as ephedrine or ephedrine derivatives (e.g., ((1S,2S)-(+)-pseudoephedrine). The reaction product of step 2 can be further purified to produce the compound of formula (A-III) with high purity. The purification can be achieved through chromatography, crystallization and other purification methods suitable for separating enantiomers.

Compound A and its salts (e.g., sodium salt) can be prepared using Scheme B shown below. The cyclopropylating reagent can be $CH_2N_2$, $Pd(OAc)_2$ (with or without chiral auxiliaries) or $Et_2Zn$, $CH_2I_2$, and DME.

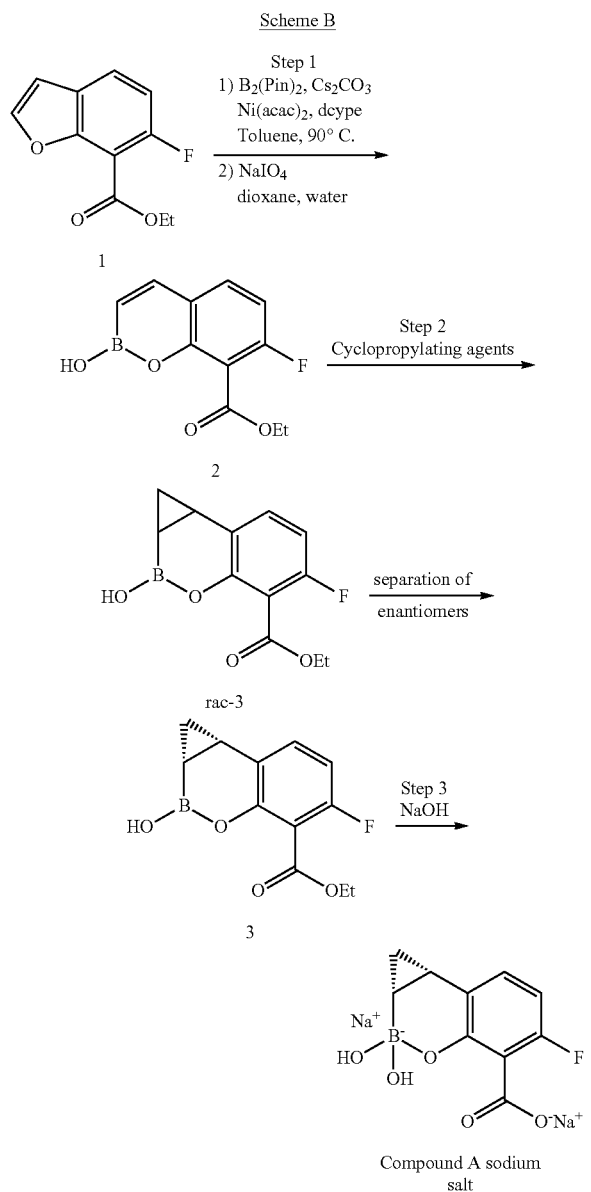

auxiliaries. Some chiral auxiliaries such as ephedrine or ephedrine derivative (e.g., (1S,2S)-(+)-pseudoephedrine) can lead to high enantioselectivity in the cyclopropanation step.

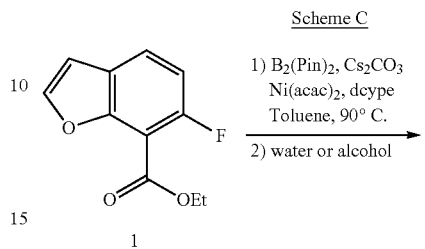

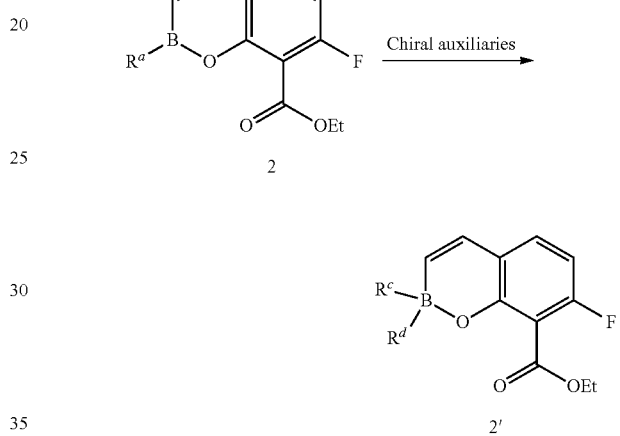

The borylation step can form an organoboron intermediate, which can later be used in the cyclopropylating reaction. Scheme C shows a non-limiting example of the borate intermediate and the subsequent reactions prior to undergoing the cyclopropylating step. In some embodiments, the organoboron intermediate 2 ($R^a$ is OH or optionally substituted —O—$C_{1-6}$ alkyl) can be combined with one or more chiral auxiliaries to form a chiral complex 2' ($R^c$ and $R^d$ with any intervening atoms form an optionally substituted 4-7 membered heterocyclyl ring). In some embodiments, the chiral complex can undergo the cyclopropylating step to form a compound of formula (A-III) with high enantioselectivity.

In some embodiments, the cyclopropanation reactions can be performed where possible in parallel equipment. Results can be monitored by analysis of the original reaction product (e.g., by means of $^1$H-NMR) and analysis of Compound 3 (e.g., chiral HPLC).

Some embodiments relate to the synthesis of Compound A-II (e.g., compound 2). In some embodiments, oxaborins, such as compound 2, can be prepared via boron insertion into the $C_2$—O bond of the benzofurans with a Ni catalyst. In some embodiments, the reaction described in JACS, 2016, 15315, and Yorimitsu et al., both of which are incorporated by reference in their entireties, can be used for the preparation of oxaborins such as compound 2. In some embodiments, the compound 2 can be prepared from the benzofuran derivative 1 as shown in Scheme D.

The enantioselective cyclopropanation of 2 can lead directly to the desired target compound with good stereocontrol. The cyclopropylating reagent used here can include diazomethane with a metal catalyst and one or more chiral Scheme D: Borylation

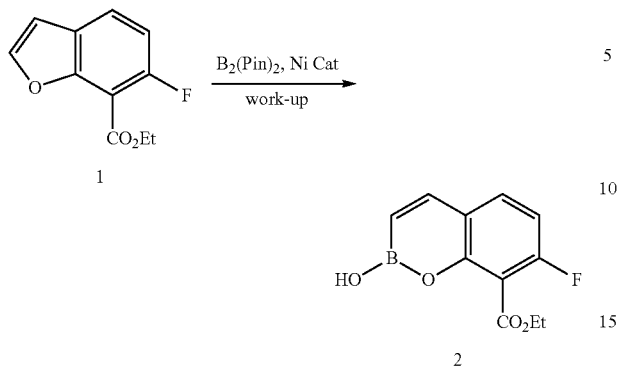

In some embodiments, the reaction with an in-situ generated catalyst from Ni(COD)$_2$ and iPr-NHC or dcype at 10% catalyst loading as described in Scheme D can have a yield between 40-50%. In some embodiments, the reaction can be performed in the glove box. In some embodiments, the reaction can be performed outside the glovebox. In some embodiments, the Cs$_2$CO$_3$ used in large excess could be replaced by a 9:1 mixture of K$_2$CO$_3$/Cs$_2$CO$_3$. In some embodiments, the Ni(Acac)$_2$ and NiCl$_2$ can also work as a Ni catalyst precursor. In some embodiments, the reaction can achieve high yields (>90%), by keeping moisture content as low as possible (dried CsCO3, anhydrous solvents, and alike) using Ni(Acac)$_2$ and dcype. In some embodiments, a 9:1 mixture of K$_2$CO$_3$/Cs$_2$CO$_3$ can achieve yields higher than 80% (e.g., 85% conv. after 24 hr).

In some embodiments, the cleavage of C—O bond in aryl ethers and further functionalization (arylation, alkylation, borylation) can be achieved with a number of metal catalysts, including but not limited to Ni (as described in JACS, 1979, 2246, and JACS, 2016, 6711; JACS, 2017, 10347, which are incorporated by references in their entireties), Ru (as described in Ang Chem Int Ed, 2015, 9293, which is incorporated by reference in its entirety), and Rh (as described in JACS, 2015, 1593, which is incorporated by reference in its entirety). In all cases, a range of ligands chosen from monodentate/bidentate phosphines or N-heterocyclic carbenes can be used. Also additives can be used to increase the yield as described in Org Lett 2013, 6298, which is incorporated by reference in its entirety. In some embodiments, the applicable catalyst and ligand can include Ni, Ru, Rh catalysts and other commercially available ligands/catalysts. In some embodiments, the applicable catalyst and ligand can be Ni.

In some embodiments, relatively cheap catalysts and ligands with high turnover numbers, low cost bases, and readily available other reagents, can be used in the reactions described herein. For instance, NiCl$_2$ is a cheap catalyst when compared with other metal catalysts, and trioctylphosphine is a low cost ligand when compared with other ligands. The combination of NiCl$_2$ and trioctylphosphine can be used in the borylating reaction described herein to achieve a high yield.

In some embodiments, the catalyst for the conversion of Compound 1 into Compound 2 (Scheme D) can achieve a yield of at least 90%.

In some embodiments, the reaction can have at least 50% yield to the desired compound 2.

In some embodiments, the applicable catalysts can include the ligand or catalyst shown in Table 1. The exemplified metal precursors for preparing the catalyst for the reaction are listed the tables below.

TABLE 1

Ni metal precursors for the borylating reaction.

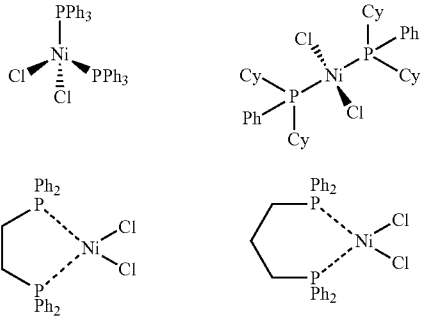

Table 2a and 2b list some examples of ligands including phosphines (monodentate or bidentate, aliphatic or aromatic), NHC ligands, phosphites, phosphoramidites, amines (See examples below of phosphines related to dcpe and NHC's).

TABLE 2a

Examples of ligands for the borylating reaction

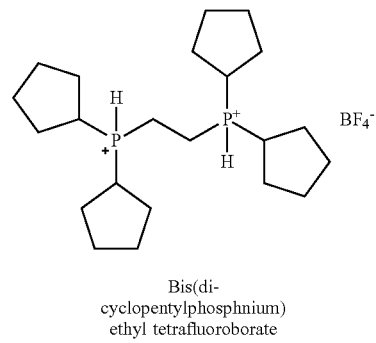

Bis(di-cyclopentylphosphnium) ethyl tetrafluoroborate

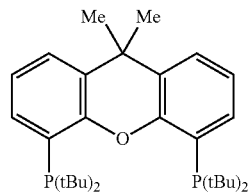

4,5-Bis(di-tert-butylphosphino)-9,9-dimethylxanthene

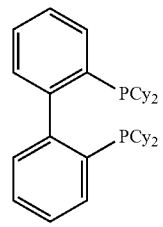

2,2'-bis(dicyclohexylphosphaneyl)-1,1'-biphenyl

TABLE 2a-continued

Examples of ligands for the borylating reaction

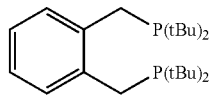

1,2-bis((di-tert-butylphosphaneyl)methyl)benzene

Table 2b

Examples of ligands for the borylating reaction

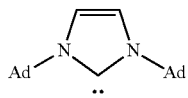

1,3-Bis(1-adamanthyl)imidazolium

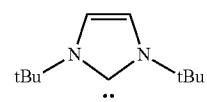

1,3-Di-tert-butylimidazolium

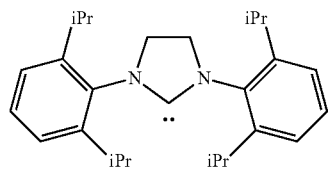

1,3-Bis(2,6-diisopropyl-phenyl)-4,5-dihydroimidazol-2-ylidene

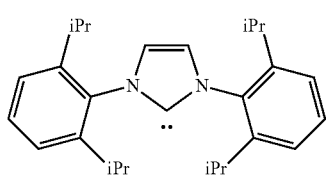

1,3-bis(2,6-diisopropylphenyl)-1H-imidazol-3-ium-2-ide

In addition to the ligand/catalyst, some reaction parameters are also important, including base, solvent, temperature, and additive. In some embodiments, the reaction can be performed in an organic solvent selected from toluene, THF, dioxane, and any combination thereof. In some embodiments, the reaction can use halides, lewis acid to activate the benzofuran for C—O bond cleavage, organic base. In some embodiments, the reaction can use $Cs_2CO_3$.

In some embodiments, the reaction described herein can achieve a 90% isolated yield. In some embodiments, the reaction described herein can have a yield higher than 80% with about 1 mol % catalyst (or as low catalyst loading as possible).

Some embodiments relate to a compound having the structure of

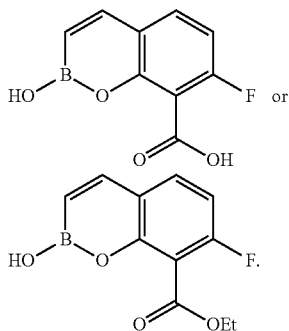

Some embodiments relate to a compound having the structure of

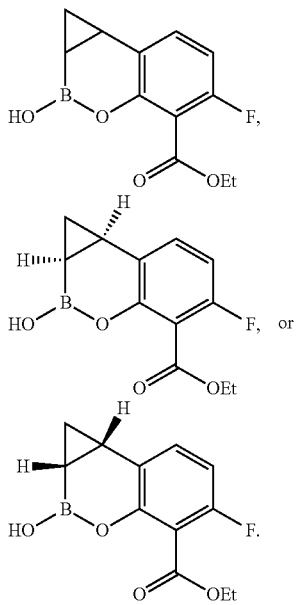

In some embodiments, the pharmaceutically acceptable salts are selected from alkaline metal salts or ammonium salts. In one embodiment, the pharmaceutically acceptable salts are sodium salts.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable salts can also be formed using inorganic and organic bases. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as $Li^+$, $Na^+$, $K^+$, $Mg^{2+}$ and $Ca^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$—, $(CH_3)_2CHCH_2$—, and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO- and RS-, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl"

or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heteroatoms in the ring can include O, N, B, or S. The heterocyclyl group may be designated as "3-6 membered heterocyclyl" or similar designations. In preferred six membered monocyclic heterocyclyls, the heteroatom(s) are selected from one up to three of O, N, B, or S, and in preferred five membered monocyclic heterocyclyls, the heteroatom(s) are selected from one or two heteroatoms selected from O, N, B, or S. In a monocyclic heterocyclyls containing 4, 5, 6, 7, or 8 atoms, the heteroatom(s) are selected from one up to three of O, N, B or S, and in preferred five or six membered monocyclic heterocyclyls, the heteroatom(s) are selected from one or two heteroatoms selected from O, N, B, or S. Examples of heterocyclyl rings include, but are not limited to, dioxaborolane, nitrobororolane, azaborolane, oxaborolane, oxazaborolane, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "sulfonyl" group refers to an "—$SO_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "S-sulfonamido" group refers to a "—$SO_2NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "N-sulfonamido" group refers to a "—$N(R_A)SO_2R_B$" group in which $R_A$ and $R_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "O-carbamyl" group refers to a "—OC(=O)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "N-carbamyl" group refers to an "—$N(R_A)C(=O)OR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "O-thiocarbamyl" group refers to a "—OC(=S)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "N-thiocarbamyl" group refers to an "—$N(R_A)C(=S)OR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "C-amido" group refers to a "—C(=O)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "N-amido" group refers to a "—N(R$_A$)C(=O)R$_B$" group in which R$_A$ and R$_B$ are each independently selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 3-10 membered heterocyclyl, as defined herein.

An "amino" group refers to a "—NR$_A$R$_B$" group in which R$_A$ and R$_B$ are each independently selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 3-10 membered heterocyclyl, as defined herein. A non-limiting example includes free amino (i.e., —NH$_2$).

An "aminoalkyl" group refers to an amino group connected via an alkylene group.

An "alkoxyalkyl" group refers to an alkoxy group connected via an alkylene group, such as a "C$_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substitutents independently selected from C$_1$-C$_6$ alkyl, C$_1$-C$_6$ alkenyl, C$_1$-C$_6$ alkynyl, C$_1$-C$_6$ heteroalkyl, C$_3$-C$_7$ carbocyclyl (optionally substituted with halo, C$_1$-C$_6$ alkyl, C$_1$-C$_6$ alkoxy, C$_1$-C$_6$ haloalkyl, and C$_1$-C$_6$ haloalkoxy), C$_3$-C$_7$-carbocyclyl-C$_1$-C$_6$-alkyl (optionally substituted with halo, C$_1$-C$_6$ alkyl, C$_1$-C$_6$ alkoxy, C$_1$-C$_6$ haloalkyl, and C$_1$-C$_6$ haloalkoxy), 3-10 membered heterocyclyl (optionally substituted with halo, C$_1$-C$_6$ alkyl, C$_1$-C$_6$ alkoxy, C$_1$-C$_6$ haloalkyl, and C$_1$-C$_6$ haloalkoxy), 3-10 membered heterocyclyl-C$_1$-C$_6$-alkyl (optionally substituted with halo, C$_1$-C$_6$ alkyl, C$_1$-C$_6$ alkoxy, C$_1$-C$_6$ haloalkyl, and C$_1$-C$_6$ haloalkoxy), aryl (optionally substituted with halo, C$_1$-C$_6$ alkyl, C$_1$-C$_6$ alkoxy, C$_1$-C$_6$ haloalkyl, and C$_1$-C$_6$ haloalkoxy), aryl(C$_1$-C$_6$)alkyl (optionally substituted with halo, C$_1$-C$_6$ alkyl, C$_1$-C$_6$ alkoxy, C$_1$-C$_6$ haloalkyl, and C$_1$-C$_6$ haloalkoxy), 5-10 membered heteroaryl (optionally substituted with halo, C$_1$-C$_6$ alkyl, C$_1$-C$_6$ alkoxy, C$_1$-C$_6$ haloalkyl, and C$_1$-C$_6$ haloalkoxy), 5-10 membered heteroaryl(C$_1$-C$_6$)alkyl (optionally substituted with halo, C$_1$-C$_6$alkyl, C$_1$-C$_6$ alkoxy, C$_1$-C$_6$ haloalkyl, and C$_1$-C$_6$ haloalkoxy), halo, cyano, hydroxy, C$_1$-C$_6$ alkoxy, C$_1$-C$_6$ alkoxy(C$_1$-C$_6$)alkyl (i.e., ether), aryloxy, sulfhydryl (mercapto), halo(C$_1$-C$_6$) alkyl (e.g., —CF$_3$), halo(C$_1$-C$_6$)alkoxy (e.g., —OCF$_3$), C$_1$-C$_6$ alkylthio, arylthio, amino, amino(C$_1$-C$_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Unless otherwise indicated, wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

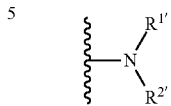

and R$^{1'}$ and R$^{2'}$ are defined as selected from the group consisting of hydrogen and alkyl, or R$^{1'}$ and R$^{2'}$ together with the nitrogen to which they are attached form a heteroaryl, it is meant that R$^{1'}$ and R$^{2'}$ can be selected from hydrogen or alkyl, or alternatively, the substructure has structure:

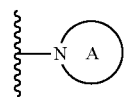

where ring A is a heteroaryl ring containing the depicted nitrogen.

Similarly, when two "adjacent" R groups are said to form a ring "together with the atoms to which they are attached," it is meant that the collective unit of the atoms, intervening bonds, and the two R groups are the recited ring. For example, when the following substructure is present:

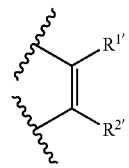

and R$^{1'}$ and R$^{2'}$ are defined as selected from the group consisting of hydrogen and alkyl, or R$^{1'}$ and R$^{2'}$ together with the atoms to which they are attached form an aryl or carbocylyl, it is meant that R$^{1'}$ and R$^{2'}$ can be selected from hydrogen or alkyl, or alternatively, the substructure has structure:

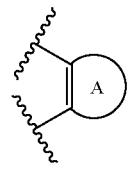

where A is an aryl ring or a carbocylyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

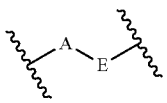

includes the substituent being oriented such that the A is attached at the leftmost attachment point of the molecule as well as the case in which A is attached at the rightmost attachment point of the molecule.

Protecting Groups

In some circumstances, a chemical reaction may need to be performed selectively at one reactive site in a multifunctional compound. One such method that is useful for accomplishing such selectivity is to temporarily block one or more reactive sites in the multifunctional compound with a protective group. Such a method is often referred to as "protecting" the functional group. Many protecting groups are known in the art. See, e.g., Greene et al., Protective Groups in Organic Synthesis, Third Ed. (John Wiley & Sons, Inc. 1999), herein incorporated by reference in its entirety; Wutz et al., Greene's Protective Groups in Organic Synthesis, Fourth Ed. (John Wiley & Sons, Inc. 2007), herein incorporated by reference in its entirety. When more than one reactive site in a multifunctional compound requires protecting, or when a compound is prepared that will possess more than one protected functional group, it is important to use orthogonal protecting groups. Protecting groups are orthogonal if they are susceptible to selective removal.

In some embodiments, it may be necessary to protect one or more functional groups so as to prevent their interference in the desired reaction. For example, it may be necessary to protect one or more functional groups such as amines, carboxylic acids, and/or hydroxyl groups.

Suitable protecting groups for carboxylic acids include: esters such as enzymatically cleavable esters including heptyl, 2-N-(morpholino)ethyl, choline, (methoxyethoxy)ethyl, methoxyethyl; alkyl esters such as methyl, ethyl, propyl, isopropyl, butyl, tert-butyl, sec-butyl, pentyl, neopentyl, hexyl, heptyl, nonnyl, decanyl, and configurational isomers thereof; substituted methyl esters such as 9-fluroenylmethyl, methoxymethyl, methylthiomethyl, tetrahydropyranyl, teatrahydrofuranyl, methoxyethoxymethyl, 2-(trimethylsilyl)ethoxymethyl, benzyloxymethyl, pivaloyloxymethyl, phenylacetoxymethyl, triisopropylsilylmethyl, cyanomethyl, acetol, phencacyl, p-bromophenacyl, α-methylphenacyl, p-methoxyphenacyl, desyl, carboamidomethyl, p-azobenzenecarboxamidomethyl, N-phthalidimdomethyl; 2-substituted ethyl esters such as 2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl) ethyl, 2-(p-toluenesulfonyl)ethyl, 2-(2'-pyridyl)ethyl,2-(p-methoxyphenyl)ethyl,2-(diphenylphosphino)ethyl,1-methyl-1-phenylethyl, 2-(4-acetyl-2-nitrophenyl)ethyl, 2-cyanoethyl, 3-methyl-3-pentyl, dicyclopropylmethyl, 2,4-dimethyl-3-pentyl, cyclopentyl, cyclohexyl, allyl, methallyl, 2-methylbut-e-en-2-yl, 3-methylbut-2-(prenyl), 3-buten-1-yl, 4-(trimethylsilyl)-2-buten-1-yl, cinnamyl, α-methylcinnamyl, prop-2-ynyl, phenyl; 2,6-dialkylphenyl esters such as 2,6-dimethylphenyl, 2,6-diisopropylphenyl, 2,6-di-t-butyl-4-methylphenyl, 2,6-di-t-butyl-4-methoxyphenyl, p-(methylthio)phenyl, pentafluorophenyl, benzyl; substituted benzyl esters such as triphenylmethyl, diphenylmethyl, bis(o-nitrophenyl)methyl, 9-anthrylmethyl, 2-(9,10-dioxo)anthrylmethyl, 5-dibenzosuberyl, 1-pyreneylmethyl, 2-(trifluoromethyl)-6-chromonylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, 4-azidomethoxybenzyl, 4-{N-[1-(4,4-dimethyl-2,6-dioxocyclohexylidene)-3-methylbutyl] amino}benzyl, piperonyl, 4-picolyl, polymer supported p-benzyl; silyl esters such as trimethylsilyl, triethylsilyl, t-butyldimethylsilyl, i-propyldimethylsilyl, phenyldimethylsilyl, di-t-butylmethylsilyl, triisopropylsilyl; activated esters such as thiol esters; oxazoles; 2-alkyl-1,3-axazoline; 4-alkyl-5-oxo-1,3-oxazolidine; 2,2-bistrifluoromethyl-4-alkyl-5-oxo-1,3-oxazolidine; 5-alkyl-4-oxo-1,3-dioxolane; dioxanones; ortho esters; pentaaminocobalt(III) complexes; and stannyl esters such as triethylstannyl and tri-n-butylstannyl; amides such as N,N-dimethyl, pyrrolidinyl, piperidinyl, 5,6-dihydrophenanthridinyl, o-nitroanilide, N-7-nitroindolyl, N-8-nitro-1,2,3,4-tetrahydroquinolyl, 2-(2-aminophenyl)acetaldehyde dimethyl acetal amide, and polymer supported p-benzenesulfonamide; hydrazides such as N-phenyl, N,N'diisopropyl; and tetraalkylammonium salts such as methyl, ethyl, propyl, isopropyl, butyl, tert-butyl, sec-butyl, pentyl, neopentyl, hexyl, heptyl, nonnyl, decanyl, and configurational isomers thereof.

EXAMPLES

Example 1

Synthesis of Ethyl 6-Fluorobenzofuran-7-carboxylate

Benzofuran 1 is an intermediate for preparing compound A and was synthesized in 3 steps as shown in Scheme 1A. Fisher esterification of 6-fluoro-salicylic acid (1a) in ethanol with methanesulfonic acid proceeded slowly (2-3 days) to give 1b in excellent yield. The phenol group was then alkylated with bromoacetaldehyde diethyl acetal in the presence of t-BuOK in DMF at 100° C. to give benzofuran precursor 1c in quantitative yield. The ring closure was then achieved with Amberlyst 15 (sulfonic acid resin) in dichloroethane at 90° C. to give the desired benzofuran 1 with an overall yield of 40-45%.

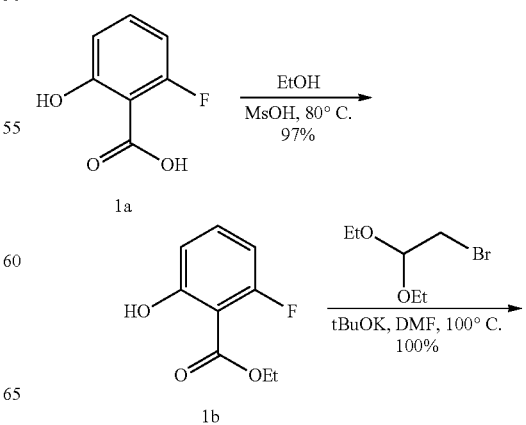

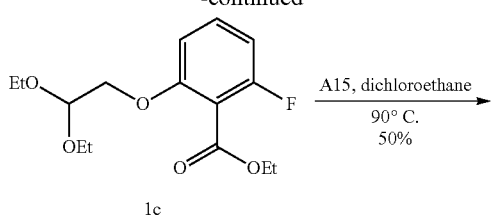

Synthesis of ethyl 6-fluoro-salicylate 1b

Methanesulfonic acid (20.8 mL, 0.32 mol,) was added to a solution of hydroxy acid 1a (50 g, 0.32 mol) in EtOH (350 mL) at room temperature. The clear pale orange solution was heated at reflux. After 3 days at reflux, HPLC shows 93.5% conversion. EtOH was distilled off (200 mL) and replaced with fresh EtOH (200 mL). After an additional 24 h at 90° C., HPLC shows 96.1% conversion. The pH of the cooled reaction mixture was raised to 7.0 with 4 N NaOH (80 mL) and most of the EtOH was removed under vacuum. The residual heterogeneous biphasic mixture was taken up in ethyl acetate (250 mL) and water (100 mL). The layers were separated and the organic phase was washed with water (100 mL), then concentrated to dryness, azeotroped with heptane (100 mL) and dried under high vacuum to give 54.9 g of compound 1b (93% yield). The product was used without purification.

Benzofuran Precursor 1c:

Solid t-BuOK (43.5 g, 0.39 mol) was added to a solution of phenol 1b (54.9 g, 0.3 mol) in DMF (220 mL) at room temperature (exotherm from 24 to 61° C.). Once the temperature started to decrease, the alkylating agent (50 mL, 0.33 mol, 1.1 eq,) was added and the reaction mixture was heated at 100° C. After stirring at 100° C. for 24 h, HPLC shows about 7.5% of starting material remaining. More alkylating agent (5 mL, 30 mmol, 0.1 eq,) was added. After stirring an additional 24 h at 100° C., HPLC shows only 2.4% of starting material remaining. The cooled black reaction mixture was quenched with water (250 mL) and diluted with MTBE (250 mL). The layers were separated and the organic phase washed with water (2×250 mL). The MTBE solution was passed through a silica plug (9 g) and the plug was rinsed with MTBE (2×20 mL). The combined filtrates were concentrated under reduced pressure to give a black oil 91 g 101% yield.

Synthesis of Benzofuran 1:

Amberlyst 15 (A15) resin (1.78 g, 20 wt %) was added to a solution of diethyl acetal 1c (8.9 g, 30 mmol) in dichloroethane (89 mL) at room temperature. The reaction mixture was heated at 90° C. After 3 days at 90° C., HPLC shows only 2.5% of starting material. The reaction mixture was cooled to room temperature. The resin was filtered off and rinsed with dichloroethane. The filtrate was concentrated to dryness. The black oil was purified by column chromatography on silica gel using a gradient of 0-30% ethyl acetate in hexanes to give a pale orange oil, 3.049 g 49% yield.

Example 2

Benzofuran 1f' was synthesized in 6 steps with only 2 isolations as shown in Scheme 1B. Sodium hydroxide-mediated fluoride displacement of 2,6-difluorobenzoic acid proceeded in excellent yield in water at 145° C. and the crude 6-fluorosalicylic acid 1b' was converted to the ethyl ester 1c' with methanesulfonic acid in ethanol at reflux. The phenol moiety was then alkylated in a 2-step one pot procedure by reacting the tBuOK-mediated potassium phenoxide with methyl chloroacetate followed by in-situ selective saponification of the methyl ester to give phenoxyacetic acid 1d' in 75% overall yield for 3 steps after crystallization from water. The carboxylic acid was derivatized as the acyl chloride with oxalyl chloride and catalytic DMF, and treatment with 2 equivalents of aluminum chloride achieves the ring closure to benzofuranone 1e'. Compound 1e' was then converted to the benzofuran 1 in a 2-step one pot procedure by first reduction of the ketone with sodium borohydride and acetic acid in THF followed by in-situ dehydration of the intermediate hydroxy-dihydrobenzofuran with HCl. The final compound was then obtained by saponification of the ethyl ester with NaOH in water and THF followed by crystallization from water to give 6-fluorobenzofuran-7-carboxylic acid 1f' in 70% yield for the last 3 steps and in an overall yield from 2,6-difluorobenzoic acid of 53%.

Scheme 1B

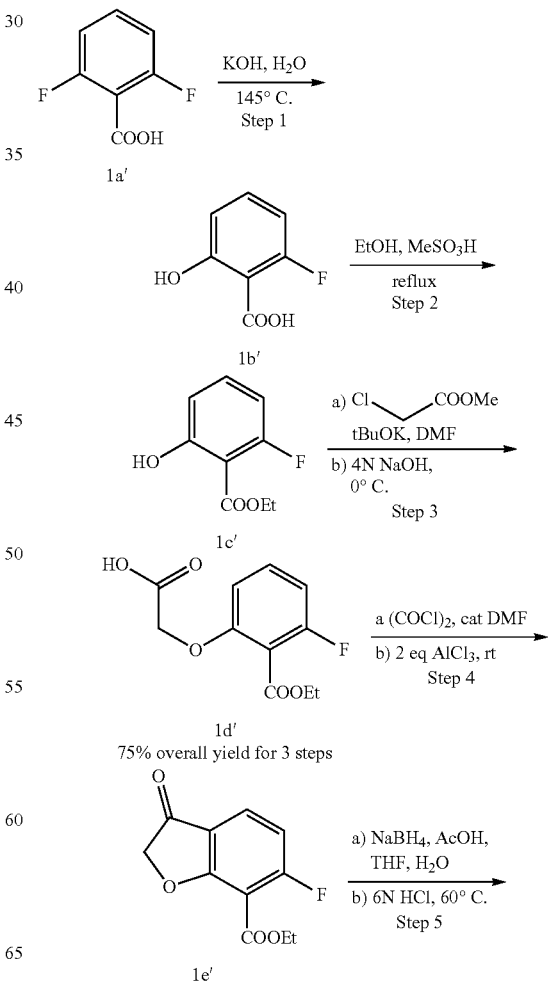

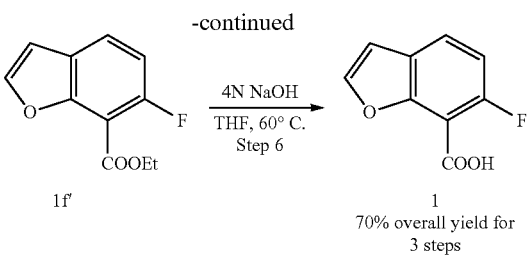

70% overall yield for 3 steps

Step 1: Synthesis of 6-fluoro-salicylic acid 1b'. Solid NaOH (70.8 g, 1.77 mol, 7 eq) was added in portions to a suspension of 2,6-difluorobenzoic acid (40 g, 0.25 mol) in water (160 mL) at 90° C. in a TEFLON flask and the solution was heated at 145° C. After stirring at 140° C. for 3 days, conversion was 100% by HPLC and there was 4% of dimer. The reaction mixture was cooled to room temperature and diluted with a mixture of 9/1 MTBE/ethanol (200 mL). The biphasic mixture was cooled to 2.2° C. Conc. HCl was added keeping the temperature <20° C. until pH 1.8 (150 mL). The organic layer was separated from the milky white aqueous layer, washed with 0.01 N HCl (120 mL) and concentrated to dryness to give a pink solid, 37.7 g, 95.4% yield, 99.83% purity.

Step 2: Synthesis of ethyl 6-fluorosalicylate 1c'. Methanesulfonic acid (18.7 mL, 288 mmol, 0.6 eq) was added to a solution of crude fluorosalicylic acid 1b' (75 g, 480 mmol, 99.7% purity) in anhydrous EtOH (375 mL) at room temperature. The clear light amber solution was heated at 95° C. After 8 h at reflux half of the solvent was removed by distillation and replaced with anhydrous EtOH. After refluxing for 3 days, conversion was 93% by HPLC. Half of the EtOH was removed by distillation and replaced with the same amount of anhydrous EtOH. After refluxing for an additional 24 h conversion was 96% by HPLC. The clear light amber solution was cooled to 0° C. The pH was raised to about 7.0 with 4 N NaOH (actual pH 7.15; 78 mL) and most of the EtOH was removed under vacuum. The residual heterogeneous biphasic mixture was taken up in heptane (225 mL) and water (75 mL). The layers were separated and the organic layer was washed with water (150 mL), concentrated to dryness, azeotroped with heptane (2×75 mL) to remove water and residual EtOH and dried under vacuum to give 79.2 g. 93% yield, 99.48% purity.

Step 3: Synthesis of 2-(2-ethoxycarbonyl-3-fluorophenoxy)acetic acid 1d'. Solid tBuOK (25.6 g, 228 mmol) was added to a solution of crude phenol (40 g, 217 mmol, 99.56% purity) in DMF (160 mL) at room temperature (exotherm to 55° C.). After stirring at room temperature for 2 h, a slightly heterogeneous mixture was obtained. Methyl chloroacetate (22 mL, 330 mmol) was added at once at room temperature (slow exotherm from 22 to 38.2° C. over 10 min). After stirring at room temperature for 18 h, HPLC shows 4.1% of starting material remaining and 0.5% of Claisen condensation side product. The heterogeneous reaction mixture was cooled to −4° C. and water was added (40 mL, note 2). The reaction mixture was cooled to −15° C. and 2 N NaOH (131 mL, 262 mmol) was added keeping the temperature <−10° C. Upon completion of the saponification of the methyl ester (0.9% of Claisen condensation side product), the reaction mixture was diluted with MTBE (80 mL) and the pH of the biphasic mixture was lowered to 6.0 with 6 N HCl (5 mL). The layers were separated (keep aqueous layer) and the aqueous layer was extracted with MTBE (80 mL, keep aqueous layer). MTBE (120 mL) was added to the aqueous layer and the pH was lowered to 2.0 with 6 N HCl. The layers were separated (keep organic layer) and the aqueous layer was extracted with MTBE (2×80 mL, note 5). The combined organic extracts of the pH 2 aqueous layer were washed with water (2×80 mL) and most of the MTBE was removed under vacuum. Water (160 mL) was added and the biphasic mixture was heated at 60° C. under a light vacuum to remove the remaining MTBE (crude product purity=96.35%). The mixture was allowed to cool and at 30° C. seeds (5 mg) were added. The product started to crystallize in minutes. After stirring at room temperature overnight the solids were collected by filtration and rinsed with water (2×60 mL) then heptane (2×60 mL), air dried then dried under vacuum to give a white powder 44.2 g, 84% yield, 99.79% purity.

Step 4: Synthesis of ethyl 6-fluoro-3-oxo-benzofuran-7-carboxylate 1e'. Oxalyl chloride (6.3 mL, 73 mmol) was added to a solution of phenoxyacetic acid 1d' (14.8 g, 61 mmol, purity 99.5%) in dichloromethane (75 mL) containing DMF (0.08 mL) at room temperature (gas evolution). After stirring at room temperature for 3 h, <1% of starting material remained by HPLC. The clear amber reaction mixture was concentrated to dryness and azeotroped with dichloromethane (2×30 mL). The brown oil was taken up in dichloromethane (30 mL) and added to a suspension of aluminum chloride (16.3 g, 122 mmol) in dichloromethane (45 mL) at 0° C. keeping the temperature <10° C. to get a clear amber solution. The reaction mixture was warmed to room temperature. After stirring at room temperature for 1 h, the reaction mixture was heater at reflux. After stirring at reflux for 1 h, HPLC shows <1% of starting material. The reaction mixture was cooled to 0° C. and cannulated into water (75 mL) at 0° C. keeping the temperature <10° C. The layers were separated and the organic layer was washed with brine (2×45 mL) then concentrated to dryness to give a yellow oil that crystallized on standing 13.47 g, 98% yield, 91.6% purity.

Step 5: Synthesis of ethyl 6-fluorobenzofuran-7-carboxylate 1. A 3 M aqueous solution of NaBH$_4$ was prepared by dissolving NaBH$_4$ (2.27 g) in 0.01N NaOH (20 mL) to give a turbid solution at pH 11.3. The pH of this solution was raised to 12 with a few drops of 4 N NaOH. Aliquots of this solution were added to a solution of benzofuranone 5 (13 g, 58 mmol, 91.6% purity) and AcOH (1.3 mL, 23 mmol, note 1) in THF (52 mL) at 0° C. (CAUTION gas evolution) keeping the temperature <5° C. and checking periodically for complete conversion by HPLC. A total of 16.5 mL was added (note 2). 6 N HCl (19 mL, 116 mmol) was added at 0° C. (little gas evolution); a biphasic mixture was obtained which was heated at 60° C. After stirring at 60° C. for 2 h, HPLC shows no intermediate alcohol left. The biphasic reaction mixture was cooled to room temperature and diluted with heptane (25 mL) and water. The aqueous layer was back extracted with 1/1 THF/heptane (25 ml). The combined organic extracts were washed sequentially with water (40 mL), 1 N NaOH (40 mL, note) and water (2×40 mL) then concentrated to dryness to give an amber oil, 9.24 g, 77% yield, 97.55% purity.

Synthesis of 6-fluorobenzofuran-7-carboxylic acid 1f'. 4 N NaOH (40 mL, 160 mmol) was added to a solution of ethyl ester (16.62 g, 80 mmol, 95.66% purity) in THF (40 mL) at room temperature. The biphasic red reaction mixture was heated at 60° C. After 90 min at 60° C. HPLC shows complete conversion. The cooled clear red reaction mixture was extracted with MTBE (40 mL) to remove residual organics. The aqueous layer was concentrated under reduced pressure to remove THF. The solution was polish filtered through celite and the pad and flask were rinsed with water (20 mL total). The pH of the filtrate was lowered to 2 over 1 h with 3 N HCl, After stirring at room temperature overnight, the solids were collected by filtration and rinsed with water (2×30 mL), air dried, then dried under high vacuum to give a cream-colored powder 13.4 g, 93% yield, 99.16% purity.

Example 3. Synthesis of Compound A

Compound A is a preclinical beta-lactamase inhibitor. An overview of the synthetic route is shown in the Scheme 2 below. The reaction described in step 1 can involve an economic catalyst/ligand combination. Enantioselectivity can be introduced through the reaction for step 2, and isolation of enantiomers can be achieved so that chromatography is not required.

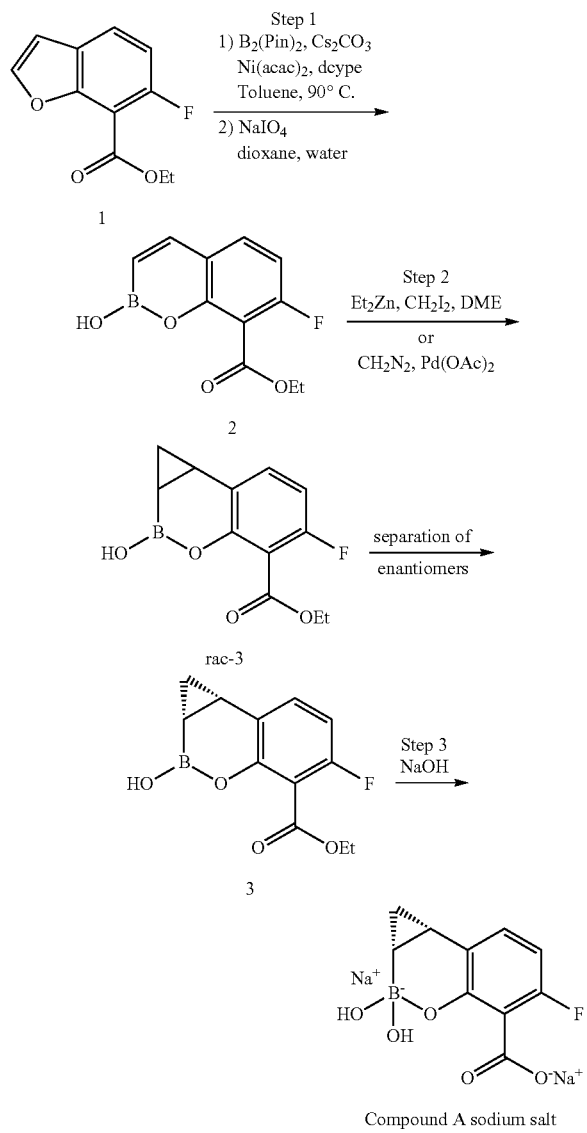

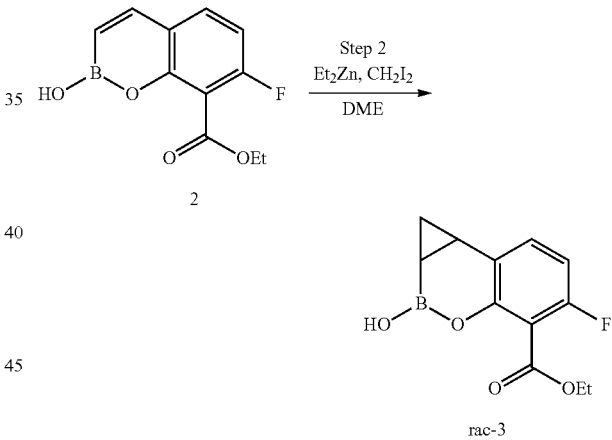

A heterogeneous mixture of benzofuran 1 (3.90 g, 19 mmol), diboron reagent (7.14 g, 28 mmol), oven dried and powered cesium carbonate (18.31 g, 56 mmol), dcype ligand (1.58 g, 4 mmol) and Ni(acac)$_2$ (0.96 g, 4 mmol) in toluene (39 mL) in an oven dried flask was degassed (a slight blackening of the reaction mixture can be observed). The reaction mixture was heated at 90° C. After 6 h at 90° C., HPLC showed 69% conversion. After 28 h at 90° C., HPLC showed 98.7% conversion. The reaction mixture was cooled to 0° C. Water (39 mL) was added and 6 N HCl was added until pH 2. After stirring at 0° C. for 2 h the solids (pinacol heaxahydrate) were filtered off and rinsed with toluene. The filtrate was partitioned and the organics were washed twice with water then concentrated to dryness. The residue was subjected to flash chromatography on silica gel (220 g, 0-8% MeOH in dichloromethane to give 4.37 g of product containing 24 mol % of pinacol species (corrected yield 90%).

A solution of sodium periodate (1.39 g, 7 mmol) in water (16 mL) was added to a solution of the chromatographed product in dioxane (8 mL) at room temperature. After stirring at room temperature for 4 h, TLC (9/1 CH$_2$C$_2$/MeOH) showed no pinacol left. The yellow heterogeneous reaction mixture was diluted with water and ethyl acetate. The layers were separated and the organics were washed with water containing 20% of brine then concentrated to dryness. The residue was subjected to column chromatography on silica gel (120 g, 0-8% MeOH in dichloromethane) to afford 3.24 g of compound 2 (106% yield). The product crystallized in the flask over 2 days.

Neat diethylzine (1.42 g, 11.5 mmol) was added to a solution of DME (1.2 mL, 1.04 mmol) in dichloromethane (3 mL) at −10° C. A solution of methylene iodide (6.17 g, 23.1 mmol) in dichloromethane (2 mL) was added slowly (25 min) keeping the temperature between −12 and −9° C. to give a clear colorless solution. After stirring 10 min at −10° C., a solution of vinyl boronate compound 2 (0.68 g, 2.88 mmol) in dichloromethane (3 mL) was added slowly (10 min) keeping the temperature below −7° C. The cooling bath was removed and the clear yellow solution was allowed to warm to room temperature. At 19° C. a precipitate was observed, HPLC shows 58% conversion. After stirring at room temperature for 3 h, a clear solution was obtained. After 5.5 h at room temperature a heterogeneous mixture was obtained; HPLC shows 88% conversion. The heterogeneous yellow reaction mixture was left stirring at room temperature over the weekend; HPLC shows 96% conversion. The reaction mixture was quenched with 1 M aqueous phosphoric acid and was diluted with dichloromethane. The layers were separated and the organics were washed with water, then concentrated to dryness. The crude product was subjected to flash chromatography on silica gel (80 g, 0-15% MeOH in dichloromethane) to afford 692 mg of compound rac-3 (96% yield).

Separation of Isomers of Compound Rac-3

Separation of the isomers of compound 3 was accomplished using a RegisPack 250 mm×4.6 mm id, 5 micron column with a hexane-EtOH-MeOH-TFA gradient.

Scheme 4

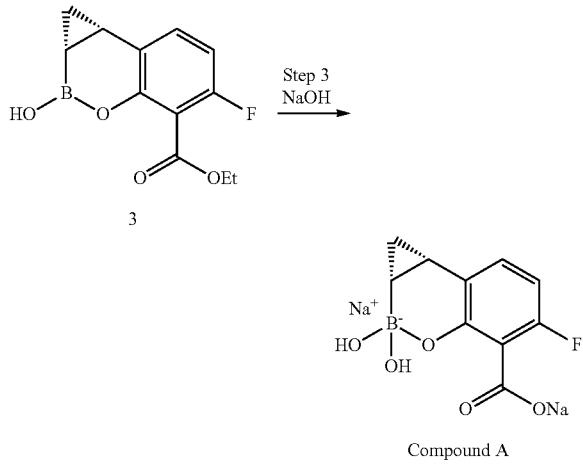

25% NaOH (2.3 mL) was added to a solution of ethyl ester 3 (760 mg) in dioxane (2.3 mL) at room temperature. The reaction mixture was stirred at room temperature for 3 days, after which HPLC shows no starting material remaining. The pH of the clear orange solution was lowered to 8.0 with 6 N HCl. The solution was extracted with MTBE to remove the organics. The aqueous layer was concentrated to dryness to remove dioxane. The residue was taken up in water (5 mL) and filtered through a syringe filter. The clear orange filtrate was concentrated to dryness. The residue was taken up in water (2 mL) and dioxane (12 mL) was added. A biphasic heterogeneous mixture was obtained. After stirring at room temperature overnight, the solids were collected by filtration and rinsed with acetone, air dried then dried under high vacuum to give Compound A as an off white powder, 452 mg (52% yield). The biphasic filtrate was left standing at room temperature over the weekend. Solids were seen and collected then rinsed with dioxane and dried to give a second crop of 275 mg (32% yield).

Example 4

In a 2.5 mL vial equipped with a magnetic stirrer, NiCl$_2$ (0.24 mmol; 31.10 mg) and P(Octyl)$_3$ (0.56 mmol; 207.56 mg) were added and dissolved in THF (1.5 mL). The vial was capped and stirred at 90° C. for 1 h.

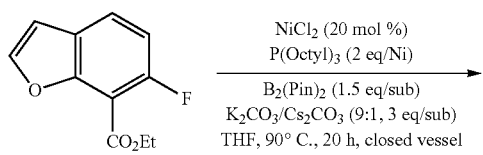

NiCl$_2$ (20 mol %)
P(Octyl)$_3$ (2 eq/Ni)
B$_2$(Pin)$_2$ (1.5 eq/sub)
K$_2$CO$_3$/Cs$_2$CO$_3$ (9:1, 3 eq/sub)
THF, 90° C., 20 h, closed vessel

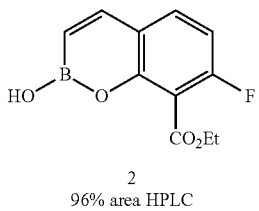

2
96% area HPLC

In a 5 mL vial equipped with a magnetic stirrer, K$_2$CO$_3$ (447.6 mg) and Cs$_2$CO$_3$ (117.2 mg) (3.6 mmol base 9/1 ratio) were added. Next B$_2$(Pin)$_2$ (1.84 mmol; 467.25 mg) was added. The catalyst solution was added to the mixture, followed by more THF (4.5 mL). Finally, the substrate (1.2 mmol; 250 mg) was added and the vial was capped. The reaction was stirred at 90° C. overnight (ca. 20 h).

To the reaction mixture, Et$_2$O (4 mL) was added followed by H$_2$O (4 mL) was added and 6N HCl was added until pH=1 (ca 1.2 mL). The mixture was stirred at 0° C. for 30 min. Then, the organic phase was extracted, dried with sodium sulphate, filtered and the solvent removed in vacuo. The sample was subjected to HPLC analysis (in MeCN and a small amount of Toluene as solvent). The procedure with NiCl$_2$/P(Octyl)$_3$ at 20 mol % catalyst loading had up to 96 area % of the desired product obtained, while at 10 mol % an 87 area % of the desired product, was obtained, dosing the catalyst solution slowly over time.

The NiCl$_2$ and P(Octyl)$_3$ for forming the catalyst in this reaction had the advantages of lower cost while still maintaining a high conversion and yield (at 20 mol %).

Example 5

11 Ni catalysts were tested using 3 Ni precursors (NiC$_2$, Ni(Acac)$_2$, Ni(COD)$_2$) and 3 bisphosphines dppf, diPrf, and dcype shown below. In all cases, 1.5 eq of B$_2$(Pin)$_2$ relative to the substrate and 3 eq of Cs$_2$(CO)$_3$ was used at S/C=5 (i.e. 20 mol % of catalyst). The reactions were run for 17-20 h at 90° C.

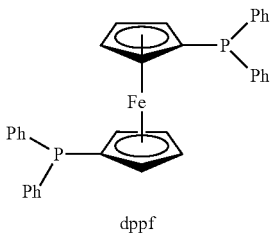

dppf

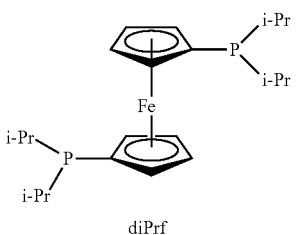

diPrf

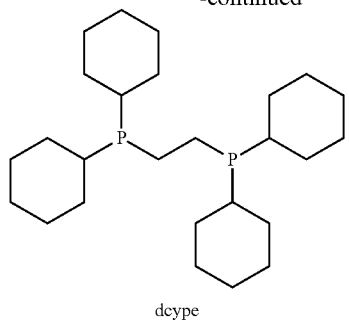

dcype

All Ni precursors and ligands were handled under inert atmosphere inside a $N_2$ glovebox. All catalysts were preformed by stirring the Ni precursors in presence of the ligands for 1 h at 90° C. It was also observed that $B_2(Pin)_2$ and $Cs_2(CO_3)$ were fairly hygroscopic and should be better handled under inert atmosphere as well.

Catalyst preparation: In the $N_2$ glovebox, the Ni precursor (0.06 mmol), the ligand (0.08 mmol) and $Cs_2(CO)_3$ (50 mg, 0.15 mmol) were placed inside a 2.5 mL vial equipped with a magnetic stirrer. Toluene (0.75 mL) was added and the vials were capped and stirred at 90° C. for 1 h.

Reaction procedure: In the $N_2$ glovebox, $B_2(Pin)_2$ (0.46 mmol; 116.8 mg) and $Cs_2(CO_3)$ (0.9 mmol; 293.2 mg) were added in a 2.5 mL vial equipped with a magnetic stirrer. The catalyst solution and toluene (0.75 mL) was next added and finally, the benzofuran substrate (0.3 mmol; 62.4 mg) was added. The vials were capped and stirred at 90° C. for 17 to 23 h.

Reaction work up (outside of the glovebox): Distilled water (1 mL) was added to the crude reaction. The solution was cooled down to 0° C. and HCl 6 N (roughly 300 μL) was added until the pH reached 1. The solution was stirred for 40 min (white solids are formed in the aqueous phase). $Et_2O$ (2 mL) was added to the vials and the organic phase was extracted and dried over $Na_2SO_4$. The organic phase was filtered and the solvent removed in vacuo.

The results of the catalytic tests are reported in Table 3 in area %.

$NiCl_2$ as Ni catalyst precursor and dppf as ligand achieved a good yield (Entry 1). With diPrf (Entries 4, 5, 6 in Table 3), good conversion was obtained with $NiC_2$. The HPLC chromatogram was relatively clean with only 1 major other peak at 10.179. With dcype (Entries 7-11 in Table 3), a similar result was obtained but with $Ni(Acac)_2$ as the Ni source—the only difference being that a higher amount of vinyl-phenol was observed in this case. This result was reproduced (Entries 7-8 in Table 3). With $NiCl_2$/diPrf: 96% area product. With $Ni(Acac)_2$/dcype: 92% area product, 1% area vinyl-phenol Determination of yields (quantitative HPLC; isolated) with $NiC_2$/diPrf and $Ni(Acac)_2$/dcype: The two catalysts $NiCl_2$/diPrf and $Ni(Acac)_2$/dcype were tested again on larger scale (factor×4) and at slightly lower S/C (15 mol % instead of 20 mol %) with the goal to determine the yield via quantitative HPLC and isolation of the desired product.

Catalyst preparation: In the $N_2$ glovebox, the Ni precursor (0.18 mmol, 15 mol %), the ligand (diPrf or dcype) (0.21 mmol, 1.17 eq/Ni) were placed inside a vial equipped with a magnetic stirrer. Toluene (3 mL) was added and the vial was capped and stirred at 90° C. for 1 h.

Reaction procedure: In the $N_2$ glovebox, $B_2(Pin)_2$ (1.84 mmol; 467 mg) and $Cs_2(CO_3)$ (3.6 mmol; 1173 mg) were added in a vial equipped with a magnetic stirrer. The catalyst solution was next added as well as 3 mL of Tol. Finally, the benzofuran substrate (1.2 mmol; 250 mg) was added. The vials were capped and stirred at 90° C. for 17 to 23 h.

Reaction work up (outside of the glovebox): The reaction mixture was transferred into a 25 mL vial and diluted with $Et_2O$ (3 mL). $H_2O$ (3 mL) was added and HCl 6N was added until pH=1 (ca 1.2 mL) The mixture was stirred at 0° C. for 30 min. The organic phase was extracted, dried with sodium sulphate, filtered and the solvent removed in vacuo. The sample was subjected to HPLC analysis (in MeCN+a small amount of Tol as solvent)

Isolation via column chromatography: The crude sample was purified by silica gel column chromatography using DCM:MeOH (0 to 7%).

TABLE 3

Test results of three ligands

| Entry | Catalyst | Ligand | time | % Product | % SM | % vinyl phenol | % ethyl phenol | % Bpin product ? | Total % |
|---|---|---|---|---|---|---|---|---|---|
| 1 | $NiCl_2$ | dppf | 17-20 h | 43 | 27 | 0 | 0 | 27 | 96 |
| | | | After wrk-up | 42 | 26 | 0 | 0 | 20 | 87 |
| 2 | $Ni(Acac)_2$ | dppf | 17-20 h | 7 | 46 | 1 | 0 | 33 | 86 |
| | | | After wrk-up | 7 | 44 | 1 | 0 | 24 | 76 |
| 3 | $Ni(COD)_2$ | dppf | 17-20 h | 3 | 41 | 0 | 1 | 25 | 70 |
| | | | After wrk-up | 2 | 50 | 0 | 0 | 24 | 77 |
| 4 | $NiCl_2$ | diPrf | 17-20 h | 63 | 1 | 0 | 0 | 32 | 96 |
| | | | After wrk-up | 69 | 1 | 0 | 0 | 28 | 98 |
| 5 | $Ni(acac)_2$ | diPrf | 17-20 h | 9 | 44 | 3 | 0 | 28 | 84 |
| | | | After wrk-up | 10 | 49 | 6 | 0 | 25 | 89 |
| 6 | $Ni(COD)_2$ | diPrf | 17-20 h | 5 | 51 | 2 | 0 | 28 | 86 |
| | | | After wrk-up | 8 | 57 | 3 | 0 | 22 | 90 |
| 7 | $Ni(Acac)_2$ | dcype | 17-20 h | 67 | 0 | 2 | 0 | 28 | 97 |
| | | | After wrk-up | 76 | 0 | 1 | 0 | 18 | 95 |
| 8 | $Ni(Acac)_2$ | dcype | After wrk-up—duplo | 71 | 1 | 1 | 0 | 23 | 96 |
| 9 | $Ni(COD)_2$ | dcype | 17-20 h | 51 | 13 | 3 | 1 | 30 | 98 |
| | | | After wrk-up | 55 | 13 | 3 | 2 | 25 | 98 |
| 10 | $Ni(COD)_2$ | dcype | After wrk-up—duplo | 52 | 20 | 3 | 1 | 20 | 96 |
| 11 | $NiCl_2$ | dcype | After wrk-up | 16 | 51 | 3 | 0 | 24 | 93 |

The results of the catalytic tests are reported in the table 4 below in area %.

TABLE 4

Test results of two ligands

| | Entry | Solvent | Area % (SM) | Area % (P) | Area % (vinyl-phneol) | Area % (peak at 8.1 min) |
|---|---|---|---|---|---|---|
| NiCl₂/diPrf | 12 | 18 h | 19 | 80 | 0 | 0 |
| | | After work-up | 19 | 78 | 0 | 0 |
| | 4 | Exp 4 (after work-up) | 1 | 97 | 0 | nd |
| Ni(Acac)₂/diPrf | 13 | 18 h | 25 | 70 | 1 | 1 |
| | | After work-up | 23 | 70 | 4 | 2 |
| | 7 | Exp 7 (after work-up) | 0 | 94 | 1 | nd |

For both reactions, the HPLC chromatograms were relatively clean. In the case of NiCl₂/diPrf, a small amount of the vinyl-phenol (peak at 11.63 min) was observed. It was also present with Ni(Acac)₂/dcype as well as some diboronate. By quantitative HPLC (using the calibration curve), the amount of desired product 2 obtained after work-up was determined for NiCl₂/diPrf yield=75% (HPLC=78% area).

The material produced in NiCl₂/diPrf was isolated via column chromatography (SiO₂, DCM:MeOH as eluent) resulting in 302 mg of a thick and yellowish oil—i.e. a higher mass than expected for a 100% yield (283 mg). ¹H NMR showed the presence of a large amount of pinacol/pinacol compounds in addition of the expected product. A second work-up consisting in dissolving the sample into a mixture of Et₂O/pentane followed by the addition of HCl 1M+stirring at 0° C. for 90 min was done. After isolation of the organic phase, 274 mg of a thick less yellowish oil was obtained. ¹H NMR showed that a significant amount of the pinacol/pinacol compounds was removed but not entirely. The same work up was repeated one more time (longer stirring: 18 h) yielding 223 mg of very thick pale oil. ¹H NMR showed that most of the pinacol/pinacol compounds were removed but some hydrolysis of the ester took place (about 20%). An overall isolated yield of 78% was obtained, which was consistent with the HPLC measurements.

Although a HPLC chromatogram of the material after the standard acidic work-up and column showed only 1 peak at the expected retention time for Compound 2, the 1H NMR spectrum of the same material seemed to indicate that 2 compounds were present: Compound 2 and a possibly pinacol-adduct of Compound 2 (either ring-closed or open).

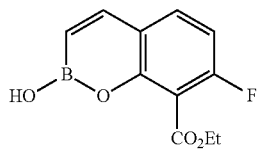

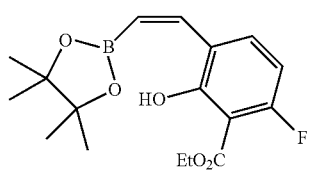

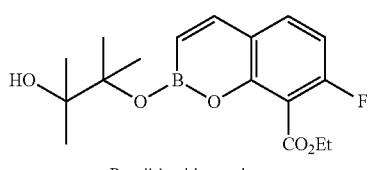

Possible side product

Reactions were performed with benzofuran substrate (0.3 mmol; 62.4 mg) at 10 mol % Ni catalyst.

TABLE 5

Test results for various solvents used in the Ni catalyst system

| | Entry | Solvent | Area % (SM) | Area % (P) | Area % (vinylphneol) |
|---|---|---|---|---|---|
| NiCl₂/diPrf | O1 | THF | 31 | 57 | 4 |
| | O2 | CH₂Cl₂ | 100 | | |
| | O3 | Chlorobenzene | 43 | 54 | 1 |
| | O4 | AcOEt | 34 | 58 | 2 |
| | O5 | Toluene | 23 | 75 | 1 |
| Ni(Acac)₂/dcype | O6 | THF | 23 | 70 | 2 |
| | O7 | CH₂Cl₂ | 84 | 5 | 1 |
| | O8 | Chlorobenzene | 60 | 29 | 1 |
| | O9 | AcOEt | 30 | 62 | 2 |
| | O10 | Toluene | 26 | 70 | 1 |

*SM (Starting material); P (product-compound 2); side product -vinylphneol

For Ni(Acac)₂/dcype, Toluene (O10) and TH (O6) gave similar results—not far behind EtOAc (O9). In case of the NiCl₂/diPrf, Toluene (O5) was better than THF (O1)/AcOEt (O4).

Example 6

In the N₂ glovebox, the Ni precursor (0.015; 0.03 or 0.06 mmol, 5; 10 and 20 mol % respectively) and the ligand (0.0175; 0.035 and 0.07 mmol, 1.17 eq/Ni) were placed inside a vial equipped with a magnetic stirrer. Toluene (0.75 mL) was added and the vial was capped. The vials were taken outside the glovebox and placed inside the reactor. Under N₂ (3 bar), the vials were stirred at 90° C. for 1 h.

Reaction procedure: In the N₂ glovebox, Cs₂CO₃ (0.9 mmol; 293 mg) and B₂(Pin)₂ (0.46 mmol; 117 mg) were added in a vial equipped with a magnetic stirrer. The catalyst solution was next added as well as 0.75 mL of toluene. Finally, the benzofuran substrate (0.3 mmol; 62.5 mg) was added. The vials were capped and taken outside the glovebox. The vials were placed inside the A96 reactor and kept under a flow of $N_2$ (3 bar). The vials were stirred at 90° C. for 17 h.

Reaction work up (outside of the glovebox): To the reaction mixture $Et_2O$ (1 mL) was added. $H_2O$ (1 mL) was added and HCl 6N was added until pH=1 (ca 0.3 mL). The mixture was stirred at 0° C. for 30 min. Then, the organic phase was extracted, dried with sodium sulphate, filtered and the solvent removed in vacuum. The sample was subjected to HPLC analysis (in MeCN and a small amount of Toluene as solvent).

Stirring rate: The two catalysts $Ni(acac)_2$/dcype and $NiCl_2$/diPrf were tested at different catalyst loadings (5, 10 and 20 mol %) in the parallel reactor. Although both reactor unit used the same vials and magnetic stirrer, the stem block system allows stirring speed up to 1000 rpm (750 rpm was used) while in the A96, the maximum stirring speed is 300 rpm.

Background reaction: In addition, unligated nickel salts at 10 mol % loading were also tested as blank reactions.

Ligands with various Ni precursors: 3 Ni precursors ($NiC_2$, $Ni(acac)_2$ and $Ni(COD)_2$) were combined with the ligands (4 bidentate phosphines and 1 monodentate phosphine) and tested at 5 mol % catalyst loading.

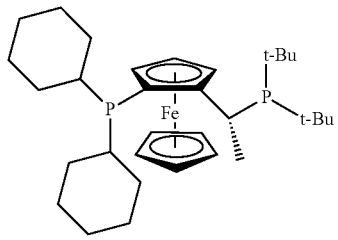

JosiPhos 9-1

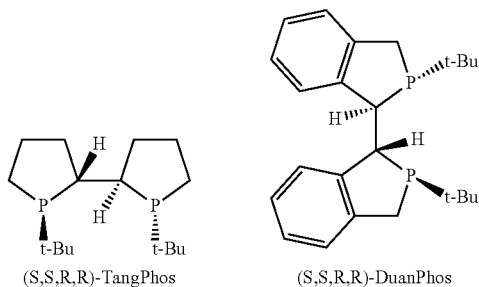

(S,S,R,R)-TangPhos     (S,S,R,R)-DuanPhos

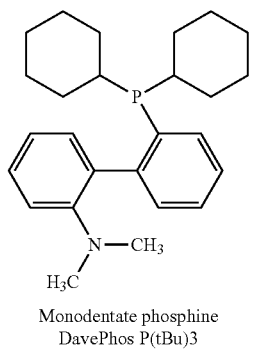

Monodentate phosphine
DavePhos P(tBu)3

Reaction condition: Ni (5, 10, 20 mol %); Ligand (1.2 eq/Ni); Compound 1 (0.3 mmol); $Cs_2CO_3$ (3 eq/Compound 1); $B_2Pin_2$ (1.5 eq/Compound 1); Toluene (1.5 mL); 90° C., 18 h. The Catalyst loading for the non-ligated catalyst was 10 mol % and for the ligand was 5 mol %

TABLE 6

Test results of various Ni precursor and ligand combinations

| Entry | Metal | Ligand | Area % (SM) | Area % (P) | Area % (vinylphenol) |
|---|---|---|---|---|---|
| 1 | Ni(acac)2 | dcype (5 m %) | 62 | 28 | 1 |
| 2 | Ni(acac)2 | dcype (10 m %) | 56 | 36 | 1 |
| 3 | Ni(acac)2 | dcype (20 m %) | 32 | 60 | 1 |
| 4 | Ni(acac)2 | dcype (20 m %) |  | 97 | 2 |
| 5 | NiCl2 | diPrf (5 m %) | 56 | 33 | 3 |
| 6 | NiCl2 | diPrf (10 m %) | 38 | 53 | 5 |
| 7 | NiCl2 | diPrf (20 m %) | 23 | 64 | 8 |
| 8 | NiCl2 | diPrf (20 m %) | 1 | 96 |  |
| 9 | NiCl2 |  | 99 |  |  |
| 10 | Ni(acac)2 |  | 77 | 9 |  |
| 11 | Ni(COD)2 |  | 95 |  |  |
| 12 | NiCl2 | Josiphos 9-1 | 79 | 3 | 4 |
| 13 | Ni(acac)2 | Josiphos 9-1 | 83 | 3 | 4 |
| 14 | Ni(COD)2 | Josiphos 9-1 | 83 | 5 | 3 |
| 15 | NiCl2 | (S,S,R,R)-TangPhos | 100 |  |  |
| 16 | Ni(acac)2 | (S,S,R,R)-TangPhos | 96 |  |  |
| 17 | Ni(COD)2 | (S,S,R,R)-TangPhos | 62 | 24 | 3 |
| 18 | NiCl2 | DuanPhos | 97 |  |  |
| 19 | Ni(acac)2 | DuanPhos | 87 | 4 | 1 |
| 20 | Ni(COD)2 | DuanPhos | 81 | 12 | 3 |
| 21 | NiCl2 | DavePhos | 89 | 3 |  |
| 22 | Ni(acac)2 | DavePhos | 92 |  |  |
| 23 | Ni(COD)2 | DavePhos | 87 | 5 |  |
| 24 | NiCl2 | P(tBu)3 | 100 |  |  |
| 25 | Ni(acac)2 | P(tBu)3 | 96 |  |  |
| 26 | Ni(COD)2 | P(tBu)3 | 86 | 5 |  |

*SM (Starting material); P (product-compound 2); side product -vinylphneol

For both catalysts (Ni(acac)₂/dcype and NiCl₂/diPrf), the conversion did not vary linearly with the catalyst loading indicating a rapid catalyst deactivation (Entry 1 to 3; Entry 5 to 7). A small amount of product was obtained with unligated Ni(acac)₂ at 10 mol %—however much less than in presence of a ligand: No ligand: 9%; dcype: 36%.

Among the bidentate ligands tested, the Ni(COD)₂/(S,S,R,R)-TangPhos system gave a conversion comparable to the one of the Ni(acac)₂/dcype system at 5 mol % loading—confirming that electron-rich bulky phosphines were good ligands for this transformation.

Example 7

Several ligands were combined with the nickel precursors Ni(acac)₂ and Ni(COD)₂ (See Table 7). In addition, a mixed phosphine-phosphite and a monodentate phosphoramidite were also included. 3 complexes based on other metal (Ru, Pd, Rh) were also tested. All the 18 reactions were performed in the standard conditions at 5 mol % catalyst loading.

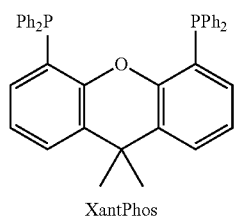

XantPhos

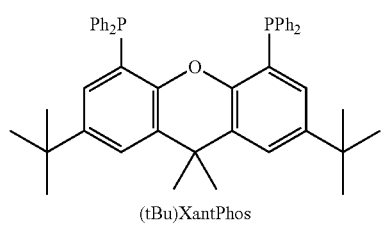

(tBu)XantPhos

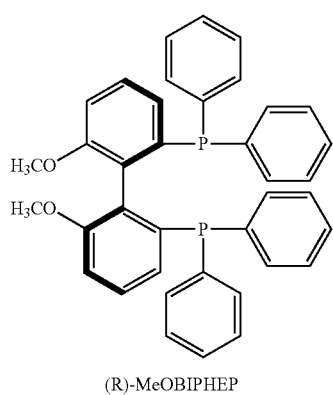

(R)-MeOBIPHEP

-continued

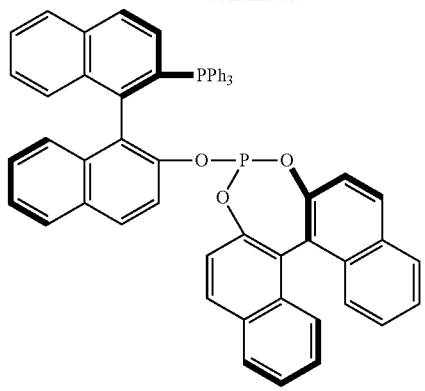

(R,S)-BinaPhos

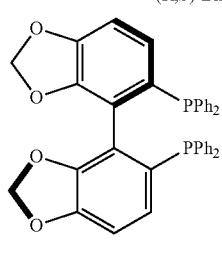

(R)-SegPhos

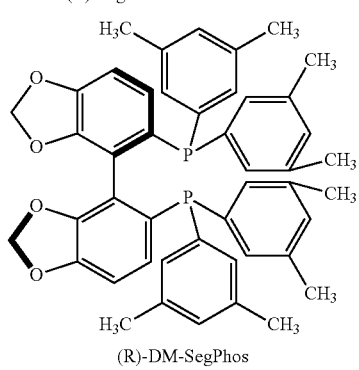

(R)-DM-SegPhos

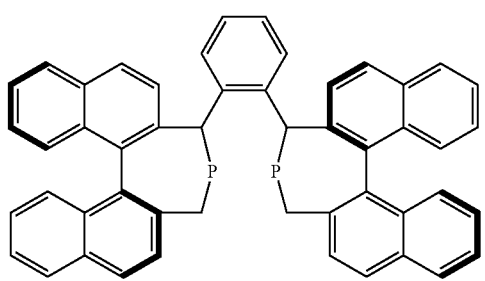

Binaphane

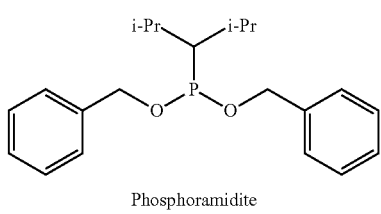

Phosphoramidite

TABLE 7

Test results summary based on HPLC analaysis

| Entry | Metal | Ligand | Area % (SM) | Area % (P) | Area % (vinylphenol) |
|---|---|---|---|---|---|
| LS33 | Ni(acac)2 | dcype (5 m %) | 62 | 28 | 1 |
| LS36 | NiCl2 | diPrf (5 m %) | 56 | 33 | 3 |
| LS57 | Ni(acac)2 | Xantphos | 88 | 6 | |
| LS58 | Ni(COD)2 | Xantphos | 89 | 2 | |
| LS59 | Ni(acac)2 | (tBu)Xantphos | 85 | 12 | |
| LS60 | Ni(COD)2 | (tBu)Xantphos | 91 | 2 | |
| LS61 | Ni(acac)2 | (R)-SegPhos | 82 | 17 | |
| LS62 | Ni(COD)2 | (R)-SegPhos | 71 | | |
| LS63 | Ni(acac)2 | (R)-DM-SegPhos | 71 | 22 | 1 |
| LS64 | Ni(COD)2 | (R)-DM-SegPhos | 81 | 11 | |
| LS65 | Ni(acac)2 | (S)-MeOBiPhep | 76 | 4 | 1 |
| LS66 | Ni(COD)2 | (S)-MeOBiPhep | 62 | 18 | |
| LS67 | Ni(acac)2 | (R,S)-BinaPhos | 89 | 2 | |
| LS68 | Ni(COD)2 | (R,S)-BinaPhos | 91* | 3 | |
| LS69 | Ni(COD)2 | (S)-Binaphane | 94 | 1 | |
| LS71 | Ni(acac)2 | Phosphoramidite | 96* | | 2 |
| LS72 | Ni(COD)2 | Phosphoramidite | 99 | | |

\* Area calculated as the sum of two overlapped peaks;
\*SM (Starting material); P (product-compound 2); side product -vinylphneol The dcype or diPrf system produced good results. Bulky electron-rich phosphines like SegPhos, DM-SegPhos and MeOBIPHEP in combination with Ni(COD)$_2$ (entries LS62 and LS66) or Ni(acac)$_2$ (LS64) yielded the benzoxaborin product 1 with better conversions than with the trans-spanning ligands.

Example 8

A set of bulky electron rich ligands shown below in combination with Ni(acac)$_2$ and Ni(COD)$_2$ were tested in the stem block i.e. with a more efficient stirring. The reactions were run using conditions described in Example 5.

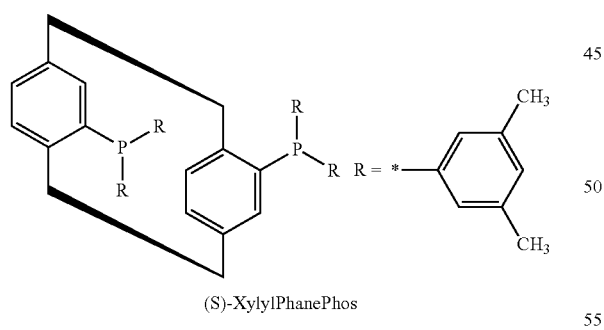

(S)-XylylPhanePhos

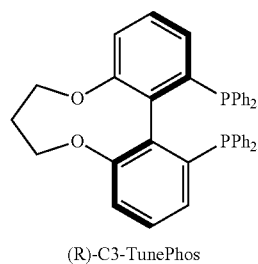

(R)-C3-TunePhos

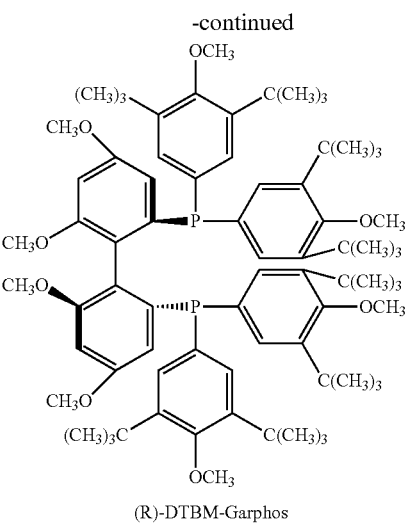

(R)-DTBM-Garphos

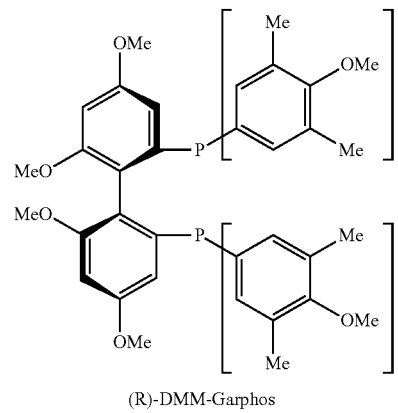

(R)-DMM-Garphos

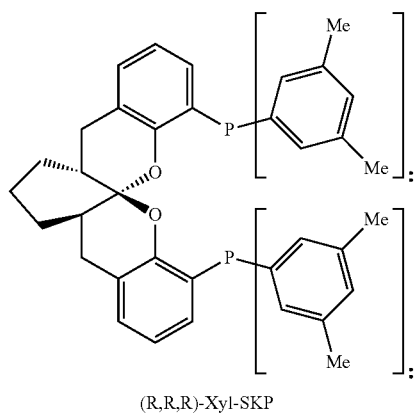

(R,R,R)-Xyl-SKP

TABLE 8

Summary of test results based on HPLC analysis

| Entry | Metal | Ligand | Area % (SM) | Area % (P) | Area % (vinylphenol) |
|---|---|---|---|---|---|
| | $NiCl_2$ (10 mol %) | diPrf | 38 | 58 | 3 |
| | Ni(acac) (15 mol %) | dcype | 25 | 70 | 1 |
| LS75 | Ni(acac)2 | (S)-XylylPhanePhos | 95* | | 2 |
| LS76 | Ni(COD)2 | (S)-XylylPhanePhos | 84* | 3 | 3 |
| LS77 | Ni(acac)2 | (R)-C3-TunePhos | 74* | | 4 |
| LS78 | Ni(COD)2 | (R)-C3-TunePhos | 73 | 13 | 2 |
| LS79 | Ni(acac)2 | (R)-DTBM-GarPhos | 97* | | |
| LS80 | Ni(COD)2 | (R)-DTBM-GarPhos | 75 | 9 | 3 |
| LS81 | Ni(acac)2 | (R)-DMM-GarPhos | 94 | 4 | 1 |
| LS82 | Ni(COD)2 | (R)-DMM-GarPhos | 31 | 67 | 1 |
| LS83 | Ni(acac)2 | (R,R,R)-Xyl-SKP | 96* | | 2 |
| LS84 | Ni(COD)2 | (R,R,R)-Xyl-SKP | 82 | 6 | 2 |

*Area calculated as the sum of two overlapping peaks; SM—staring material; P—product compound 2

Among all the ligands tested, the electron-rich (R)-DMM-GarPhos in combination with $Ni(COD)_2$ (LS82) afforded compound 2 in 67% area in a clean chromatogram.

Additional tests using DiPrf and dcype at lower catalyst loading were performed. The same procedure as described in Example 5 with a total of 3 equivalents base/substrate in two different solvents: THF for $Ni(Acac)_2$/dcype and Toluene for $NiCl_2$/diPrf. Reactions were run with benzofuran substrate (0.3 mmol; 62.4 mg) at 10 mol % Ni catalyst.

TABLE 9

Analysis of reactions using various base combinations

| | Entry | Base | Area % (SM) | Area % (P) | Area % (vinyl-phenol) | Area % (peak at 8.1 min) |
|---|---|---|---|---|---|---|
| $NiCl_2$/diPrf | 011 | $Li_2CO_3$ | 100 | | | |
| Solvent: | 012 | $Li_2CO_3/Cs_2CO_3$ 9/1 | 44 | 42 | 12 | |
| Toluene | 013 | $K_2CO_3$ | 80 | 9 | 7 | |
| | 014 | $K_2CO_3/Cs_2CO_3$ 9/1 | 78 | 13 | 5 | |
| | 015 | $K_2CO_3/Li_2CO_3$ 9/1 | 80 | 9 | 6 | |
| $Ni(acac)_2$/ | 016 | $Li_2CO_3$ | 12 | 68 | 2 | |
| dcype | 017 | $Li_2CO_3/Cs_2CO_3$ 9/1 | 42 | 53 | 1 | 1 |
| Solvent: | 018 | $K_2CO_3$ | 27 | 62 | 1 | 6 |
| THF | 019 | $K_2CO_3/Cs_2CO_3$ 9/1 | 24 | 71 | 1 | 2 |
| | 020 | $K_2CO_3/Li_2CO_3$ 9/1 | 39 | 47 | 1 | 8 |

*SM (Starting material); P (product-compound 2); side product -vinylphneol and peak at 8.1 min For $NiCl_2$/diPrf in Toluene, the combination of $Li_2CO_3$/$Cs_2CO_3$ (9:1) gave 42 area % of desired product (compared to 75 area % with $Cs_2CO_3$). For $Ni(Acac)_2$/dcype in THF, several bases/base combination gave conversion very similar to the one obtained with $Cs_2CO_3$ with low amount of side-products: $K_2CO_3$/$Cs_2CO_3$ (9:1) (O19); $Li_2CO_3$ (O16); $K_2CO_3$ (O18).

Example 9

The activities of catalysts dcype, DiPrf and (R)-DMM-GarPhos are summarized in table 10.

TABLE 10

Summary of the activities of dcype, DiPrf and (R)-DMM-Garphos

| Entry | Metal | Ligand | S/C (mol %) | Area % (SM) | Area % (P) | Area % (vinyl-phenol) |
|---|---|---|---|---|---|---|
| LS33 (A96) | $Ni(acac)_2$ | dcype | 5 | 62 | 28 | 1 |
| 28 (StemBlock) | $Ni(acac)_2$ | dcype | 20 | 0 | 97 | 2 |

TABLE 10-continued

Summary of the activities of dcype, DiPrf and (R)-DMM-Garphos

| Entry | Metal | Ligand | S/C (mol %) | Area % (SM) | Area % (P) | Area % (vinyl-phenol) |
|---|---|---|---|---|---|---|
| LS36 (A96) | NiCl2 | diPrf | 5 | 56 | 33 | 3 |
| 25 | NiCl2 | diPrf | 20 | 1 | 96 | |
| LS82 (A96) | $Ni(COD)_2$ | (R)-DMM-Garphos | 5 | 31 | 67 | 1 |

*SM (Starting material); P (product-compound 2); side product -vinylphneol

The $Ni(COD)_2$ and $Ni(acac)_2$ precursors were combined with three ligands: Thio-XantPhos, a more electron-rich variant of the XantPhos ligand, the bulky and electron-rich TaniaPhos and the trans-spanning ligand SPANPhos (shown below).

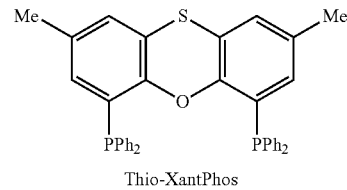

Thio-XantPhos

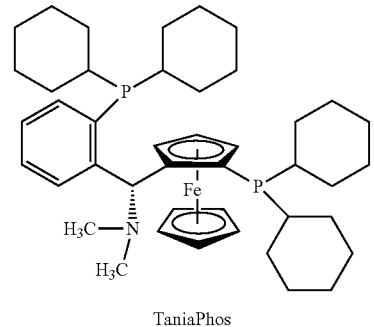

TaniaPhos

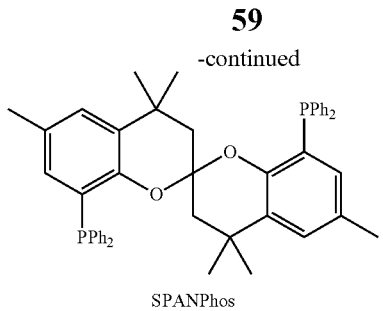

SPANPhos

In the $N_2$ glovebox, the Ni precursor (0.015 mmol, 5 mol %) and the ligand (0.0175; mmol, 1.17 eq/Ni) were placed inside a vial equipped with a magnetic stirrer. Toluene (0.75 mL) was added and the vial was capped. The vials were placed in the stem block and stirred at 90° C. for 1 h.

In the $N_2$ glovebox, $Cs_2CO_3$ (0.9 mmol; 293 mg) and $B_2(Pin)_2$ (0.46 mmol; 117 mg) were added in a vial equipped with a magnetic stirrer. The catalyst solution was next added as well as 0.75 mL of toluene. Finally, the benzofuran substrate (1.2 mmol; 250 mg) was added. The vials were capped and placed in the stem block. The vials were stirred at 90° C. for 17 h.

Reaction work up (outside of the glovebox): To the reaction mixture $Et_2O$ (1 mL) was added. $H_2O$ (1 mL) was added and HCl 6N was added until pH=1 (ca 0.3 mL). The mixture was stirred at 0° C. for 30 min. Then, the organic phase was extracted, dried with sodium sulphate, filtered and the solvent removed in vacuo. The sample was subjected to HPLC analysis (in MeCN and a small amount of Toluene as solvent). The results are summarized in Table 11. The reactions using $Ni(COD)_2$/TaniaPhos produced compound 2 in good yields.

TABLE 11

Analysis of the test results

| Entry | Metal | Ligand | Area % (SM) | Area % (P) | Area % (vinylphenol) |
|---|---|---|---|---|---|
| LS33 | Ni(acac)2 | dcype (5 m %) | 62 | 28 | 1 |
| LS36 | NiCl2 | diPrf (5 m %) | 56 | 33 | 3 |
| LS82 | Ni(COD)2 | (R)-DMM-Garphos | 31 | 67 | 1 |
| LS85 | Ni(acac)2 | Thio-Xantphos | 79 | 1 | 2 |
| LS86 | Ni(COD)2 | Thio-Xantphos | 96 | | |
| LS87 | Ni(acac)2 | TaniaPhos | 78 | 5 | 1 |
| LS88 | Ni(COD)2 | TaniaPhos | 52 | 38 | 5 |
| LS89 | Ni(acac)2 | SPANPhos | 97 | | 1 |
| LS90 | Ni(COD)2 | SPANPhos | 91 | | 1 |

*SM (Starting material); P (product-compound 2); side product -vinylphneol

Example 10

Studies using $PPh_3$ in presence Zn powder and iodide were also performed. Zn powder and halide additives have been used in homo- and cross-coupling reaction of aryl halides in presence of $Ni/PPh_3$ systems. Zn is acting as a reducing agent while the halide stabilizes $Ni^0$ via the formation of penta-coordinate nickelate intermediates as described in Chem Rev 2011, 111(3): 1346-1416, which is incorporated herein by reference. Two additives (Zn, $Bu_4NI$) in two different solvents with two Ni precursors were tested.

$NiCl_2(PPh_3)_3$ was selected as metal precursor as in the presence of $Zn^0$ is known to generate $Ni(PPh_3)_3$ which is an active catalyst for C—O and C—X bond activation. An excess of $PPh_3$ was also added since $PPh_3$ can dissociate from the $Ni^0$ complex due to the steric constraints. $NiCl_2$ was also investigated as a metal precursor in combination with $PPh_3$ as stabilizing ligand under analogue reaction condition (see table below).

Reaction procedure: In the $N_2$ glovebox, $Bu_4NI$ (0.45 mmol; 166 mg); $B_2(Pin)_2$ (0.46 mmol; 117 mg) and zinc (0.9 mmol; 59 mg) were added in a vial equipped with a magnetic stirrer. $NiCl_2(PPh_3)_3$ (0.03 mmol; 20 mg) or $NiCl_2$ (0.03 mmol; 4 mg) and $PPh_3$ (0.0; 0.06; 0.12 or 0.18 mmol) were added to the reaction. Solvent (1.5 mL) and the benzofuran substrate (0.3 mmol; 250 mg) were finally added. The vials were capped and placed in the stem block. The vials were stirred at 90° C. for 17 h. The results are compiled in the table below (in area % of product).

TABLE 12

Summary of test results based on HPLC analysis

| Reaction | Metal salt (10 mol %) | $PPh_3$ | Solvent | Area % (SM) | Area % (P) |
|---|---|---|---|---|---|
| LS105 | NiCl2(PPh3)2 | 0 | Toluene | 79 | |
| LS106 | NiCl2(PPh3)2 | 0 | THF | 82 | |
| LS107 | NiCl2(PPh3)2 | 2 eq/Ni | Toluene | 77 | |
| LS108 | NiCl2(PPh3)2 | 2 eq/Ni | THF | 86 | 1 |
| LS109 | NiCl2(PPh3)2 | 4 eq/Ni | Toluene | 72 | |
| LS110 | NiCl2(PPh3)2 | 4 eq/Ni | THF | 79 | 1 |
| LS111 | NiCl2 | 4 eq/Ni | Toluene | 82 | |
| LS112 | NiCl2 | 4 eq/Ni | THF | 81 | 1 |
| LS113 | NiCl2 | 6 eq/Ni | Toluene | 78 | |
| LS114 | NiCl2 | 6 eq/Ni | THF | 78 | |

*SM (Starting material); P (product-compound 2); side product -vinylphneol

Two catalyst dppf and $P(tBu)_3$ in presence of $Zn/I^-$ were tested. A similar set of reactions with $Zn/I^-$ as additives was performed with $NiCl_2$/dppf and $NiCl_2/P(tBu)_3$. $K_2CO_3$ was also added in some reaction.

Reaction procedure: In the $N_2$ glovebox, $Bu_4NI$ (0.45 mmol; 166 mg); $K_2CO_3$ (0.9 mmol; 124 mg); $B_2(Pi)_2$ (0.46 mmol; 117 mg) and zinc (0.9 mmol; 59 mg) were added in a vial equipped with a magnetic stirrer. $NiCl_2(dppf)$ (0.03 mmol; 20 mg) or $NiCl_2$ (0.03 mmol; 4 mg) and $PPh_3/P(tBu)_3$ (0.0; 0.06; 0.12 or 0.18 mmol) were added to the reaction. Solvent (1.5 mL) and the benzofuran substrate (0.3 mmol; 250 mg) were finally added. The vials were capped and placed in the stem block. The vials were stirred at 90° C. for 17 h. The results are compiled in Table 13 (in area % of product).

TABLE 13

Summary of test results based on HPLC analysis

| # | Metal salt (10 mol %) | Ligand | Base | Solvent | Area % (SM) | Area % (P) | Area % (vinyl-phenol) |
|---|---|---|---|---|---|---|---|
| LS115 | NiCl2 (dppf) | | | Toluene | 58 | 1 | 8 |
| LS116 | NiCl2 (dppf) | | | THF | 71 | | 2 |
| LS117 | NiCl2 (dppf) | | K2CO3 | Toluene | 57 | 6 | 5 |
| LS118 | NiCl2 (dppf) | | K2CO3 | THF | 42 | 32 | 2 |
| LS119 | NiCl2 | P(tBu)3 (40 mol %) | | Toluene | 98 | 1 | 1 |
| LS120 | NiCl2 | P(tBu)3 (40 mol %) | | THF | 92 | 1 | 1 |
| LS121 | NiCl2 | P(tBu)3 (40 mol %) | K2CO3 | Toluene | 93 | 6 | 1 |
| LS122 | NiCl2 | P(tBu)3 (40 mol %) | K2CO3 | THF | 87 | 4 | 1 |
| LS123 | NiCl2 | PPh3 (40 mol %) | K2CO3 | Toluene | 60 | 9 | 1 |
| LS124 | NiCl2 | PPh3 (40 mol %) | K2CO3 | THF | 76 | 10 | 1 |

*SM (Starting material); P (product-compound 2); side product -vinylphneol

In THF, a significant amount of product (32%) was obtained with the NiC$_2$(dppf) catalyst when all the additives (I$^-$ source, base, Zn powder) were present in the reaction. NiCl$_2$/dppf was tested before at 20 mol % in presence of 3 eq of CsCO$_3$ in Tol yielding 43% area of product.

Example 11

All reactions were performed on 3 stem blocks placed inside the glovebox. Up to 30 reactions can be performed with this set up with a stirring speed of 750 rpm.

Catalyst preparation: In the N$_2$ glovebox, the Ni precursor (0.015 mmol, 5 mol %) and the ligand (0.0175; mmol, 1.17 eq/Ni) were placed inside a vial equipped with a magnetic stirrer. Toluene (0.75 mL) was added and the vial was capped. The vials were placed in the stem block and stirred at 90° C. for 1 h.

Reaction procedure: In the N$_2$ glovebox, Cs$_2$CO$_3$ (0.9 mmol; 293 mg) and B$_2$(Pin)$_2$ (0.46 mmol; 117 mg) were added in a vial equipped with a magnetic stirrer. The catalyst solution was next added as well as 0.75 mL of toluene. Finally, the benzofuran substrate (0.3 mmol; 62 mg) was added. The vials were capped and placed in the stem block. The vials were stirred at 90° C. for 17 h.

Reaction work up (outside of the glovebox): To the reaction mixture Et$_2$O (1 mL) was added. H$_2$O (1 mL) was added and HCl 6N was added until pH=1 (ca 0.3 mL). The mixture was stirred at 0° C. for 30 min. Then, the organic phase was extracted, dried with sodium sulphate, filtered and the solvent removed in vacuo. The sample was subjected to HPLC analysis (in MeCN and a small amount of Toluene as solvent).

The catalyst efficiency can be dependent on both the phosphine ligand and the nickel precursor. The study tested combining new phosphines related to the ones giving a high activity with affordable nickel precursors under standard reaction conditions (1.5 eq of B$_2$Pin$_2$, 3 eq of Cs$_2$CO$_3$, toluene, 90° C.). All the reactions were performed using a catalyst loading of 5 mol % in order to clearly distinguish the differences in activities. Four nickel precursors NiCl$_2$; Ni(acac)$_2$; Ni(COD)$_2$ and NiCl$_2$(PPh$_3$)$_2$ and 18 ligands shown below were used in the reaction.

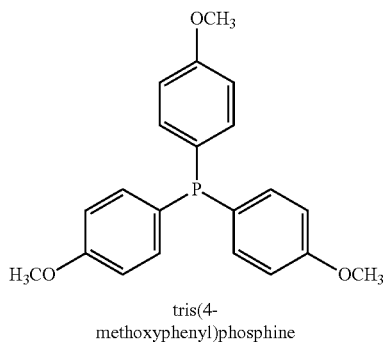

L1
tris(4-methoxyphenyl)phosphine

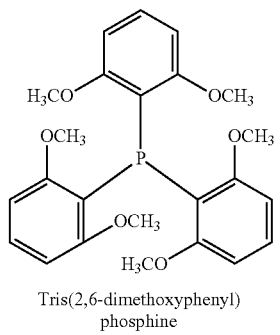

L2
Tris(2,6-dimethoxyphenyl) phosphine

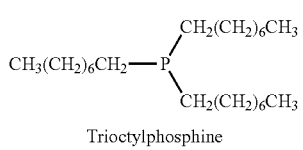

L3
Trioctylphosphine

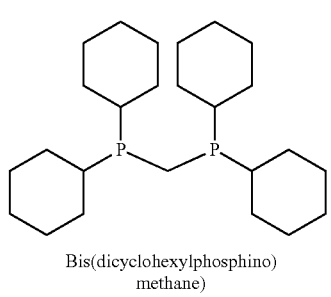

L4
Bis(dicyclohexylphosphino) methane)

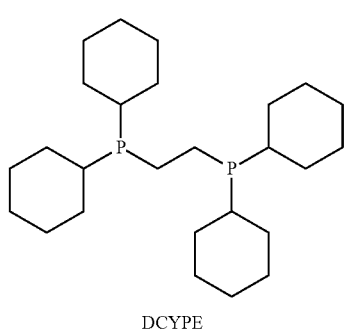

L5
DCYPE

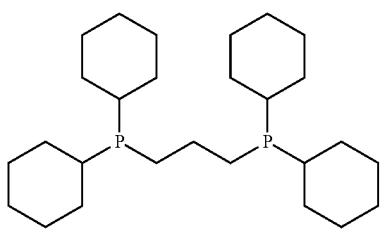
1,3-Bis(dicyclohexyl phosphino)propane
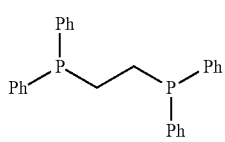
1,2-Bis(diphenyl phosphino)ethane
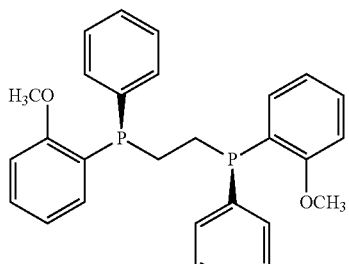
(R,R)-Dipamp
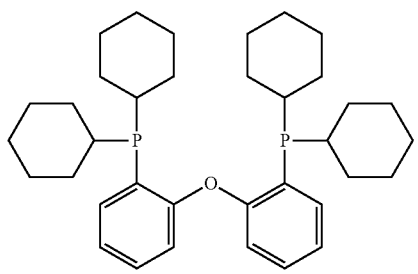
Bis(dicyclohexyl phosphinophenyl) ether
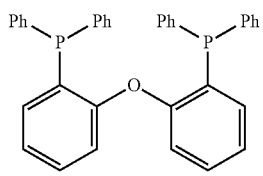
DPEPhos
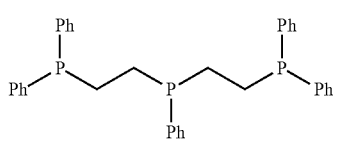
Bis(2-diphenylphosphino ethyl) Phenylphosphine
L6
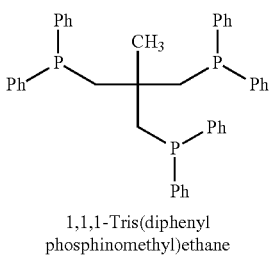
1,1,1-Tris(diphenyl phosphinomethyl)ethane
L7
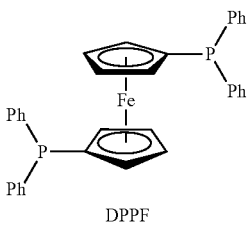
DPPF
L8
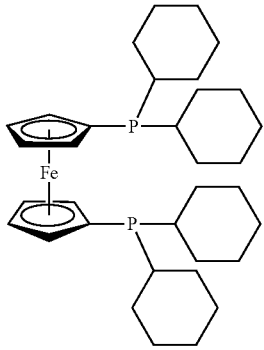
1,1'-Ferrocenediyl-bis(dicyclohexylphosphine)
L9
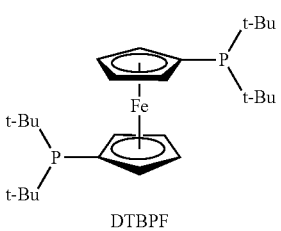
DTBPF
L10
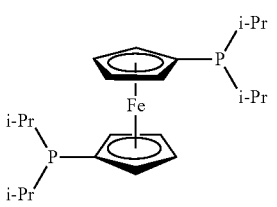
DiPrF
L11
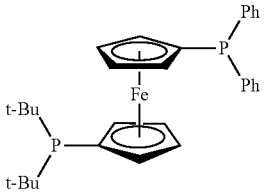
1-Diphenylphosphino-1'-(di-butylphosphino)ferrocene
L12
L13
L14
L15
L16
L17

-continued

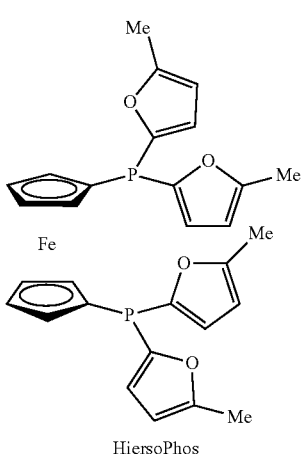

HiersoPhos

Reaction conditions: Ni salt (5 mol %); Ligand (1.17 equiv/Ni); Compound 1 (0.3 mmol); Cs2CO3 (3 equiv/Compound 1); B2Pin2 (1.5 equiv/Compound 1); Toluene (1.5 mL); 90° C., 20 h. Ligand loading: Monodentate ligand: 10 mol % (2.3 equiv/Ni); Bidentate ligand: 5 mol % (1.17 equiv/Ni). The test results are summarized in Table 14a-14d and also in FIG. 1. SM (Starting material); P (product-compound 2); side product—vinylphenol.

TABLE 14a

Test results (in area %) for NiCl$_2$ Precursor.

| Ligand | Area % (SM) | Area %(P) | Area % (vinylPhPH) |
|---|---|---|---|
| L1 | 94 | | 1 |
| L2 | 68 | 28 | 1 |
| L3 | 57 | 41 | 1 |
| L4 | 92 | 1 | 1 |
| L5 | 55 | 37 | 2 |
| L6 | 58 | 34 | 3 |
| L7 | 86 | | 1 |
| L8 | 91 | | |
| L9 | 72 | 13 | 5 |
| L10 | 71 | 2 | 4 |
| L11 | 90 | | |
| L12 | 98 | | |
| L13 | 48 | 41 | 1 |
| L14 | 23 | 75 | |
| L15 | 97 | | 1 |
| L16 | 37 | 58 | 3 |
| L17 | 77 | 1 | 1 |
| L18 | 91 | | |

TABLE 14b

Test results (in area %) for Ni(acac)$_2$ Precursor.

| Ligand | Area % (SM) | Area %(P) | Area % (vinylPhPH) |
|---|---|---|---|
| L1 | 95 | 1 | 1 |
| L2 | 71 | 24 | 1 |
| L3 | 96 | | 1 |
| L4 | 89 | 1 | 2 |
| L5 | 38 | 56 | 2 |
| L6 | 85 | 6 | 3 |
| L7 | 87 | | 1 |
| L8 | 89 | | 1 |
| L9 | 90 | 1 | 5 |
| L10 | 80 | | 4 |
| L11 | 90 | | 1 |
| L12 | 91 | | 1 |
| L13 | 76 | 1 | 2 |

TABLE 14b-continued

Test results (in area %) for Ni(acac)$_2$ Precursor.

| Ligand | Area % (SM) | Area %(P) | Area % (vinylPhPH) |
|---|---|---|---|
| L14 | 82 | 1 | 4 |
| L15 | 91 | | 1 |
| L16 | 79 | | 6 |
| L17 | 81 | | 2 |
| L18 | 96 | | |

TABLE 14c

Test results (in area %) for Ni(COD)$_2$ Precursor.

| Ligand | Area % (SM) | Area %(P) | Area % (vinylPhPH) |
|---|---|---|---|
| L1 | 94 | 1 | 1 |
| L2 | 74 | 21 | 1 |
| L3 | 87 | 3 | 3 |
| L4 | 79 | 13 | 2 |
| L5 | 50 | 43 | 3 |
| L6 | 83 | 9 | 3 |
| L7 | 83 | | 1 |
| L8 | 88 | | 1 |
| L9 | 64 | 31 | 1 |
| L10 | 84 | | 5 |
| L11 | 87 | | |
| L12 | 97 | | |
| L13 | 57 | 25 | |
| L14 | 81 | 12 | 3 |
| L15 | 85 | 9 | 1 |
| L16 | 73 | 15 | 5 |
| L17 | 80 | 9 | 1 |
| L18 | 96 | 2 | |

TABLE 14d

Test results (in area %) for NiCl$_2$(PPh$_3$)$_2$ Precursor.

| Ligand | Area % (SM) | Area %(P) | Area % (vinylPhPH) |
|---|---|---|---|
| L1 | 82 | | 2 |
| L2 | 55 | 27 | 2 |
| L3 | 51 | 32 | 2 |
| L4 | 64 | 15 | 2 |
| L5 | 42 | 38 | 2 |
| L6 | 33 | 52 | |
| L7 | 72 | | 1 |
| L8 | 73 | 1 | 2 |
| L9 | 69 | 2 | 4 |
| L10 | 64 | 2 | 3 |
| L11 | 73 | | |
| L12 | 74 | | 1 |
| L13 | 52 | 27 | 2 |
| L14 | 35 | 51 | 2 |
| L15 | 80 | | 2 |
| L16 | 42 | 44 | |
| L17 | 65 | 5 | 2 |
| L18 | 78 | | 1 |

Among the monodentate phosphines (L1-L3): L2 appeared to be active with all Ni precursors giving yields between 20-30 area % P. L5, dcype, also provided good yield when used in combination with Ni(Acac)$_2$. L6, dcypp, with a 3-carbon bridge, also showed good activity with NiCl$_2$(PPh$_3$)$_2$. L9 (forming either an 8-membered chelate with the metal or acting as a tridentate ligand) in combination with Ni(COD)$_2$ also achieved good yield.

In the ferrocene based ligands (L13-L18), dcypf and diPrpf (L16) both showed good activity.

Example 12

N-heterocyclic carbenes were tested in this study. Four nickel precursors investigated in module 2 ($NiC_2$; $Ni(acac)_2$; $Ni(COD)_2$ and $NiC_2(PPh_3)_2$) were combined with 3 carbene ligands shown below under standard reaction conditions (1.5 eq of $B_2Pin_2$, 3 eq of $Cs_2CO_3$, toluene, 90° C.). All the reactions were performed using a catalyst loading of 5 mol % in order to clearly distinguish the differences in activities.

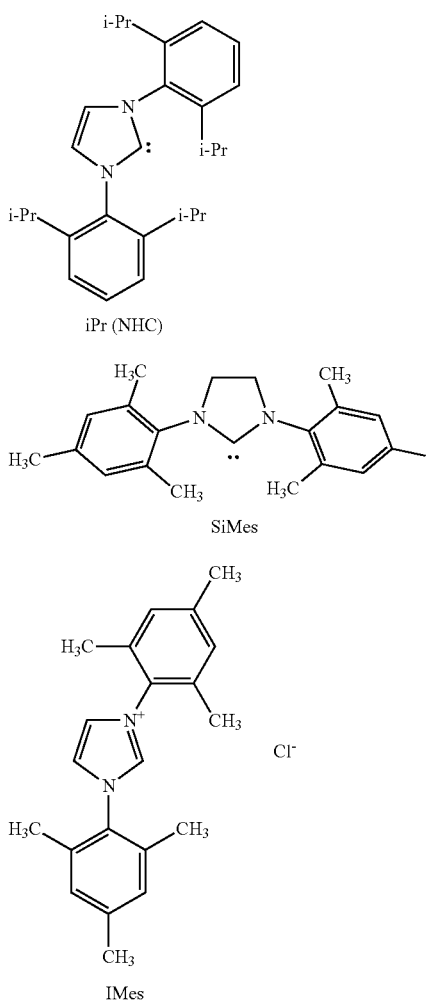

All the reactions were performed on 3 stem blocks placed inside the glovebox. Up to 30 reactions can be performed with this set up with a stirring speed of 750 rpm.

Catalyst preparation: In the $N_2$ glovebox, the Ni precursor (0.015 mmol, 5 mol %) and the ligand (0.0175; mmol, 1.17 eq/Ni) were placed inside a vial equipped with a magnetic stirrer. Toluene (0.75 mL) was added and the vial was capped. The vials were placed in the stem block and stirred at 90° C. for 1 h. For L21 in the table below, $Cs_2CO_3$ (1.2 eq/L) was added to deprotonate the carbene.

Reaction procedure: In the $N_2$ glovebox, $Cs_2CO_3$ (0.9 mmol; 293 mg) and $B_2(Pin)_2$ (0.46 mmol; 117 mg) were added in a vial equipped with a magnetic stirrer. The catalyst solution was next added as well as 0.75 mL of toluene. Finally, the benzofuran substrate (0.3 mmol; 62 mg) was added. The vials were capped and placed in the stem block. The vials were stirred at 90° C. for 17 h.

Reaction work up (outside of the glovebox): To the reaction mixture $Et_2O$ (1 mL) was added. $H_2O$ (1 mL) was added and HCl 6N was added until pH=1 (ca 0.3 mL). The mixture was stirred at 0° C. for 30 min. Then, the organic phase was extracted, dried with sodium sulphate, filtered and the solvent removed in vacuo. The sample was subjected to HPLC analysis (in MeCN and a small amount of Toluene as solvent).

Reaction conditions: Ni salt (5 mol %); Ligand (1.17 equiv/Ni); compound 1 (0.3 mmol); $Cs_2CO_3$ (3 equiv/1); $B_2Pin_2$ (1.5 equiv/1); Toluene (1.5 mL); 90° C., 20 h. The reaction results (in area %) are shown in the table below.

TABLE 15

Reaction results summary

| Ni precursor | Ligand | Area % (SM) | Area % (P) | Area % (vinylphenol) |
|---|---|---|---|---|
| $NiCl_2$ | L19 | 93 | | |
| | L20 | 80 | 9 | 3 |
| | L21 | 83 | 10 | 1 |
| $Ni(acac)_2$ | L19 | 89 | | |
| | L20 | 86 | 11 | |
| | L21 | 63 | 27 | 2 |
| $Ni(COD)_2$ | L19 | 84 | 7 | 1 |
| | L20 | 89 | 5 | 1 |
| | L21 | 59 | 28 | 1 |
| $NiCl_2(PPh_3)_2$ | L19 | 69 | 8 | |
| | L20 | 77 | 4 | 2 |
| | L21 | 81 | 3 | |

Example 13

Three ligands: L3, L13 and L14 (structure shown below) in combination with $NiCl_2$ as Ni precursor were subjected to the borylation reaction under standard conditions (1.5 eq of $B_2Pin_2$, 3 eq of $Cs_2CO_3$, toluene) using different catalyst loadings and temperatures.

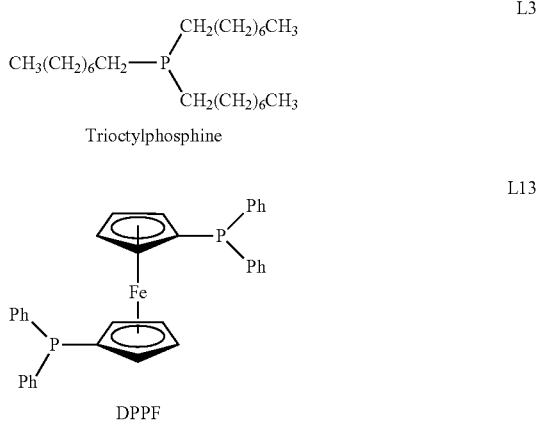

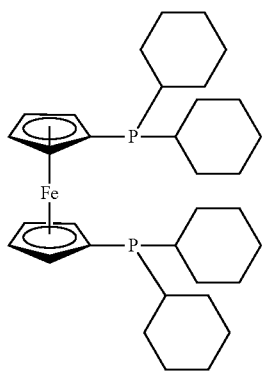

1,1′-Ferrocenediyl-bis (dicyclohexylphosphine)

The reaction conditions at 90° C. included Ni salt (5; 10 and 20 mol %); Ligand (1.17 equiv/Ni); Compound 1 (0.3 mmol); Cs$_2$CO$_3$ (3 equiv/1); B$_2$Pin$_2$ (1.5 equiv/1); Toluene (1.5 mL); 20 h. The reaction results at 90° C. is shown in Table 16. The reaction conditions at 100° C. included Ni salt (2.5; 5 and 10 mol %); Ligand (1.17 equiv/Ni); compound 1 (0.3 mmol); Cs$_2$CO$_3$ (3 equiv/1); B$_2$Pin$_2$ (1.5 equiv/1); Toluene (1.5 mL); 20 h. The reaction results at 100° C. is shown in Table 20. Ligand loading: Monodentate ligand (L3): (2.3 equiv/Ni); Bidentate ligands (L13, L14): (1.17 equiv/Ni).

TABLE 16

Reaction results at 90° C. (in area %)

| Ligand | Cat. load (mol %) | Area % (SM) | Area % (P) | Area % (vinylphenol) |
| --- | --- | --- | --- | --- |
| L3 | 5 | 57 | 40 | 3 |
| L3 | 10 | 39 | 58 | 1 |
| L3 | 20 | 12 | 83 | |
| L13 | 5 | 51 | 38 | |
| L13 | 10 | 43 | 45 | 1 |
| L13 | 20 | 25 | 55 | |
| L14 | 5 | 23 | 71 | 3 |
| L14 | 10 | 20 | 80 | |
| L14 | 20 | | >99 | |

*SM (Starting material); P (product-compound 2); side product -vinylphneol

TABLE 17

Reaction results at 100° C. (in area %)

| Ligand | Cat. load (mol %) | Area % (SM) | Area % (P) | Area % (vinylphenol) |
| --- | --- | --- | --- | --- |
| L3 | 2.5 | 96 | | 1 |
| L3 | 5 | 93 | 1 | 2 |
| L3 | 10 | 68 | 26 | 1 |
| L13 | 2.5 | 75 | 5 | 3 |
| L13 | 5 | 74 | 5 | 1 |
| L13 | 10 | 59 | 15 | |
| L14 | 2.5 | 90 | 6 | |
| L14 | 5 | 47 | 46 | |
| L14 | 10 | 10 | 87 | |

*SM (Starting material); P (product-compound 2); side product -vinylphneol

Example 14

All the reactions were performed on 3 stem blocks placed inside the glovebox. Up to 30 reactions can be performed with this set up with a stirring speed of 750 rpm.

In the N$_2$ glovebox, the Ni precursor (0.015 mmol, 5 mol %) and the ligand (0.0175; mmol, 1.17 eq/Ni) were placed inside a vial equipped with a magnetic stirrer. Toluene (0.75 mL) was added and the vial was capped. The vials were placed in the stem block and stirred at 90° C. for 1 h.

Reaction procedure: In the N$_2$ glovebox, Cs$_2$CO$_3$ (0.9 mmol; 293 mg) and B$_2$(Pin)$_2$ (0.46 mmol; 117 mg) were added in a vial equipped with a magnetic stirrer. The catalyst solution was next added as well as 0.75 mL of toluene. Finally, the benzofuran substrate (0.3 mmol; 62 mg) was added. The vials were capped and placed in the stem block. The vials were stirred at 90° C. for 17 h.

Reaction work up (outside of the glovebox): To the reaction mixture Et$_2$O (1 mL) was added. H$_2$O (1 mL) was added and HCl 6N was added until pH=1 (ca 0.3 mL). The mixture was stirred at 0° C. for 30 min. Then, the organic phase was extracted, dried with sodium sulphate, filtered and the solvent removed in vacuo. The sample was subjected to HPLC analysis (in MeCN and a small amount of Toluene as solvent).

The three selected ligands: L3 Trioctylphosphine, L13 DPPF and L14 1,1′-Ferrocenediyl-bis (dicyclohexylphosphine) in combination with NiCl$_2$ as Ni precursor were tested standard conditions (1.5 eq of B$_2$Pin$_2$, 3 eq of Cs$_2$CO$_3$) using different catalyst loadings. Two solvents: toluene and its higher boiler analogue, p-xylene were chosen for the experiments at two temperatures: 90° C. and 100° C. To prevent the decomposition of the vial caps at high temperatures, 10 mL vials were used so that the caps are not in contact with the heating zone of the stemblock.

Reaction conditions: Ni salt (x mol %, see below); Ligand (1.17 equiv/Ni); compound 1 (0.3 mmol); Cs$_2$CO$_3$ (3 equiv/1); B$_2$Pin$_2$ (1.5 equiv/1); Toluene or p-Xylene (1.5 mL); 20 h. For T=90° C., catalyst loading=5; 10 and 20 mol %. For T=100° C., catalyst loading=2.5; 5 and 10 mol %.

Ligand to metal ratio: Monodentate ligand (L3, P(Oct)$_3$): (2.3 equiv/Ni). Bidentate ligands (L13 DPPF, L14 DCyPF): (1.17 equiv/Ni). The reaction results are shown in the table below.

TABLE 18

Reaction results summary (in area %):

| T | Solvent | Ligand | Cat. load (mol %) | Area % (SM) | Area % (P) | Area % (vinylphenol) |
| --- | --- | --- | --- | --- | --- | --- |
| 90° C. | Toluene | P(Oct)3 | 5 | 57 | 40 | 3 |
| | | P(Oct)3 | 10 | 39 | 58 | 1 |
| | | P(Oct)3 | 20 | 12 | 83 | |
| | p-Xylene | P(Oct)3 | 5 | 66 | 34 | |
| | | P(Oct)3 | 10 | 58 | 41 | |
| | | P(Oct)3 | 20 | 4 | 96 | |
| | Toluene | DPPF | 5 | 51 | 38 | |
| | | DPPF | 10 | 43 | 45 | 1 |
| | | DPPF | 20 | 25 | 55 | 3 |
| | p-Xylene | DPPF | 5 | 61 | 39 | |
| | | DPPF | 10 | 52 | 48 | |
| | | DPPF | 20 | 48 | 52 | |
| | Toluene | DCyPF | 5 | 23 | 71 | 3 |
| | | DCyPF | 10 | 20 | 80 | |
| | | DCyPF | 20 | | >99 | |
| | p-Xylene | DCyPF | 5 | 60 | 40 | |
| | | DCyPF | 10 | 46 | 53 | |
| | | DCyPF | 20 | 34 | 65 | |

TABLE 18-continued

Reaction results summary (in area %):

| T | Solvent | Ligand | Cat. load (mol %) | Area % (SM) | Area % (P) | Area % (vinylphenol) |
|---|---------|--------|-------------------|-------------|------------|----------------------|
| 100° C. | Toluene | P(Oct)3 | 2.5 | 79 | 15 | |
| | | P(Oct)3 | 5 | 50 | 44 | |
| | | P(Oct)3 | 10 | 38 | 55 | |
| | p-Xylene | P(Oct)3 | 2.5 | 99 | 1 | |
| | | P(Oct)3 | 5 | 81 | 19 | |
| | | P(Oct)3 | 10 | 52 | 48 | |
| | Toluene | DPPF | 2.5 | 59 | 38 | |
| | | DPPF | 5 | 44 | 49 | |
| | | DPPF | 10 | 28 | 66 | |
| | p-Xylene | DPPF | 2.5 | 98 | 1 | |
| | | DPPF | 5 | 98 | 1 | |
| | | DPPF | 10 | 98 | 1 | |
| | Toluene | DCyPF | 2.5 | 74 | 26 | |
| | | DCyPF | 5 | 58 | 42 | |
| | | DCyPF | 10 | 44 | 56 | |
| | p-Xylene | DCyPF | 2.5 | 99 | | |
| | | DCyPF | 5 | 89 | 10 | |
| | | DCyPF | 10 | 83 | 16 | |

*SM (Starting material); P (product-compound 2); side product -vinylphneol

At 90° C., a good reproducibility was achieved at 5 mol % ligand loading for all 3 catalysts. NiCl$_2$/L3 (in p-xylene) and NiCl$_2$/L14 (in toluene) catalysts gave almost full conversion at 90° C. at 20 mol %. 55% conversion was obtained when using NiCl$_2$/L13 catalyst at 20 mol %. For L13, the same activity is obtained in both toluene and p-xylene.

Example 15

The heating rate and stirring rate were studied in the catalytic reactions. The borylation reaction using 5 mol % of the NiCl$_2$/L3 catalyst was run at 100° C. in the microwave, where the heating was very fast in comparison to thermal heating. The NiCl$_2$/L3 catalyzed borylation reaction was run at lower temperature (i.e. 80° C.) in toluene and p-xylene using a catalyst loading of 10 and 20 mol %. The idea was to test whether a lower reaction temperature would limit to the catalyst deactivation/decomposition. The NiC$_2$/L3 catalyst was tested on a larger scale (1.25 mmol of Compound 1 instead of 0.3 mmol) in a Schlenk tube. In this set up, a very efficient mixing of the reagents was achieved via a fast magnetic stirring while the increase in the reaction temperature was gradual (ca 30-40 min until reaching 90° C., oil bath). Reaction conditions: Ni salt (5; 10 and 20 mol %); Ligand (1.17 or 2.3 equiv/Ni; 10; 20 or 40 mol %); Compound 1 (0.3 mmol); Cs$_2$CO$_3$ (3 equiv/1); B$_2$Pin$_2$ (1.5 equiv/1); Solvent (1.5 mL); 20 h.

TABLE 19

Reaction results summary (in area %):

| T/ ° C. | Solvent | Set up | Ni (mol %) | Ligand (mol %) | Area % (SM) | Area % (P) |
|---------|---------|--------|------------|----------------|-------------|------------|
| 100 | Toluene | MW | NiCl2 (5%) | P(Oct)3 (10%) | 96 | 1 |
| 80 | Toluene | stemB | NiCl2 (10%) | P(Oct)3 (20%) | 56 | 33 |
| 80 | Toluene | stemB | NiCl2 (20%) | P(Oct)3 (40%) | 58 | 41 |
| 80 | p-xylene | stemB | NiCl2 (10%) | P(Oct)3 (20%) | 70 | 30 |
| 80 | p-xylene | stemB | NiCl2 (20%) | P(Oct)3 (40%) | 53 | 47 |

TABLE 19-continued

Reaction results summary (in area %):

| T/ ° C. | Solvent | Set up | Ni (mol %) | Ligand (mol %) | Area % (SM) | Area % (P) |
|---------|---------|--------|------------|----------------|-------------|------------|
| 90* | Toluene | stemB | NiCl2 (10%) | P(Oct)3 (20%) | 39 | 58 |
| 90* | Toluene | schlenk | NiCl2 (10%) | P(Oct)3 (20%) | 38 | 55 |

*SM (Starting material); P (product-compound 2)

When the borylation reaction was run in the microwave, the NiC$_2$/L3 catalyst exhibited no activity at all suggesting that the catalyst is thermally unstable when subjected to a rapid heating. At 80° C. the product formation was lower than at 90° C. Overall, the decrease in reaction rate was not compensated by an expected higher catalyst stability at lower T. The reactions run in the stemblock and in the Schlenk tube at larger scale at 90° C. exhibited very similar conversions (58 vs 55%).

Example 16

The phosphine to metal ratio and dosing catalyst were studied using several ligands. To study the factors causing catalyst deactivation, two additional experiments were run at 90° C. using p-xylene/toluene as solvent:

The NiCl$_2$/L3 catalyzed borylation reaction was run using different molar amounts of the phosphine ligand (10; 20 and 40 mol % ligand in combination with 10 mol % NiCl2) to investigate whether the catalyst deactivation could stem from the phosphine de-coordination from the catalytically active Ni species. The use of an excess of phosphine ligand can be utilized in Ni promoted cross couplings and C—O cleavages to enhance the catalyst's lifetime as described in Chem. Rev. 2011, 111, 1346, which is incorporated herein by reference.

The NiCl$_2$/L3 catalyst was also dosed in two portions (5+5 mol %) to identify whether the fast deactivation of the catalysts could be due to a fast change of the oxidation state of the catalytically active Ni species and/or a consecutive disproportionation. Such forms of deactivation could be seen a consequence of Ni being able to easily access many oxidation states (i.e. from Ni(0) to Ni(III);) and to its innate tendency to participate in disproportionation/comproportionation reactions (i.e. the disproportionation of NiX2 (dppe) in Inorg. Chem. 1991, 30, 2098, which is incorporated herein by reference).

Reaction conditions: Ni salt (5; 10 and 20 mol %); Ligand (1.17 or 2.3 equiv/Ni; 10; 20 or 40 mol %); Compound 1 (0.3 mmol); Cs2CO3 (3 equiv/1); B2Pin2 (1.5 equiv/1); Solvent (1.5 mL); 20 h.

Reaction conditions (catalyst dosage in two portions): Ni salt (10 mol %); Ligand (2.3 equiv/Ni; 20 mol %); Compound 1 (0.3 mmol); Cs2CO3 (3 equiv/1); B2Pin2 (1.5 equiv/1); Solvent (1.5 mL); 20 h.

The catalyst was prepared in toluene (800 µL) and stirred for 1 h at 90° C. Half of the solution (400 µL) was added to the reaction mixture and after 2 h, the remaining catalyst (400 µL) was added to the reaction. The results are summarized in the table below.

TABLE 20

Summary of study results (in area %):

| Solvent | Set up | Ni (mol %) | Ligand (mol %) | Area % (SM) | Area % (P) |
|---|---|---|---|---|---|
| p-Xylene | stemB | NiCl2 (10%) | P(Oct)3 (10%) | 74 | 26 |
| p-Xylene | stemB | NiCl2 (10%) | P(Oct)3 (20%) | 60 | 40 |
| p-Xylene | stemB | NiCl2 (10%) | P(Oct)3 (40%) | 58 | 42 |
| Toluene | stemB | NiCl2 (10%) | P(Oct)3 (20%) | 39 | 58 |
| Toluene | Schlenk | NiCl2 (10%) | P(Oct)3 (20%) | 38 | 55 |
| Toluene | stemB | NiCl2 (5 + 5%) | P(Oct)3 (10 + 10%) | 33 | 67 |

*SM (Starting material); P (product-compound 2)

The molar amount of the phosphine was found to play a pivotal role in the catalytic borylation. A two-fold reduction in the molar amount of phosphine resulted in a lower conversion (26 vs 40%) whereas a two-fold increase brought no significant improvement in the reaction outcome (42 vs 40%). These experiments suggest that a Ni/P(Oct)$_3$ ratio of 1/2 achieved great results and that phosphine de-coordination might not be the main cause behind catalyst deactivation.

A moderate increase in the reaction conversion (67 vs 58%) was found when the catalyst was dosed in two portions, suggesting that the lifetime of the NiCl$_2$/L3 catalyst could be improved via a dosing protocol. By analogy to the behavior exhibited by the NiX$_2$(dppe) complex, it might be possible that the disproportionation reaction indicated below would take place under the reaction condition, causing the deactivation of the pre-catalyst. Diluting the pre-catalyst might help to displace the equilibrium to the left.

2NiCl$_2$[P(Oct)$_3$]$_2$≈Ni[P(Oct)$_3$]$_4$Cl$_2$+NiCl$_2$

The effect of the solvent and the base was next investigated by testing the NiCl$_2$/L3 catalyzed borylation of 4 at 90° C. using a catalyst loading of 10 mol %. The following bases were chosen for the study: K$_2$CO$_3$; K$_2$CO$_3$/Cs$_2$CO$_3$ 9/1; Cs$_2$CO$_3$ and Li$_2$CO$_3$ together with 5 solvents: the a polar solvents toluene and p-xylene; the ethereal solvents: THF and dibutyl ether and the very polar dimethyl acetamide (DMA). The reaction conditions included Ni salt (10 mol %); Ligand (2.3 equiv/Ni; 20 mol %); Compound 1 (0.3 mmol); Cs$_2$CO$_3$ (3 equiv/Compound 1); B$_2$Pin$_2$ (1.5 equiv/Compound 1); Solvent (1.5 mL); 20 h. The results are shown in the table below.

TABLE 21

Summary of reaction results (in area %):

| Base | Solvent/T | Area % (SM) | Area % (P) |
|---|---|---|---|
| K2CO3 | Toluene | 79 | 16 |
| K$_2$CO$_3$/Cs$_2$CO$_3$ 9/1 | | 32 | 66 |
| Cs$_2$CO$_3$ | | 61 | 39 |
| Li$_2$CO$_3$ | | 99 | 1 |
| K$_2$CO$_3$ | Xylene | 75 | 22 |
| K$_2$CO$_3$/Cs$_2$CO$_3$ 9/1 | | 50 | 49 |
| Cs$_2$CO$_3$ | | 49 | 51 |
| Li$_2$CO$_3$ | | 99 | 1 |
| K$_2$CO$_3$ | THF | 40 | 57 |
| K$_2$CO$_3$/Cs$_2$CO$_3$ 9/1 | | 24 | 74 |
| Cs$_2$CO$_3$ | | 30 | 69 |
| Li$_2$CO$_3$ | | 98 | 2 |
| K$_2$CO$_3$ | DMA | 68 | 28 |
| K$_2$CO$_3$/Cs$_2$CO$_3$ 9/1 | | 67 | 29 |
| Cs$_2$CO$_3$ | | 59 | 37 |
| Li$_2$CO$_3$ | | 90 | 2 |
| K$_2$CO$_3$ | DibutylO | 77 | 23 |
| K$_2$CO$_3$/Cs$_2$CO$_3$ 9/1 | | 69 | 29 |
| Cs$_2$CO$_3$ | | 60 | 39 |
| Li$_2$CO$_3$ | | 99 | 1 |

*SM (Starting material); P (product-compound 2)

The combination of THF as a solvent with K$_2$CO$_3$/Cs$_2$CO$_3$ 9/1 as abase gave the highest conversion (74 area %). The mixture of K$_2$C$_3$/Cs$_2$CO$_3$ 9/1 gave also highest conversions in toluene whereas Cs$_2$CO$_3$ was the most efficient base in p-xylene, DMA and dibutyl ether. The NiCl$_2$/L3 catalyst showed higher efficiency in a polar solvents (toluene and p-xylene) and THF whereas significantly lower conversions were obtained in DMA and dibutyl ether.

Example 17

The NiCl$_2$/L3 catalyzed borylation of Compound 1 was investigated at a larger scale under the reaction conditions that afforded the desired product 2 in higher conversions. Thus, the borylation of 1 (0.6 mmol) was first tested at 90° C. in THF as a solvent and K$_2$C$_3$/Cs$_2$CO$_3$ 9/1 as a base. The first reaction was run in the stemblock in a 10 mL vial and using a dosage protocol by which the catalyst solution (10 mol %) was added to the reaction mixture in five portions (of 2 mol %) in 1 hour intervals. A second borylation reaction of 1 (1.2 mmol) was run in a Schlenk tube under the same conditions (solvent, base, temperature) except for the catalyst (20 mol %) being added in one single portion at the beginning of the reaction.

The reaction conditions (stemblock) included Ni salt (10 mol %); Ligand (2.3 equiv/Ni; 20 mol %); Compound 1 (0.6 mmol); K$_2$CO$_3$/Cs$_2$CO$_3$ 9/1 (3 equiv/Compound 1); B$_2$Pin$_2$ (1.5 equiv/Compound 1); THF (3.0 mL); 20 h. The catalyst was prepared in toluene (1000 μL) and stirred for 1 h at 90° C. The catalyst solution was added to the reaction mixture in five portions (200 μL each) in 1 h intervals and once the addition was completed, the reaction was stirred overnight at 90° C.

The reaction conditions (Schlenk tube) included Ni salt (20 mol %); Ligand (2.3 equiv/Ni; 40 mol %); Compound 1 (1.2 mmol); K$_2$CO$_3$/Cs$_2$CO$_3$ 9/1 (3 equiv/Compound 1); B$_2$Pin$_2$ (1.5 equiv/Compound 1); THF (6.0 mL); 20 h. The results are shown in the table below.

TABLE 22

Summary of reaction results (in area %):

| Ligand Load | Time/h | Area % (SM) | Area % (P) | Area % (vinylphenol) |
|---|---|---|---|---|
| 10% dosed | 1 - 1st addition | 59 | 39 | |
| | 2 - 2d addition | 35 | 64 | 1 |
| | 3 - 3rd addition | 26 | 73 | 1 |
| | 4 - 4th addition | 16 | 82 | 2 |
| | 5 - 5th addition | 16 | 82 | 2 |
| | 18 | 12 | 87 | 1 |
| 20% schlenk | 1 | 29 | 63 | 7 |
| | 2 | 27 | 66 | 6 |
| | 3 | 26 | 66 | 7 |
| | 18 | 25 | 67 | 7 |

*SM (Starting material); P (product-compound 2); side product -vinylphneol

By dosing the catalyst solution, a gradual increase in the conversion of 1 was observed which led to a final 87% area of the desired borinine 2. As the reaction was run in a sealed vial and the catalyst added by syringe through the septum, no solvent losses took place. The $NiCl_2/P(Oct)_3$ and $K_2CO_3/Cs_2CO_3$ 9/1 at 10 mol % ligand load produced high yield.

Example 18

The study involved the synthesis of compound 3 via the enantioselective cyclopropanation of 2 using diazomethane as shown in Scheme 6.

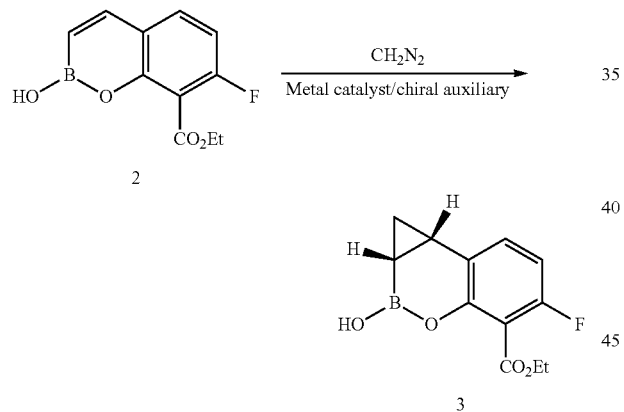

Scheme 6: Enantioselective cyclopropanation towards 3

First, an analytical method was developed and implemented—allowing the separation of both the starting material and the two enantiomers of the product using a chiral HPLC.

Reacting 2 with diazomethane in presence of $Pd(OAc)_2$ resulted a yield of around 30%. Compound 2 was stable in presence of $CH_2N_2$ but can react with acetic acid (used as a quenching reagent for $CH_2N_2$). The non-enantioselective cyclopropanation using $Pd(OAc)_2$ as catalyst showed to be quantitative when using 8 eq of $CH_2N_2$, hence the low yield was most likely due to losses during the isolation.

18 chiral auxiliaries were studied to form an adduct with compound 2 via the B—OH moiety. The chiral auxiliaries compound were selected from 5 different classes of chiral compounds: mono-alcohols, diols, amino-alcohols, diamines, hydroxy acids/esters. After preformation of the adduct at R.T. in THF, they were exposed to $CH_2N_2$ in the presence of a catalytic amount of $Pd(OAc)_2$ at −15° C. With 2 of the chiral auxiliaries (a prolinol derivative and ephedrine), the desired product was obtained with a significant e.e.: 55% and 44% respectively. 7 amino-alcohols compounds were tested. One compound pseudoephedrine gave a high selectivity (78% in favor of the desired enantiomer). In general, all ephedrine derivatives were active and enantioselective. It was also shown that performing the cyclopropanation at −40° C. instead of −15° C. leads to an increase of enantiomeric excess, albeit at the expense of the conversion. Procedure for the enantioselective cyclopropanation of 2 with pseudo-ephedrine is shown in Scheme 7.

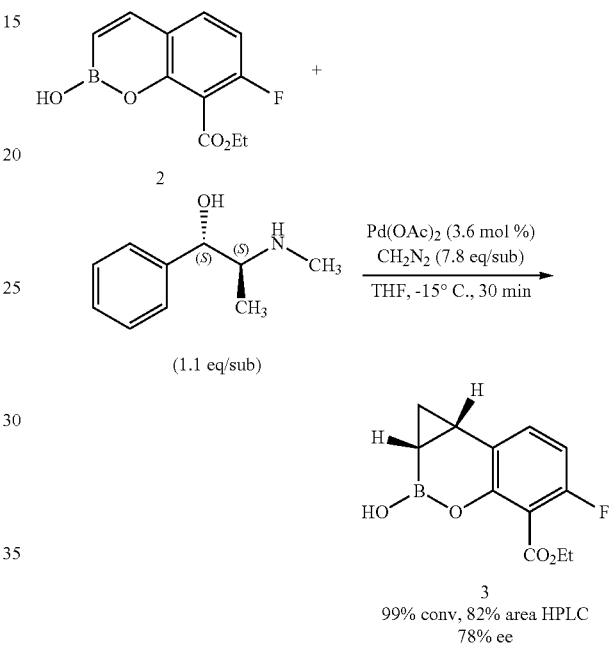

Scheme 7

A stock solution of the oxaborin 2 in dry THF (30 mg/mL, 0.127 mmol) was prepared. Pseudoephedrine was weighed (1.1 eq/1), placed into a 20 mL glass vial, and dissolved into 4 mL of dry THF. mL of the substrate stock solution was added to the solution of chiral auxiliary and the mixture was stirred for 1 h at room temperature. A stock solution of $Pd(OAc)_2$ was prepared (1 mg/mL, 0.004 mmol). A fresh solution of diazomethane in $Et_2O$ was prepared from Diazald®. Its concentration (~0.33M) was determined by GC after reaction with benzoic acid.

The solution of substrate/pseudoephedrine was cooled to −15° C. in an salt/ice/water bath. 1 mL catalyst stock solution (Sub/Cat=28) and 3 mL diazomethane solution ($CH_2N_2$/Sub=7.8) were added to the reactor vial. The reaction mixture was stirred during 30 min at −15° C. before increasing the temperature slowly to 22° C.

HPLC samples: To cleave off the chiral auxiliary, each HPLC sample was treated with an excess of $H_2O$ for at least 10 min prior to the injection: 100 µL reaction mixture; 900 µL heptane/EtOH (100/1); 20 L $H_2O$. Using a combination of a precolumn with a chiral HPLC column, it was possible to develop a method to analyze both the substrate and the enantiomeric product. The reaction sample is dissolved in heptane/EtOH (99/1) to ~1 mg/ml.

Example 19

The diazomethane kit from Aldrich (no grounded glass connections) was used to prepare the diazomethane solution in ether from Diazald® as shown in Scheme 8. A Diazald® (6.0 g, 28.0 mmol) solution in diethyl ether (60 ml) was dosed during 1.5 hours to a warm (65° C.) solution of KOH/water (15 mL, 5.4M, 81 mmol) and carbitol (17 mL, diethylene glycol monomethyl ether). The diazomethane/ether solution was distilled at 65° C. and collected at −30° C. to −40° C. Extra 10 mL ether was used to clean the set-up.

Scheme 8: Preparation of diazomethane from Diazald®

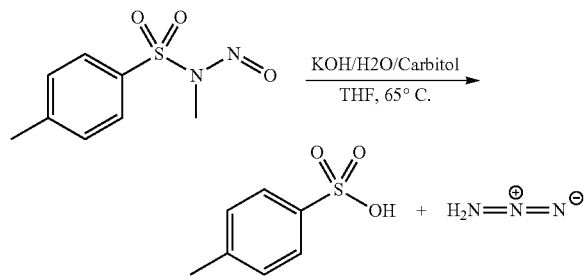

The concentration of diazomethane in ether was determined via GC analysis of the amount of methyl benzoate formed upon esterification of benzoic acid with $CH_2N_2$. 0.5 mL of the solution of diazomethane in ether (~0.33M) was dissolved in a solution of 0.5 mL benzoic acid solution (0.8M) and 10 ml acetonitrile. The resulting methylbenzoate was quantitatively analyzed by GC.

Example 20

A non-enantioselective catalyst was used to determine the amount of $CH_2N_2$ needed for full conversion and an isolated yield. 50 mg of benzoxaborin (2) (0.212 mmol) was dissolved in 2 mL dry THF. 5 mg Pd(OAc)$_2$ (0.022 mmol, S/C=10) was added and the reaction mixture was cooled down to T=−16° C. or T=−40° C. 3 tests were performed: Test A: To a solution at −40° C., 15 eq of $CH_2N_2$ (solution in diethylether (0.335M)) was added in one portion and the vial was removed from the cool bath. Test B: To a solution at −16° C., 12 eq of $CH_2N_2$ was added in 4 portions. Test C: To a solution at −40° C., 8 eq of $CH_2N_2$ was added in 4 portions.

30 min after each addition, the reaction mixture was analyzed by HPLC. AcOH was used as a quenching agent for test B since it would not lead to some decomposition of 2. For Test A: After addition of $CH_2N_2$, the vial was taken out of the cool bath. Upon warming up to room temperature, a significant amount of $N_2$ was produced. Full conversion by HPLC. For Test B and C, the conversion rate increased with the amount of $CH_2N_2$ before it reached 100% conversion. As already mentioned, AcOH was used as a quenching agent for test B except for the last sampling at 12.6 eq of $CH_2N_2$.

Example 21

Studies were performed with Pd(OAc)$_2$ to determine the amount of $CH_2N_2$ leading to full conversion and the isolated yield.

104 mg of benzoxaborin (1) (0.442 mmol) was dissolved in 1 mL dry THF. 5 mg Pd(OAc)$_2$ (0.022 mmol, S/C=20) in 1 mL THF was added and the reaction mixture is cooled down to T=−16° C. 7.6 eq of $CH_2N_2$ (ether solution, 0.28M, 12 mL) was added in one portion. Evolution of $N_2$ and formation of solids (PE) was observed. After one night during which T increased to room T, the reaction mixture was analyzed by HPLC showing full conversion and an assay yield of 86%.

To isolate the product, the reaction mixture was filtered over a decalite filter to remove the solids (PE and Pd black). The THF/ether solution was concentrated in vacuo (40° C., 40 mbar), resulting in 132 mg oil residue. 1H-NMR was consistent with the desired product and some THF residue (~13%). For the further isolation of the product, prep. column chromatography was used with heptane/EtOH (4/1) as eluent. In preparation for the column chromatography, the oily residue was further concentrated on the rotovap (40° C., 40 mbar) to remove the residual THF. This resulted in 122 mg sticky oil with solid tar, that did not completely dissolved anymore in heptane, ethanol or ether.

Analysis of the reaction mixture after different reaction times with $CH_2N_2$: Same procedure as above except: 4 eq of $CH_2N_2$ instead of 7.6, 4 mL of THF instead of 2 mL. The reaction mixture was sampled after 5 min, 10 min, 20 min, 30 min, 240 min. After 5 min, HPLC analysis showed 85% conv., 80% assay yield. No changes observed afterwards indicating that the reaction occurred within the first 5 minutes.

Example 22

Chiral auxiliaries compounds shown in the table below were tested. A stock solution of the oxaborin 2 in dry THF (30 mg/mL, 0.127 mmol) was prepared. The chiral auxiliary was weighed (1.1 eq/1) and placed into a 20 mL glass vial. 4 mL of dry THF was added to the chiral auxiliary. 1 mL of the substrate stock solution was added to the chiral auxiliary and the mixture is stirred for 4 h at room temperature.

A stock solution of Pd(OAc)$_2$ was prepared (1 mg/mL, 0.004 mmol). A fresh solution of diazomethane in Et$_2$O was prepared from Diazald®. Its concentration (~0.33M) is determined by GC after reaction with benzoic acid. The mixtures of substrate/chiral auxiliaries were cooled to −15° C. in an salt/ice/water bath. 1 mL catalyst stock solution (Sub/Cat=28) and 3 mL diazomethane solution (CH$_2$N$_2$/Substrate=7.8) were added to the reactor vial. The reaction mixture was stirred during 30 min at −15° C. before increasing the temperature slowly to 22° C.

TABLE 23

| | Chiral auxiliary compounds | | | |
|---|---|---|---|---|
| | Mono alcohols | | | |
| A1 | (R)-(+)-1-Phenylethanol | 1517-69-7 | 122.16 | |

TABLE 23-continued

| | Chiral auxiliary compounds | | | |
|---|---|---|---|---|
| A2 | L-Menthol | 2216-51-5 | 156.27 | |
| A3 | (−)-Borneol | 464-45-9 | 154.25 | |

| | Diols | | | |
|---|---|---|---|---|
| A4 | (4S,5S)-2,2-Dimethyl-α,α,α',α'-tetraphenyldioxolane-4,5-dimethanol | 93379-49-8 | 466.57 | |
| A5 | (R)-(+)-1,1'-Bi(2-naphthol) | 18531-94-7 | 286.32 | |

| | Amino alcohols | | | |
|---|---|---|---|---|
| A6 | (R)-(−)-2-Phenylglycinol | 56613-80-0 | 137.18 | |
| A7 | (R)-(−)-2-Amino-1-phenylethanol | 2549-14-6 | 137.18 | |
| A8 | (S,S)-(−)-2-Amino-1,2-diphenylethanol | 23190-17-2 | 213.28 | |
| A9 | (R)-(−)-2-Pyrrolidinemethanol | 68832-13-3 | 101.15 | |

TABLE 23-continued

| | Chiral auxiliary compounds | | | |
|---|---|---|---|---|
| A10 | (R)-(+)-α,α-Diphenyl-2-pyrrolidinemethanol | 22348-32-9 | 253.34 | |
| A11 | (1R,2S)-(−)-Ephedrine | 299-42-3 | 165.23 | |
| | Diamines | | | |
| A12 | (1R,2R)-(+)-1,2-Diphenylethylenediamine | 35132-20-8 | 212.29 | |
| A13 | (1R,2R)-(−)-N-p-Tosyl-1,2-Diphenylethylenediamine | 144222-34-4 | 366.48 | |
| | Hydroxy acids and ester | | | |
| A14 | L-(+)-Lactic acid | 79-33-4 | 90.08 | |
| A15 | (R)-(−)-Mandelic acid | 611-71-2 | 152.15 | |
| A16 | (−)-Methyl L-lactate | 27971-49-4 | 104.1 | |
| A17 | L-(+)-Tartaric acid | 87-69-4 | 150.09 | |
| A18 | L-(+)-Tartaric acid dimethyl ester | 608-68-4 | 178.14 | |

A stock solution of the oxaborin 2 in dry THF (3 mg/mL, 0.27 mmol) was prepared. The chiral auxiliary was weighed (1.1 eq/1) and placed into 2 mL glass vial. 4 mL of dry THF was added to the chiral auxiliary. 1 mL of the substrate stock solution was added to the chiral auxiliary and the mixture was stirred for 4 h at room temperature. For the acids (A14, A15 and A17), 1 eq or 2 eq of $Et_3N$ were added. A stock solution of $Pd(OAc)_2$ was prepared (1 mg/mL, 0.04 mmol). A fresh solution of diazomethane in $Et_2O$ was prepared from Diazald®. Its concentration (~0.33M) was determined by GC after reaction with benzoic acid.

The mixtures of substrate/chiral auxiliaries were cooled to −15° C. in an salt/ice/water bath. 1 mL catalyst stock solution (Sub/Cat=28) and 3 mL diazomethane solution ($CH_2N_2$/Substrate=7.8) were added to the reactor vial. The reaction mixture was stirred during 30 min at −15° C. before increasing the temperature slowly to 22° C. HPLC samples: To cleave off the chiral auxiliary, each HPLC sample was treated with an excess of $H_2O$ prior to the injection: 100 μL reaction mixture; 900 μL heptane/EtOH (100/1); 208 μL $H_2O$ Both conversion and yield of products were determined via the area of starting material left or product obtained relative to the expected areas, and the results are shown in the table below.

TABLE 24

Reaction results summary

| Chiral Auxiliary | Conv. % | Yield % P1 + P2 | e.e % |
|---|---|---|---|
| A1 | 99 | 85 | −2 |
| A2 | 100 | 88 | −2 |
| A3 | 99 | 87 | −2 |
| A4 | 99 | 131 | −29 |
| A5 | 99 | 81 | −2 |
| A6 | 86 | 72 | 0 |
| A7 | 97 | 36 | 1 |
| A8 | 2 | 1 | −2 |
| A9 | 100 | 86 | −4 |
| A10 | 50 | 47 | −55 |
| A11 | 100 | 65 | 44 |
|  | 100 | 86 | 38 (HCL treatment) |
| A12 | 0 | 0 |  |
| A13 | 0 | 0 |  |

TABLE 24-continued

Reaction results summary

| Chiral Auxiliary | Conv. % | Yield % P1 + P2 | e.e % |
|---|---|---|---|
| A14 | 96 | 77 | −4 |
| A15 | 56 | 33 | 5 |
| A16 | 98 | 89 | −5 |
| A17 | 17 | 18 | 1 |
| A18 | 100 | 8 | −8 |
|  | 100 | 91 | 3 (HCL treatment) |

Good conversions were obtained with chiral auxiliaries. For 3 chiral auxiliaries (A4, A10, A11), a significant enantiomeric excess was obtained. In the case of A10 and A11, the chromatograms did not show co-elution. A true enantioselective cyclopropanation was achieved. Both auxiliaries were also injected on the column and did not co-elute with the products.

A small sample of the reaction mixture obtained with A11 was further hydrolyzed with 0.1N HCl: To 1 ml of reaction mixture, concentrated on rotavap, add 1 ml 0.1N HCl, extract with 1 ml EtOAc. The organic phase was dried with $Na_2SO_4$. 0.1 mL of this solution was diluted into 0.9 mL eluent and injected on the HPLC (ee=38%).

The reaction mixture obtained with A11 was further worked up according to the following procedure: The reaction mixture was concentrated on the rotavap (50 mbar). 5 mL of EtOAc was added followed by 5 mL of 0.1M HCl leading to a biphasic mixture containing some solids (polyethylene). The layers were separated and the water phase washed with 2 mL EtOAc. The organic phase was dried with Na2SO4, filtered and concentrated on the rotovap (40° C., 20 mbar). 23.5 mg of an oil is obtained—equivalent to 27.6 mg if we correct from the sampling (expected max.=31.7 mg)—estimate yield: 87%.

Example 22

The addition of an enantiopure chiral auxiliary to the oxaborin led to the formation of at least 2 diastereomers (boron center=becoming chiral upon dative bond with N lone pair). The situation was even more complicated with N-monosubstituted amino alcohols (such as ephedrine) due to the formation of N-epimers—i.e. 4 diastereomers (Scheme 9).

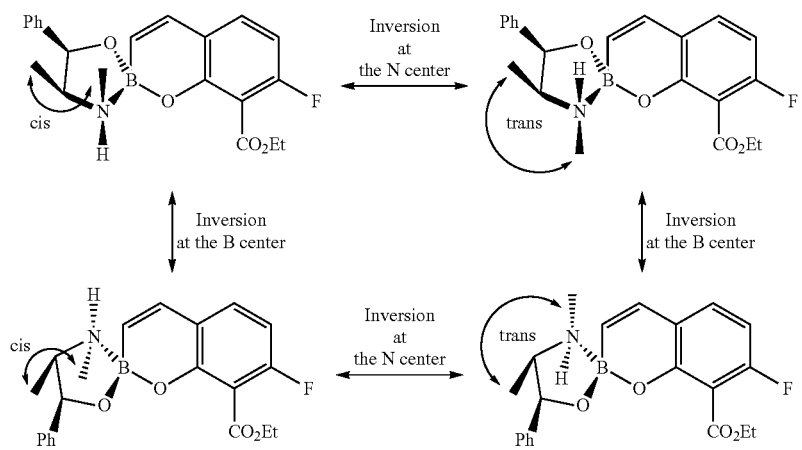

Scheme 9

N,N-dimethyl amino-alcohols led to a less stable adduct, while there were not so much difference between the non-substituted and monomethylated adduct. Trans configuration for the substituent (pseudo-ephedrine) led to stronger N→B bond. A study of the structure of ephedrine/pseudo-ephedrine-Ph$_2$BH adducts is described in J. Organomet. Chem. 1997, 544, 175-188, which is incorporated herein by reference.

Example 23

A list of chiral auxiliary for enantioselective cyclopropanation were tested, including A6-A11 in table 24 and A19-A25 with the structure of the chiral auxiliary compounds below. Since the enantiomeric excess is calculated according to the following formula: (area(1st peak)-area(2d peak))/(area(1st peak)+area(2d peak))%, a negative ee means that the desired enantiomer is formed predominantly. It was the case with A10, the prolinol derivative while a11, ephedrine gave the other enantiomer.

A10: (R)-(+)-α,α-Diphenyl-2-pyrrolidinemethanol 50% conv, -55% ee

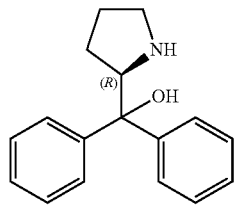

(right enantiomer)Ephedrine derivatives
A11: ((1R,2S)-(-)-Ephedrine (100% conv, 38% ee(wrong enantiomer)

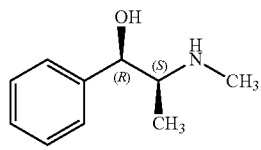

Chiral amino-alcohol Ephedrine derivatives: 3 ephedrines for structure-activity relationship are also shown below.
A19: ((1S,2S)-(+)-Pseudoephedrine (trans-configuration)

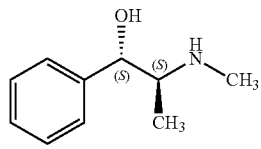

A20: (1R,2S)-(-)-Norephedrine (cis-config.; primary amine)

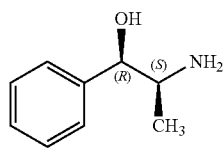

A:21: (1R,2S)-(-)-N-Methylephedrine (cis-config; tertiary amine)

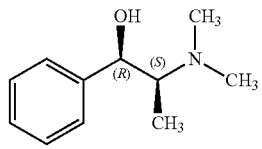

Amino-acid derived: 1 less sterically hindered prolinol
A22: (S)-2-(Pyrrolidin-2-yl)propan-2-ol

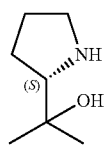

Amino-Alcohol:
A23: N-Methyl-D-glucamine

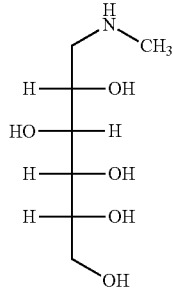

A24: (1R,2R)-(-)-2-Amino-1-(4-nitrophenyl)-1,3-propanediol

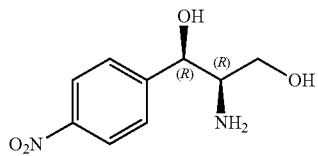

A25: Quinine

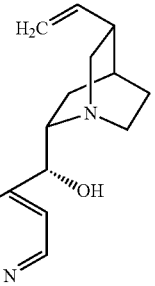

A26: Hydroquinine

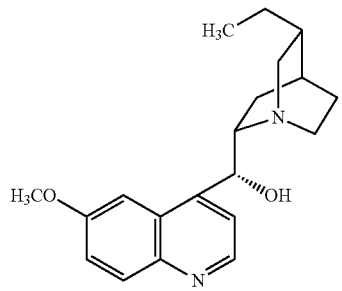 [SMILES: CCC1CN2CCC1CC2[C@H](O)c1ccnc2ccc(OC)cc12]

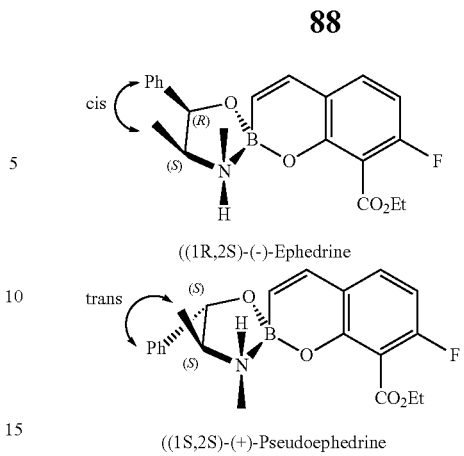

((1R,2S)-(−)-Ephedrine)

((1S,2S)-(+)-Pseudoephedrine)

A stock solution of the oxaborin 2 in dry THF (30 mg/mL, 0.127 mmol) is prepared. The chiral auxiliary was weighed (1.1 eq/2) and placed into a 20 mL glass vial. 4 mL of dry THF is added to the chiral auxiliary. 1 mL of the substrate stock solution is added to the chiral auxiliary and the mixture is stirred for 1 h at room temperature. A stock solution of $Pd(OAc)_2$ was prepared (1 mg/mL, 0.004 mmol). A fresh solution of diazomethane in $Et_2O$ was prepared from Diazald®. Its concentration (~0.33M) was determined by GC after reaction with benzoic acid. The mixtures of substrate/chiral auxiliaries were cooled to −15° C. in an salt/ice/water bath. 1 mL catalyst stock solution (Sub/Cat=28) and 3 mL diazomethane solution ($CH_2N_2$/Sub=7.8) were added to the reactor vial. The reaction mixture was stirred during 30 min at −15° C. before increasing the temperature slowly to 22° C. HPLC samples: To cleave off the chiral auxiliary, each HPLC sample was treated with an excess of $H_2O$ prior to the injection: 100 µL reaction mixture; 900 µL heptane/EtOH (100/1); 20 µL $H_2O$ Both conversion and yield of products are determined via the area of starting material left or product obtained relative to the expected areas.

TABLE 25

Summary of reaction results.

| Entry # | Chiral Auxiliary | Conv (%) | Yield (%) | e.e (%) |
|---|---|---|---|---|
| 1 | A11 | 99 | 82 | 30 |
| 2 | A11 | 88 | 78 | 43 |
| 3 | A19 | 99 | 82 | −78 (right isomer) |
| 4 | A20 | 73 | 63 | −15 (right isomer) |
| 5 | A21 | 97 | 86 | −55 (right isomer) |
| 6 | A22 | 41 | 37 | −4 |
| 7 | A23 | 92 | 11 | 8 |
| 8 | A24 | 25 | 21 | 28 |
| 9 | A25 | 2 | — | — |

Entries #1 and 2: A11 (ephedrine) was tested again and gave a slightly lower ee (30% vs 38%) compared to the previous time. At lower temperature, the reaction was not complete but a slightly higher enantiomeric excess was obtained. Entry #3, 4, 5: All ephedrines analogs gave some enantiomerically enriched product with the highest enantiomeric excess (78% at full conversion) obtained with pseudoephedrine in favor of the desired enantiomer. Note that pseudoephedrine is the only ephedrine derivative where the Me and Ph substituents are in a trans-configuration.

Norephedrine (primary amine) gave some enantiomeric excess unlike the related A7 that gave the racemic product. This showed the importance of having a chiral center at the amine group.

N-Me-(−)-ephedrine (tertiary amine) was also an efficient chiral auxiliary giving the right enantiomer with a slightly lower ee. The simple addition of a methyl group to (−)-ephedrine triggered the formation of the opposite enantiomer.

What is claimed is:

1. A method of making a compound of formula (I) or pharmaceutically acceptable salt thereof,

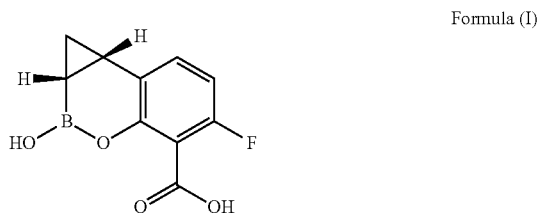 [SMILES: O=C(O)c1c(F)ccc2c1OB(O)[C@@H]1C[C@H]21]

Formula (I)

comprising the steps of:
reacting a compound of formula (A-I)

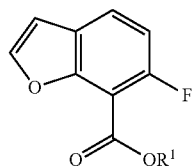

with a borylating agent to form an organoboron intermediate;
converting the organoboron intermediate to a compound of Formula (A-III)

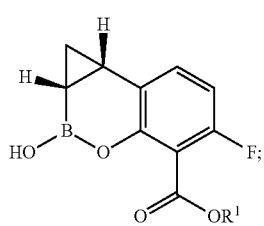

and
 hydrolyzing the compound of Formula (A-III) to form the compound of Formula (I),
 wherein:
 $R^1$ is a carboxylic acid protecting group.

2. The method of claim 1, wherein the organoboron intermediate has a structure of formula (A-II)

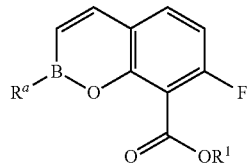

wherein
 $R^a$ is OH or optionally substituted —O—$C_{1-6}$ alkyl.

3. The method of claim 1, wherein the organoboron intermediate is combined with one or more chiral auxiliaries to form a chiral complex having a structure of formula (A-II')

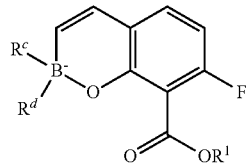

wherein $R^c$ and $R^d$ with any intervening atoms form an optionally substituted 4-7 membered heterocyclyl ring.

4. The method of claim 1, wherein the borylating agent is $(R^2O)_2B$—$B(OR^2)_2$, wherein each $R^2$ is independently H, optionally substituted $C_{1-6}$alkyl, or two $R^2$ together are an optionally substituted $C_{2-4}$ alkylene chain and form an optionally substituted 5-7 membered heterocyclyl ring with the intervening atoms.

5. The method of claim 1, wherein the borylating agent is selected from the group consisting of $(HO)_2B$—$B(OH)_2$, $B_2(Pin)_2$, $B_2(Cat)_2$, and $B_2neop_2$.

6. The method of claim 1, wherein the borylating agent is $B_2(Pin)_2$.

7. The method of claim 1, wherein the reaction of the compound of formula (A-I) and the borylating agent is performed in the presence of a first catalyst.

8. The method of claim 7, wherein the first catalyst comprises one or more Ni catalyst precursors and one or more ligands.

9. The method of claim 8, wherein the Ni catalyst precursor is selected from the group consisting of $NiCl_2$, $Ni(Acac)_2$, $Ni(COD)_2$, $NiCl_2(PPh_3)_2$, $NiCl_2(PCy_2Ph)_2$, $NiCl_2(PPh_2CH_2CH_2PPh_2)$, $NiCl_2(1,3$-Bis(diphenylphosphino)propane), and $NiCl_2(1,3$-Bis(diphenylphosphino)ethane).

10. The method of claim 8, wherein the Ni catalyst precursor is $NiCl_2$ or $Ni(Acac)_2$.

11. The method of claim 8, wherein the ligand is monodentate or bidentate.

12. The method of claim 8, wherein the ligand is selected from the group consisting of NHC ligand, phosphine, phosphite, phosphoramidite, amine, alcohol, aminoalcohol, and a combination thereof.

13. The method of claim 8, wherein the ligand or catalyst is selected from the group consisting of Bis(di-cyclopentylphosphinium)ethyl tetrafluoroborate, 4,5-Bis(di-tert-butylphosphino)-9,9-dimethylxanthene, 2,2'-bis(dicyclohexylphosphanyl)-1,1'-biphenyl, 1,2-bis((di-tert-butylphosphaneyl)methyl)benzene, 1,3-Bis(1-adamanthyl)imidazolium, 1,3-Di-tert-butylimidazolium, 1,3-Bis(2,6-diisopropyl-phenyl)-4,5-dihydroimidazol-2-ylidene, 1,3-bis(2,6-diisopropylphenyl)-1H-imidazol-3-ium-2-ide, $P(Octyl)_3$, Dppf, DiPrf, dcype, JosiPhos 9-1, (S,S,R,R)-TangPhos,(S,S,R,R)-DuanPhos, DavePhos, $P(tBu)_3$, XantPhos, (tBu)XantPhos, (R)-SegPhos, (R)-DM-SegPhos, (R)-MeOBIPHEP, (R,S)-BinaPhos, Binaphane, Phosphoramidite, (S)-SegphosRu(Oac)$_2$, trans-PdCl$_2$(Pcy$_3$)$_2$, [Rh(S,S)EtDuPhos(COD)]Otf, (S)-XylylPhanePhos, (R)-C3-TunePhos, (R)-DTBM-Garphos, (R)-DMM-Garphos, (R,R,R)-Xyl-SKP, Thio-XantPhos, TaniaPhos, SPANPhos, tris(4-methoxyphenyl)phosphine, Tris(2,6-dimethoxyphenyl) phosphine, Trioctylphosphine, Bis(dicyclohexylphosphino) methane), DCYPE, 1,3-Bis(dicyclohexyl phosphino)propane, 1,2-Bis(diphenylphosphino)ethane, (R,R)-Dipamp, Bis(dicyclohexyl phosphinophenyl) ether, DPEPhos, Bis(2-diphenylphosphinoethyl) Phenylphosphine, 1,1,1-Tris(diphenylphosphinomethyl)ethane, DPPF, 1,1'-Ferrocenediyl-bis(dicyclohexylphosphine), DTBPF, DiPrF, 1-Diphenylphosphino-1'-(di-butylphosphino)ferrocene, HiersoPhos, iPr(NHC), SIMe s, IMes, and (1,3-bis[bis(o-methoxyphenyl)phosphino]propane.

14. The method of claim 7, wherein the ligand is $P(Octyl)_3$, diPrf, or dcype.

15. The method of claim 1, wherein the reaction of the compound of formula (A-I) and the borylating agent is performed in the presence of a base system.

16. The method of claim 15, wherein the base system comprises one or more inorganic bases.

17. The method of claim 15, wherein the base system comprises $K_2CO_3$, $Cs_2CO_3$, $Li_2CO_3$, or any combination thereof.

18. The method of claim 15, wherein the base system comprises a mixture of $K_2CO_3$ and $Cs_2CO_3$, wherein the molar ratio of $K_2CO_3$ and $Cs_2CO_3$ is in the range of about 5:1 to 15:1.

19. The method of claim 1, wherein the reaction of the compound of formula (A-I) and the borylating agent is performed in an organic solvent.

20. The method of claim 19, wherein the organic solvent is toluene, xylene, or THF.

21. The method of claim 1, wherein the reaction of the compound of formula (A-I) and the borylating agent is performed at a temperature in the range of about 70° C. to 100° C.

22. The method of claim 1, wherein the reaction of the compound of formula (A-I) and the borylating agent is performed at a temperature of about 90° C.

23. The method of claim 1, wherein the converting of the organoboron intermediate comprises reacting the organoboron intermediate with a cyclopropylating agent.

24. The method of claim 1, wherein the converting of the organoboron intermediate comprises combining the organoboron intermediate and one or more chiral auxiliaries to form a chiral complex and reacting the chiral complex with a cyclopropylating agent.

25. The method of claim 23, wherein the cyclopropylating agent comprises a carbenoid or diazomethane.

26. The method of claim 23, wherein the cyclopropylating agent comprises diazomethane.

27. The method of claim 24, wherein the reaction with the cyclopropylating agent is performed in the presence of a second catalyst.

28. The method of claim 27, wherein the second catalyst comprises a metal catalyst.

29. The method of claim 24, wherein the metal catalyst is selected from Pd catalyst, Cu catalyst, Zn catalyst, Fe catalyst, Mn catalyst, or Rh catalyst.

30. The method of claim 27, wherein the second catalyst is a Pd catalyst.

31. The method of claim 28, wherein the Pd catalyst is Pd(OAc)$_2$.

32. The method of claim 24, wherein the chiral auxiliary is selected from the group consisting of mono alcohol, diol, amino alcohol, diamine, and hydroxyl acid and ester.

33. The method of claim 24, wherein the chiral auxiliary is selected from the group consisting of (R)-(+)-1-phenylethanol, L-menthol, (−)-borneol, (4S,5S)-2,2-dimethyl-α,α,α',α'-tetraphenyldioxolane-4,5-dimethanol, (R)-(+)-1,1'-bis(2-naphthol), (R)-(−)-2-phenylglycinol, (R)-(−)-2-amino-1-phenylethanol, (S,S)-(−)-2-amino-1,2-diphenylethanol, (R)-(−)-2-pyrrolidinemethanol, (R)-(+)-α,α,-diphenyl-2-pyrrolidinemethanol, ((1R,2S)-(−)-ephedrine, (1R,2R)-(+)-1,2-diphenylethylenediamine, (1R,2R)-(−)-N-p-tosyl-1,2,-diphenylethylenediamine, L-(+)-lactic acid, (R)-(−)-mandelic acid, (−) -methyl L-lactate, L-(+) tartaric acid, L-(+)-tartaric acid dimethyl ester, ((1S,2S)-(+)-pseudoephedrine, (1R,2S)-(−)-norephedrine, (1R,2S)-(−)-N-methylephedrine, (S)-2-(pyrrolidin-2-yl)propan-2-ol, N-methyl-D-glucamine, (1R,2R)-(−)-2-amino-1-(4-nitrophenyl)-1,3-propanediol, quinine, and hydroquinine.

34. The method claim 24, wherein the chiral auxiliary is ephedrine or an ephedrine derivative.

35. The method of claim 34, wherein the chiral auxiliary is (1S,2S)-(+)-Pseudoephedrine.

36. The method of claim 1, further comprising purifying the compound of formula (A-III) prior to the hydrolyzing step.

37. The method of claim 35, wherein the purification is performed using chromatography or crystallization.

38. The method of claim 1, wherein the hydrolyzing of the compound of formula (A-III) is performed using a base.

39. The method of claim 38, wherein the base is NaOH.

40. The method of claim 1, wherein R$^1$ is C$_{1-6}$ alkyl.

41. The method of claim 1, wherein R$^1$ is ethyl.

42. A method of making a compound of formula (I) or pharmaceutically acceptable salt thereof,

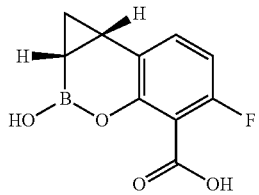

Formula (I)

comprising the steps of:

converting a compound of formula (A-II)

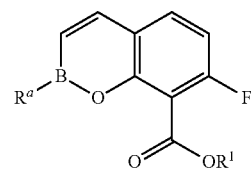

to a compound of Formula (A-III)

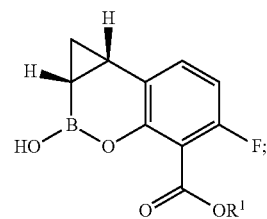

and hydrolyzing the compound of Formula (A-III) to form the compound of Formula (I), wherein:

R$^1$ is a carboxylic acid protecting group; and

R$^a$ is OH or optionally substituted —O—C$_{1-6}$ alkyl.

43. The method of claim 42, wherein the converting of the compound of formula (A-II) to the compound of formula (A-III) comprises combining the compound of formula (A-II) and one or more chiral auxiliaries to form a chiral complex having the structure of formula (A-II')

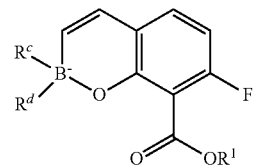

and reacting the chiral complex with a cyclopropylating agent, wherein RC and R$^d$ with any intervening atoms form an optionally substituted 4-7 membered heterocyclyl ring.

44. A method of making a compound of formula (I) or pharmaceutically acceptable salt thereof, comprising the steps of:

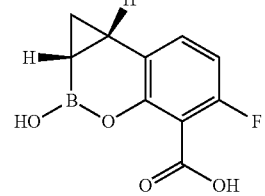

Formula (I)

reacting a chiral complex having the structure of formula (A-II')

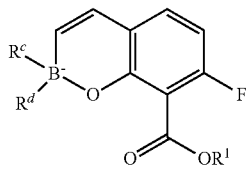

with a cyclopropylating agent to form a compound of formula (III)

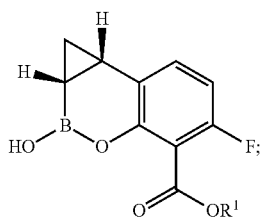

and
  hydrolyzing the compound of Formula (A-III) to form the compound of Formula (I),
  wherein:
  $R^1$ is a carboxylic acid protecting group, and
  $R^c$ and $R^d$ with any intervening atoms form an optionally substituted 4-7 membered heterocyclyl ring.

45. A method of making a compound of formula (A-II), comprising the steps of:

Formula (A-II)

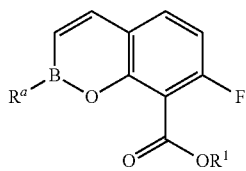

reacting a compound of formula (A-I)

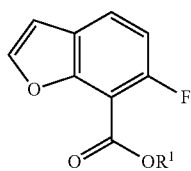

with a borylating agent to form the compound of formula (A-II),
  wherein:
  $R^1$ is a carboxylic acid protecting group; and
  $R^a$ is OH or optionally substituted —O—$C_{1-6}$ alkyl.

46. The method of claim 1, further comprising purifying the compound of formula (I).

47. The method of claim 1, wherein the compound of formula (A-I) is

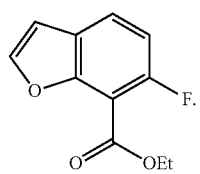 [SMILES: CCOC(=O)c1c(F)ccc2ccoc12]

48. The method of claim 2, wherein the compound of formula (A-II) is

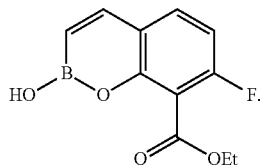

49. The method of claim 1, wherein the compound of formula (A-III) is

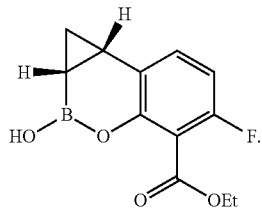

50. The method of claim 1, wherein the compound of formula (I) is

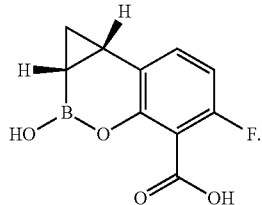

51. The method of claim 1, wherein the compound of formula (I) or its pharmaceutically acceptable salt is

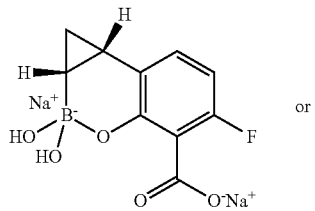

-continued

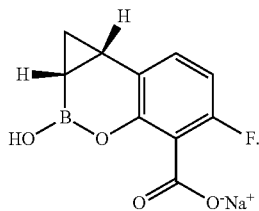

52. A method of preparing a compound of Formula (A-I),

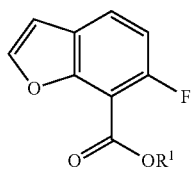

Formula (A-I)

comprising the steps of:
  reacting a compound of formula (A-V)

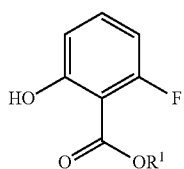

with an alkylating agent to form a compound of formula (A-VI)

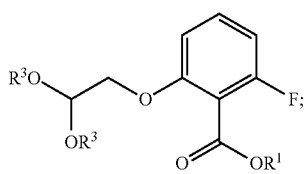

(A-VI)

converting the compound of formula (A-VI) to the compound of formula (A-I),
wherein:
$R^1$ is a carboxylic acid protecting group;
each $R^3$ is independently an optionally-substituted $C_{1-6}$ alkyl, or two $R^3$ together are optionally substituted $C_{2-3}$ alkylene and form an optionally substituted 5-6 membered heterocyclyl ring with intervening atoms.

53. The method of claim 52, wherein the alkylating agent is $CH(OR^3)_2CH_2X$ and X is a halogen.

54. The method of claim 52, wherein the alkylating agent is $CH(OEt)_2CH_2Br$.

55. The method of claim 52, further protecting the carboxylic acid in a compound of formula (A-IV)

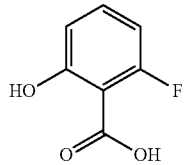

to form the compound of formula (A-V).

56. The method of claim 52, wherein the compound of formula (A-V) is

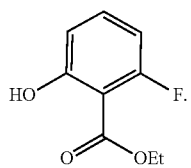

57. The method of claim 52, wherein the compound of formula (A-VI) is

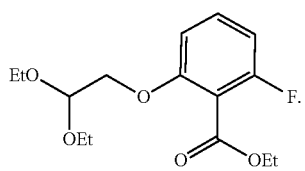 [SMILES: CCOC(=O)c1c(F)cccc1OCC(OCC)OCC]

58. The method of claim 52, wherein the compound of formula (A-I) is

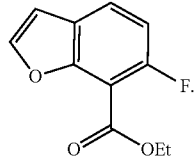 [SMILES: CCOC(=O)c1c(F)ccc2ccoc12]

59. A method of preparing a compound of Formula (A-I'), comprising the steps of:

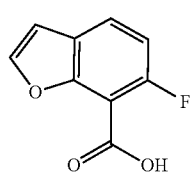

Formula (A-I')

reacting a compound of formula (A-V)

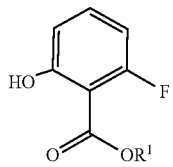

with an alkylating agent to form a compound of formula (A-VI')

(A-VI')

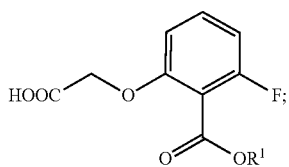

converting the compound of formula (A-VI') to a compound of formula (A-I), and hydrolyzing the compound of Formula (A-I) to form the compound of Formula (A-I'), wherein:

$R^1$ is a carboxylic acid protecting group.

60. The method of claim 59, wherein the alkylating agent is $COOR^4CH_2X$ wherein $R^4$ is an optionally-substituted $C_{1-6}$ alkyl and X is a halogen.

61. The method of claim 59, wherein the alkylating agent is $COOMeCH_2Cl$.

62. The method of claim 59, further comprising protecting the carboxylic acid in a compound of formula (A-IV)

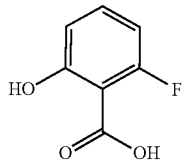 [SMILES: O=C(O)c1c(O)cccc1F]

to form the compound of formula (A-V).

63. A method of preparing a compound of formula (A-IV)

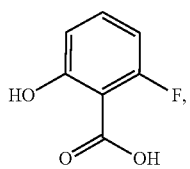

comprising hydrolyzing

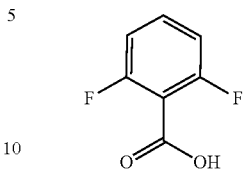

with a base to form the compound of formula (A-IV).

64. The method of claim 59, wherein the compound of formula (A-V) is

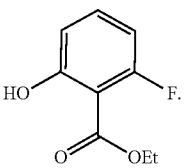 [SMILES: O=C(O)c1c(O)cccc1F]

65. The method of claim 59, wherein the compound of formula (A-VI') is

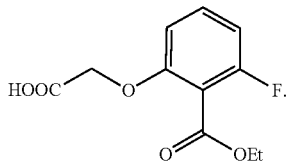 [SMILES: CCOC(=O)c1c(F)cccc1OCC(=O)O]

66. The method of claim 59, the conversion of the compound of formula (A-VI') to the compound of formula (A-I) further comprises converting the compound of formula (A-VI') to a compound of formula (A-VII')

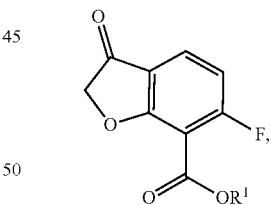

and reducing and dehydrating the compound of formula (A-VII') to form the compound of formula (A-I).

67. The method of claim 59, wherein the compound of formula (A-I) is

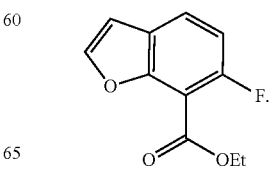

68. The method of claim 59, wherein the compound of formula (A-VII') is

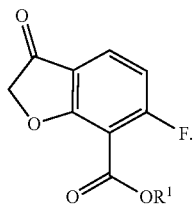

69. A compound having the structure of

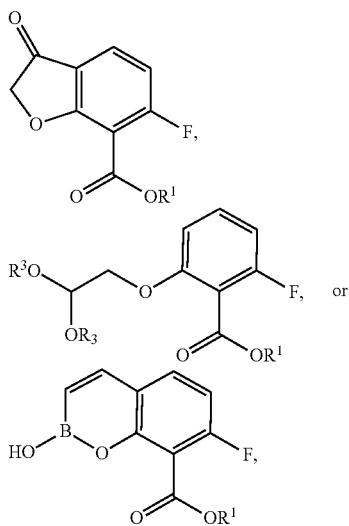

wherein $R^1$ is a carboxylic acid protecting group; and each $R^3$ is independently an optionally-substituted $C_{1-6}$ alkyl, or two $R^3$ together are optionally substituted $C_{2-3}$ alkylene and form an optionally substituted 5- or 6-membered heterocyclyl ring with intervening atoms; or a compound having the structure

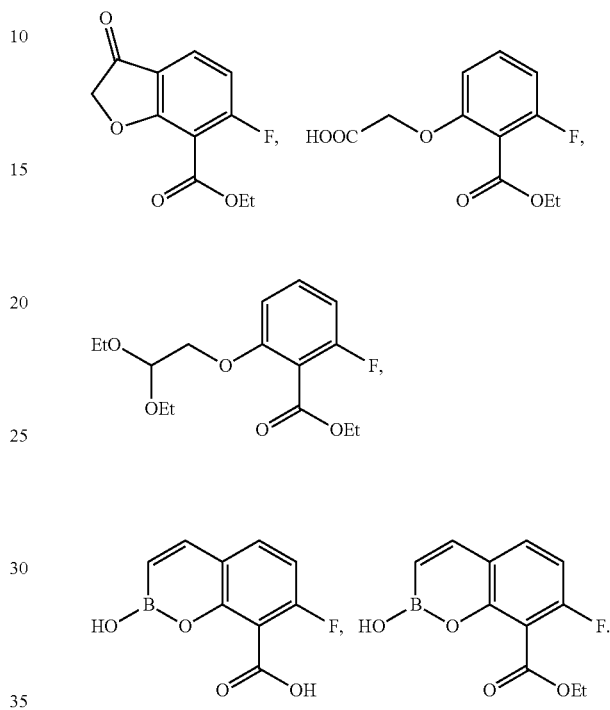

* * * * *